(12) United States Patent
John

(10) Patent No.: US 9,919,102 B2
(45) Date of Patent: Mar. 20, 2018

(54) MEDICAL DRUG DELIVERY SYSTEMS AND METHODS FOR DELIVERY OF MULTIPLE FLUIDS AND CONCENTRATIONS

(71) Applicant: Michael Sasha John, Larchmont, NY (US)

(72) Inventor: Michael Sasha John, Larchmont, NY (US)

( * ) Notice: Subject to any disclaimer, the term of this patent is extended or adjusted under 35 U.S.C. 154(b) by 733 days.

(21) Appl. No.: 14/070,522

(22) Filed: Nov. 2, 2013

(65) Prior Publication Data

US 2015/0018758 A1 Jan. 15, 2015

Related U.S. Application Data

(60) Continuation of application No. 12/853,941, filed on Aug. 10, 2010, now Pat. No. 8,591,498, which is a
(Continued)

(51) Int. Cl.
*A61M 5/168* (2006.01)
*A61B 5/00* (2006.01)
(Continued)

(52) U.S. Cl.
CPC ......... *A61M 5/16809* (2013.01); *A61B 5/412* (2013.01); *A61M 5/1408* (2013.01); *A61M 5/14276* (2013.01); *A61M 5/16827* (2013.01); *A61M 5/172* (2013.01); *A61M 5/1723* (2013.01); *A61M 25/003* (2013.01); *A61M 25/0026* (2013.01); *A61M 25/0097* (2013.01);
(Continued)

(58) Field of Classification Search
CPC .............. A61M 5/16809; A61M 5/172; A61M 25/0026; A61M 5/1408; A61M 5/14276; A61M 5/16827; A61M 5/1723; A61M 25/003; A61M 25/0097; A61M 2025/0037; A61M 2025/004; A61M 2205/3523; A61M 25/00; A61M 2005/14208; A61M 2025/0036; A61M 2025/0002; G06F 19/3468; A61B 5/412; A61B 5/14532
USPC .... 604/65–67, 131, 151; 128/DIG. 12, 13, 1
See application file for complete search history.

(56) References Cited

U.S. PATENT DOCUMENTS 3,841,308 A * 10/1974 Tate .................. A61M 25/0075
600/585
5,211,631 A * 5/1993 Sheaff ..................... A61M 5/44
604/103.05
(Continued)

*Primary Examiner* — Manuel Mendez

(57) ABSTRACT

A drug delivery system provides for controlled mixing of drugs, using flow controllers to guide drugs into single or multiple catheters, enabling a single lumen catheter to dispense multiple drugs, diluting a concentrated drug to provide varying drug concentration, using a buffer fluid to deliver precise amounts of drug or to separate drugs within a catheter, and using a patient's bodily fluid as a diluent or buffer fluid. A drug testing/filler apparatus may be used prior to system use to facilitate filling of multiple reservoirs and may also be used for refilling. The system can provide bolus or continuous delivery and enable the measured delivery of drug to selected distal locations at independent rates. New types of catheter systems, catheter hub assemblies, and uses therefore are also described. New methods for promotion of healthy pregnancy and treatment of a developing fetus are disclosed.

20 Claims, 11 Drawing Sheets

Related U.S. Application Data division of application No. 10/893,414, filed on Jul. 19, 2004, now Pat. No. 7,811,279, which is a continuation of application No. PCT/CA2004/001033, filed on Jul. 16, 2004.

(60) Provisional application No. 60/488,133, filed on Jul. 18, 2003, provisional application No. 60/574,195, filed on May 25, 2004, provisional application No. 60/587,870, filed on Jul. 15, 2004.

(51) Int. Cl.
*A61M 5/142* (2006.01)
*A61M 5/172* (2006.01)
*G06F 19/00* (2018.01)
*A61M 5/14* (2006.01)
*A61B 5/145* (2006.01)
*A61M 25/00* (2006.01)

(52) U.S. Cl.
CPC ...... *G06F 19/3468* (2013.01); *A61B 5/14532* (2013.01); *A61M 25/00* (2013.01); *A61M 2005/14208* (2013.01); *A61M 2025/0002* (2013.01); *A61M 2025/004* (2013.01); *A61M 2025/0036* (2013.01); *A61M 2025/0037* (2013.01); *A61M 2205/3523* (2013.01)

(56) References Cited

U.S. PATENT DOCUMENTS

| | | | | |
|---|---|---|---|---|
| 5,624,392 A | * | 4/1997 | Saab | A61F 7/123 604/113 |
| 5,628,733 A | * | 5/1997 | Zinreich | A61M 27/00 604/267 |
| 5,972,020 A | * | 10/1999 | Carpentier | A61B 17/3421 294/104 |
| 6,048,328 A | * | 4/2000 | Haller | A61M 5/14276 604/131 |
| 6,198,966 B1 | * | 3/2001 | Heruth | A61M 5/14276 604/20 |

\* cited by examiner

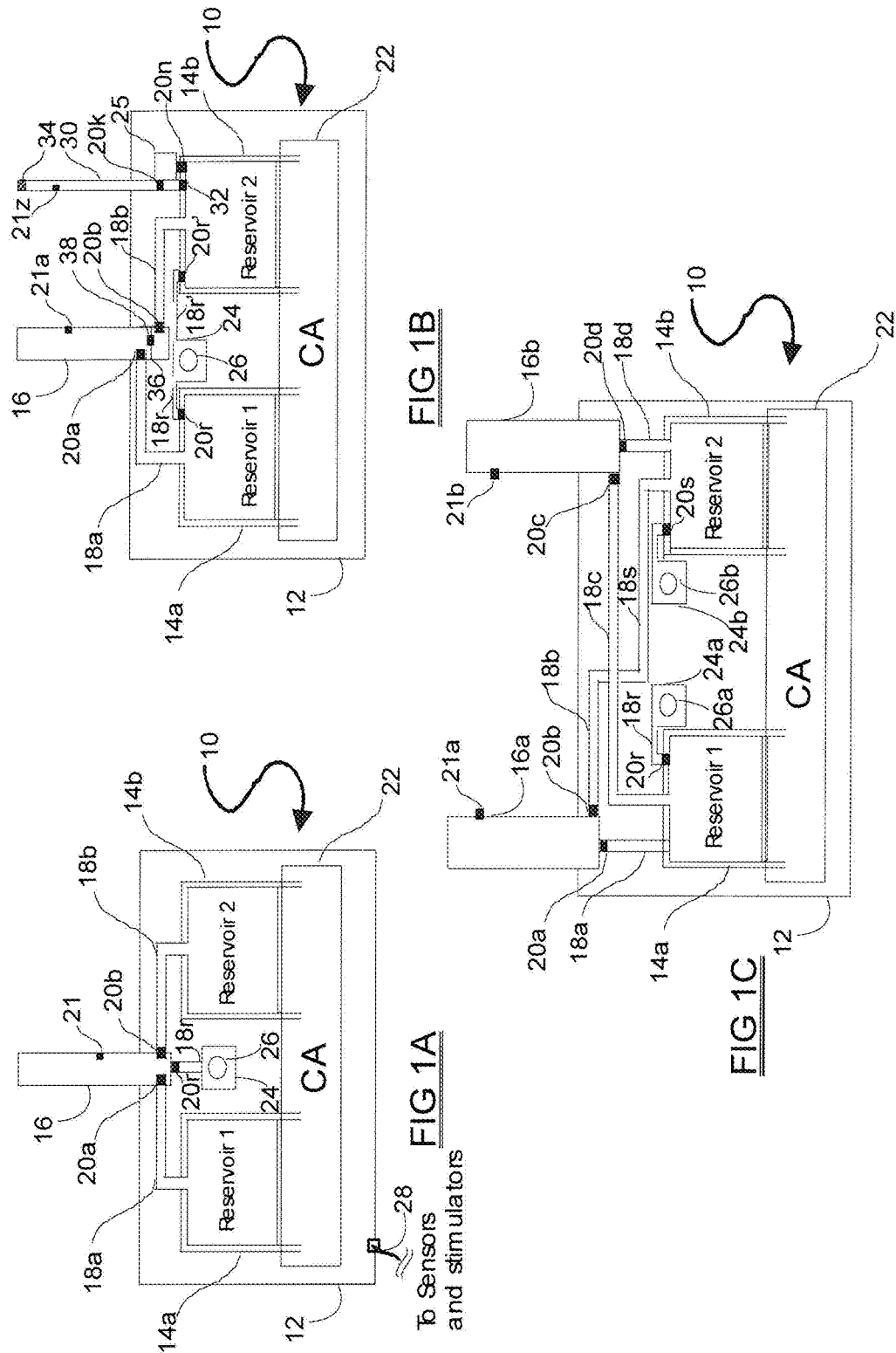

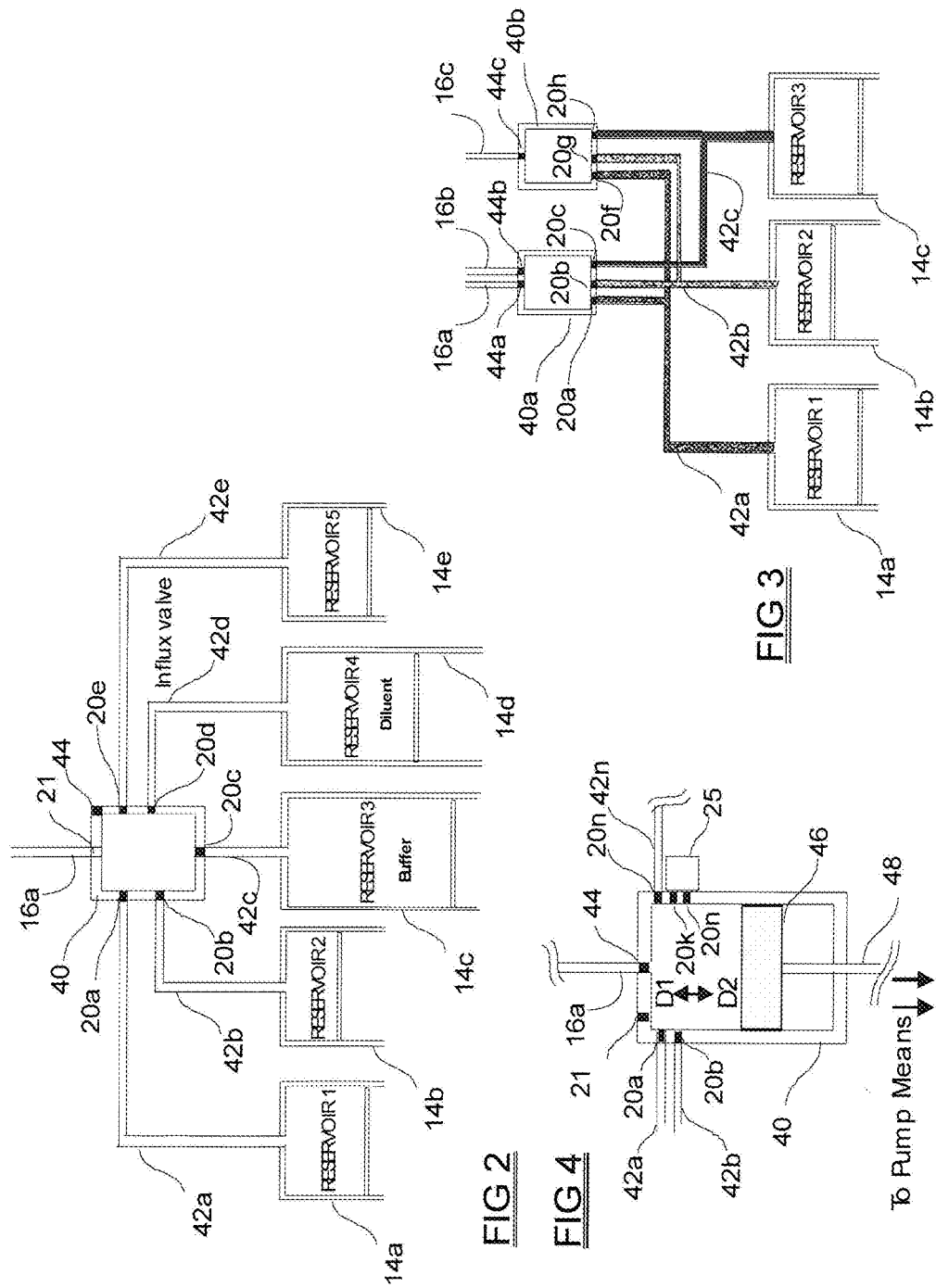

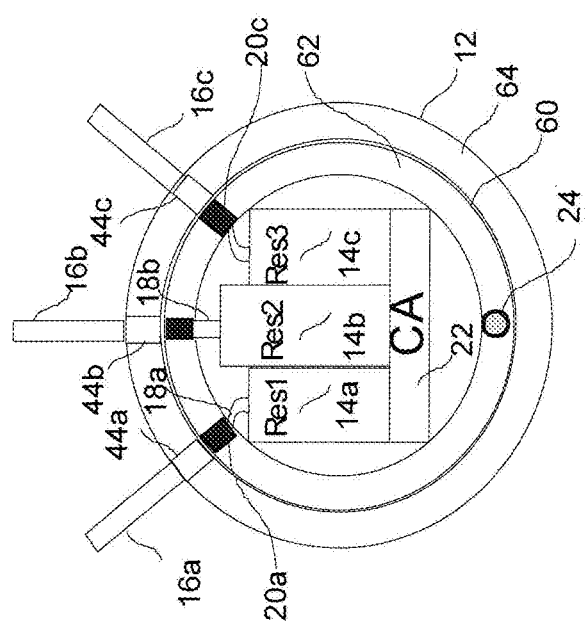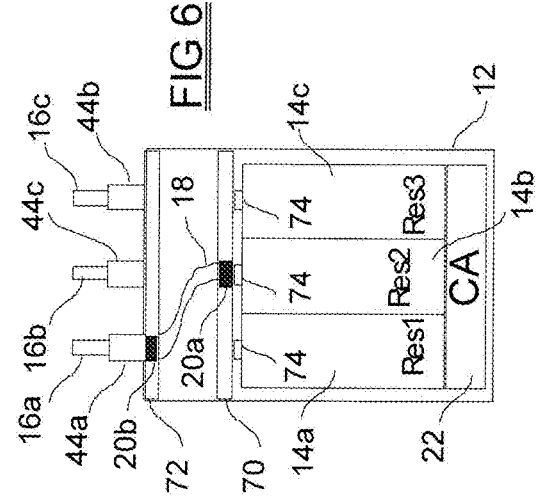

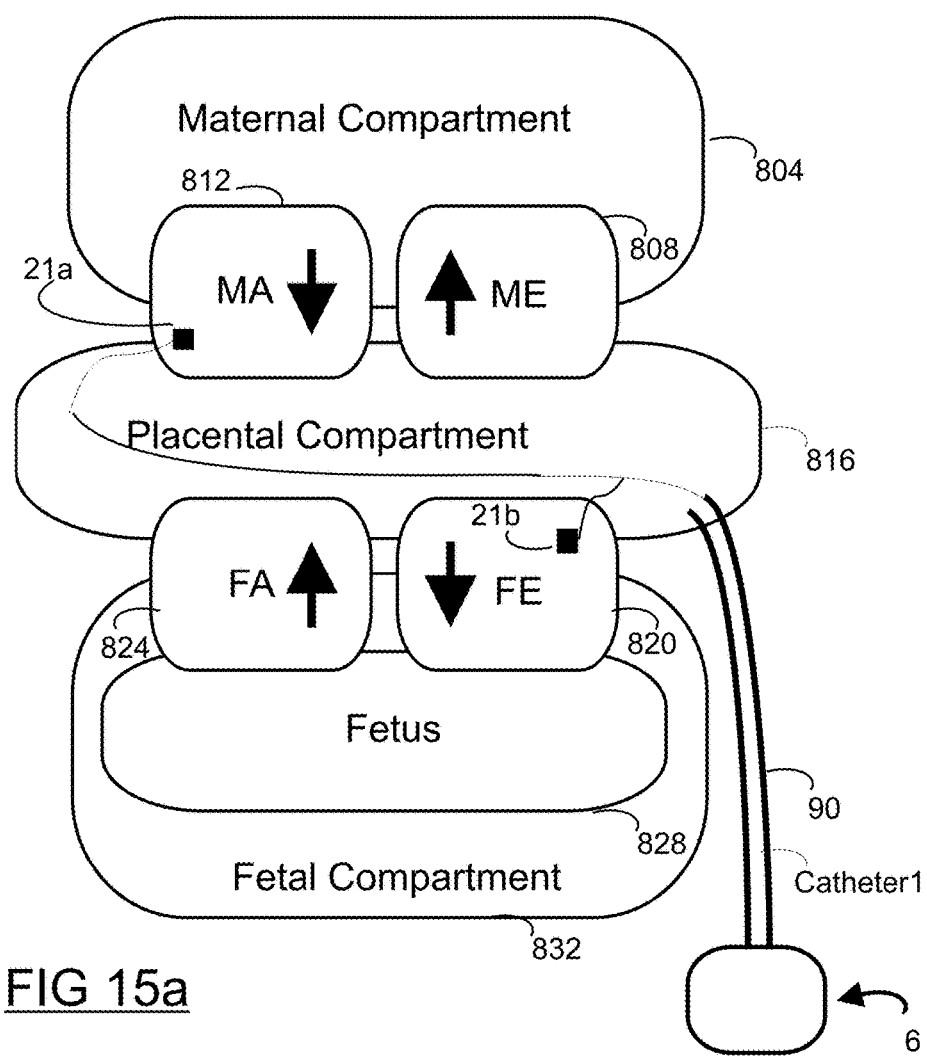
FIG 15a
FIG 15b
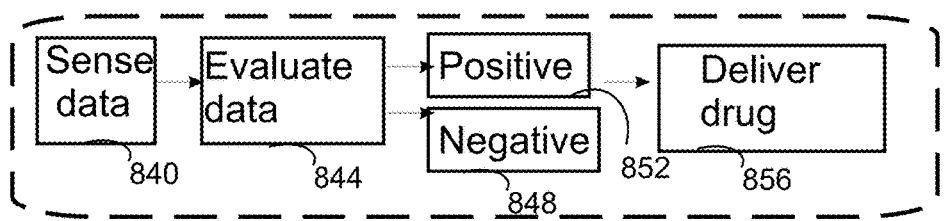

MEDICAL DRUG DELIVERY SYSTEMS AND METHODS FOR DELIVERY OF MULTIPLE FLUIDS AND CONCENTRATIONS

This is a continuation of application Ser. No. 12/853,941 filed on 2010 Aug. 10 which is a divisional of U.S. application Ser. No. 10/893,414 filed on Jul. 19, 2004 which is now U.S. Pat. No. 7,811,279, which is a continuation of PCT application No. PCT/CA2004/001033, filed on Jul. 16, 2004, which claims the benefit of Provisional Application No. 60/488,133, filed on Jul. 16, 2003, and claims the benefit of Provisional Application No. 60/574,195, filed on May 25, 2004, and further claims the benefit of Provisional Application No. 60/587,870, filed on Jul. 15, 2004.

The present invention relates to medical devices, and more particularly to partially or completely implantable drug delivery systems which can deliver one or more stored substances.

BACKGROUND

Patients often require continuous or bolus administration of medications which can be delivered at regularly occurring times, times dictated by a treatment regimen, in response to a patient's request, or in response to a biological/physiological event. An increasing assortment of implantable drug delivery systems are being designed to treat patients who may use the drug delivery technology to dispense therapeutic agents to treat medical conditions such as diabetes, arthritis, cancer, movement disorders such as spasticity, heart conditions and irregularities, various neurological or psychiatric conditions, disorders of the digestive system, autoimmune disorders, and many other medical conditions and disorders as well. The medical drug delivery technology can be used for a wide variety of medical, veterinary, pharmaceutical and research purposes, can be totally or partially implantable or, if small enough, can be ingestible.

Implantable osmotic pumps have been known for some time (e.g., U.S. Pat. No. 4,588,394). The more recent generation of implantable drug delivery systems can deliver two or more substances (e.g., U.S. Pat. No. 3,449,983), at controlled rates of delivery (e.g., U.S. Pat. No. 5,240,713). U.S. application 60/284,771 (the '771 application) and provisional Ser. No. 10/099,060 (the '060 application) provide for a programmable implantable pump system with several reservoirs and a multiple lumen catheter. The '711 application provides for bolus drug delivery over a short period of time, for delivering multiple substances independently at programmed rates of delivery to one or more regions, and for drug delivery based upon physiological need. However, mixing of different drugs between reservoirs is not addressed.

The '711 patent application discloses a multiple lumen catheter for delivering multiple substances to a specific site by using concentrically embedded lumen. This technique causes the diameter of the outer lumen of the catheter to increase, requiring more material, and creating a catheter which may not bend easily, and which may be more difficult to use when treating certain disorders, such as those of the central nervous system, where a smaller diameter catheter may be advantageous. A further disadvantage is that the internal lumen can break and be undetected. Further, when the diameter of a multiple lumen catheter grows beyond a certain limit, the amount of substance which is chronically held in the outer lumen may become great, thus depleting the amount of that substance which is in the pump and ready for delivery, and also increasing the probability of unwanted leakage. Further, having several multi-lumen catheters necessitates a considerable amount of substance, compared to a small diameter catheter.

U.S. provisional application Ser. No. 10/251,941 discloses a drug delivery system which contains a series of chambers which may each hold a different drug, each of which can be sent to different catheters. The '941 also contains an accumulator chamber between the reservoirs and the catheter, which is provided to hold drug overflow. While drugs may be mixed in the '941 application, this occurs by breaching the drug chambers themselves so that 100% of the drugs in those chambers become mixed.

Mixing of drugs can be important in order to produce therapeutic effects. For example, in chemotherapy, some of the drugs should not be mixed until immediately prior to use. Some drugs may potentiate the effects of other drugs, such as Sufentanil and Clonidine as described in U.S. Pat. No. 6,471,688 (the '688 patent), incorporated by reference herein. The '688 patent feeds two drugs to the same catheter, and can be designed to keep them from mixing until they reach the intended delivery site by using a dual, rather than a single, lumen catheter. In this embodiment the timing of the mixing is related to the rate of drug delivery. One disadvantage with this system is if a drug is to be delivered rapidly, but the desired mixing is to occur slowly or prior to delivery, the invention of the '688 patent would not achieve the desired drug mixing during the drug delivery.

U.S. Pat. No. 5,980,508 describes a system that allows for multiple drugs, multiple doses, and continuous or pulsatile/interval delivery. However, the technology is sub-optimal because the concentration and delivery system must be configured prior to the implantation of the pump, rather than being dynamically adjusted once implanted, based upon the needs of the patient.

U.S. Pat. No. 4,588,394 (the '394' patent) teaches a pump that has a separate single drug reservoir and a valve arrangement between the pump and the reservoir, however, the pump is between the catheter and the reservoir, and the intention of the invention is to provide an easily accessed refillable reservoir which can be located remotely from the pump, catheter, and the site of delivery. The '394 patent also describes, a two-step procedure which controls an arrangement of valves to realize filling and emptying the pumping chamber while decreasing the chance of the inadvertent introduction of the medication to the patient.

U.S. Pat App No 2002/0192751 A1 (the '751' application) teaches methods and devices for modulating the rate of delivery of a drug by simply diverting a drug away from a single delivery pathway using a remotely controllable flow regulator. The flow regulator only affects the amount of drug going to a single catheter. The diverted drug can be sent into the systemic circulation or captured in a waste reservoir. However, the waste reservoir is different from a method which utilizes the diverted drug since the drug in the waste reservoir is not used at a later time. Further, the flow regulator does not address the existence of the drug which is already in the catheter, which is an issue when using multiple drugs since this drug must be eliminated (e.g., dispensed or purged) before a subsequent drug can be delivered.

While some prior art (e.g., US 2002/0156462) teaches using multiple reservoirs and multiple catheters or multiple lumens, each reservoir is uniquely connected to a single lumen or catheter. Accordingly, this prior art does not teach more than one drug to be output from each respective lumen or catheters. Prior art U.S. Pat. No. 6,471,688 enables drugs from multiple reservoirs to be dispensed from a single catheter to a single target region within the body of the patient, but does not teach how to deliver drugs to multiple target regions simultaneously. Prior art U.S. Pat. No. 6,471,688 also teaches a system which can allow for a single fluid from a single reservoir to be dispensed at multiple locations at the distal end of the catheter.

Drug delivery systems containing sensors and multiple pumps have been described which allow the delivery of drug to occur in response to a physiological event. For example, U.S. Pat. No. 6,066,163, describes an adaptive neurostimulation system which contains a reservoir infusion apparatus which stimulates the central nervous system with drugs in response to abnormal states which are sensed by one or more sensors. U.S. Pat. No. 5,062,841 discloses an insulin pump which can be used to pump insulin directly into the bloodstream in response to blood glucose levels. U.S. Pat. No. 5,433,701 discloses an active ocular pressure control device which includes a pump which is selectively operated in response to a control signal from a pressure sensor. However, these patents relate primarily to algorithms and methods of using the sensed data to control the pumping/drug delivery system and dispense an appropriate drug.

The prior art US 2003/0171738 (the '738 application) suggests continuously drawing upon fluids available from the implantee, in response to the immediate drug delivery needs of the implantee, which is disadvantageously dependent upon the availability of the implantee's fluids concurrent to the time of delivery. Further, a chamber is provided in the drug delivery device of the '738 application (see FIG. 3A), but this chamber only leads to a single catheter and the chamber has a fixed volume. Further, in FIG. 1a of the '738 application a carrier fluid from the reservoir is mixed with various drugs located in the catheter and somehow transmitted in a distributed fashion to several catheters, but in this case the drugs are undesirably mixed deterministically by the path of the flow of fluids over the "wells" of a microchip which contain drugs. Much of the technology described in the '738 patent relies on a catheter which contains a microchip drug delivery device. This microchip cannot contain much drug and is difficult to refill, and instead of being refilled is sometimes simply replaced, thereby requiring possibly complicated surgical intervention. Further, since drugs are dispensed by opening "wells", a specific amount of drug is suddenly made available to the carrier fluid which transmits the drug to the implantee. It is not clear what might occur with the remainder of the drug which is contained in the catheter after the necessary amount has been delivered to the subject. In other words, when the amount of drug which is necessary for a specific drug regimen is known prior to implantation, then an appropriate amount of drug can be put into the "wells" of the microchip device. However, in the case where drug is delivered based upon sensed data and the object is, for example, to maintain a sensed parameter within certain limits, the use of a microchip incorporated into a catheter, as is described by the '738 application has an inability to provide a drug concentration and amount which is optimal to effect a desired change.

It is an object of the present invention to provide a drug delivery system and method to obviate or mitigate at least some of the above presented disadvantages.

SUMMARY OF THE INVENTION

The drug delivery systems of the present invention can provide for mixing various drugs in an optimally controlled manner, use flow controllers to guide multiple drugs into a single or into multiple catheters, enable a single lumen catheter to treat a specific region with several drugs, allow for dilution of a concentrated drug in order to both increase the time between refilling and also to provide any concentration of a drug that might be desired, provide for using a buffer fluid to deliver exact amounts of several drugs from the same catheter or to separate several drugs within a single catheter, use external fluid present in the human body either as a diluent or buffer fluid, and provide for a drug testing/filler apparatus to be used prior to implant to ensure proper function and easy means of filling multiple reservoirs with different fluids, and also after implant for refilling operations. The drug delivery system (DDS) can perform both bolus and continuous delivery of substances, and enable the measured delivery of any one of several drugs to one or more distal locations at independently programmable rates. New methods for using the DDS in the promotion of healthy pregnancy and treatment of a developing fetus are also possible.

According to a first aspect there is provided an implantable drug delivery device for controlling a dispensing of a fluid drug to an internal target site of a patient, the device comprising: a first reservoir for storing a first fluid; an input port in fluid communication with the first reservoir; an output port in fluid communication with the first reservoir; a flow control system for controlling the transfer of the first fluid between the respective ports and the first reservoir, the flow control system having at least one flow controller; and a flow control module for directing the at least one flow controller to direct the flow of the first fluid between a selected one of the ports and the first reservoir.

According to a further aspect there is provided a catheter assembly for directing a selected fluid to at least one target site of a patient, the assembly comprising: a first lumen having a first proximal end for coupling to a drug delivery device and a first distal end for positioning at the target site; a second lumen having a second proximal end for coupling to the drug delivery device and a second distal end for positioning at the target site, the first lumen and the second lumen adapted for fluid communication therebetween; a flow control system positioned at the first and second distal ends for directing inter-lumen fluid flow between the first and second lumens and for directing output fluid flow from the distal ends to the target site, the flow control system having at least one directional flow controller adapted to receive at least one control signal from the drug delivery device.

According to a still further aspect there is provided a method of outputting by a catheter assembly a selected fluid to a target site of a patient, the catheter assembly having a first lumen and a second lumen adapted for fluid communication therebetween and a flow control system for directing inter-lumen fluid flow between the first and second lumens and for directing output fluid flow from the distal ends of the lumens to the target site, the method comprising the steps of: delivering into the catheter at least two fluids, one of which is a buffer fluid, such that an alternating sequence of the fluids resides in the lumens; configuring by the flow control system the fluid flow of the lumens for inter-lumen fluid flow and inhibiting fluid flow output from the lumens; operating a pump in fluid communication with the lumens to perform inter-lumen circulation on the fluid sequence within the lumens until a selected one of the fluids resides near the distal tip of the first lumen; configuring by the flow control system to inhibit the inter-lumen fluid flow and to enable output fluid flow from the distal end of the first lumen of the selected fluid; and pumping the selected fluid as the output fluid from the first lumen.

According to a still further aspect there is provided an apparatus for configuring a drug delivery device, the device including at least one fluid reservoir in fluid communication with a fluid output port and a fluid input port and at least one fluid flow controller for controlling fluid input and output with respect to the fluid reservoir, the apparatus comprising; a fluid input component for recording an amount value of input fluid directed to the input port of the device from a fluid source; a flow control component for coupling to the device to configure the fluid flow controller to direct the input fluid from the input port into the fluid reservoir; a sensor component for recording at least one operational state value of the device including a fill state value of the reservoir; and a processor component for accepting user input commands and for coordinating the operation of the input, control, and sensor components in response to the user input commands; wherein the recorded values are provided to the user of the apparatus.

Accordingly, it is a feature of the present invention to provide for a drug delivery system which is capable of controlled delivery of both bolus and continuous flow of one or more substances, which may be substantially mixed or which may be presented sequentially, and which are delivered through a single catheter or through multiple catheters.

It is another feature of the present invention to provide for a drug delivery system which is capable of delivering more than one concentration of a substance, and perform dose titration by modifying either the concentration, or rate of dispensing, or both.

It is another feature of the present invention to provide for a drug delivery system which draws upon and utilizes a biological fluid available from the patient, rather than, or in addition to, a synthetic fluid, as an active drug, a buffer fluid, or a diluent, and thereby decreases the need for filling the drug delivery system from a source outside the body.

It is an advantage of the present invention to provide for a drug delivery system which is refillable with a diluent or buffer fluid which is a non-controlled (e.g., saline) rather than a controlled substance (e.g., narcotic), in order to facilitate drug delivery system use over time. For example, rather than refilling the drug delivery system with an analgesic agent, a diluent can be refilled which acts to dilute a very concentrated supply of analgesic drug which is stored in the drug delivery system.

It is another advantage of the present invention to provide for an implantable drug delivery system which provides for facilitating re-filling procedures by more often only requiring the replenishment of a single substance, which may be biologically inert, that is used as a buffer fluid or diluent, to efficiently dispense one or more drugs.

It is another feature of the present invention to provide for an implantable drug delivery system which uses flow controllers to enable the delivery of more than one substance through each of one or more catheters and also to allow each reservoir of the system to dispense fluid through each of several catheters.

It is another feature of the present invention to provide for an implantable drug delivery system which contains a mixing chamber capable of mixing two or more fluids to produce one or more concentrations of a drug and/or a mixture of several substances.

It is another feature of the present invention to provide for an embodiment of the implantable drug delivery system which is capable of improving delivery of a substance to a site which is relatively distal to the means for pumping, in part, by using at least one mixing chamber, in conjunction with diluent and buffer fluids.

It is another feature of the present invention to provide for an implantable drug delivery system which is capable of delivering more than one substance through each of one or more specific catheters.

It is a further feature of the present invention to provide for a multiple catheter implantable drug delivery system wherein each catheter is capable of independently delivering multiple medications to a single region at independently controlled times and rates.

It is a further feature of the present invention to provide an accessory which assists in filling, refilling, calibration, and testing of a drug delivery system which contains at least two fluids.

It is a further feature of the present invention to provide for a multiple lumen catheter which enables fluids dispensed by the drug delivery system to be circulated within the lumen so that a desired drug can be transported to its distal tip just prior to being delivered to a patient.

It is a further feature of the present invention to provide for a multiple stage catheter which contains at least two stages, wherein the first stage contains multiple lumen and a second stage only contains a single lumen, having a relatively small cross sectional volume as is desirable in some applications such as direct brain infusion.

It is a further feature of the present invention to facilitate a healthy birth process by delivering drugs to achieve for example: increasing the chance for conception, increasing the health of a developing fetus, assisting in normalizing fetal-placental flow or in compensating for abnormal flow, sensing the properties of the fluid in the vessels of the umbilical cord and using the properties of the fluids of the umbilical cord to guide the DDS dispensing or pumping operations, decreasing the risk of illness of the fetus, providing nutrients in response to lack of nutrients provided by the maternal sources, decreasing the unwanted effects of maternal exposure to substances that could be harmful to the fetus, in providing gene or germ therapy to the fetus, delivering therapeutic drugs in order to decrease the variability of the substances provided by the mother (e.g., as may occur when the mother has a metabolic disorder), decreasing the risk of infection or other viral or bacterial abnormality in the womb, decreasing the probability of premature labor, and assisting in extending the labor period.

Another feature of the present invention utilizes drug delivery to increase the likelihood of optimizing the health of the fetus. The drug delivery is directly to the fetus rather than to the mother, via a uterine target such as for example, the supporting vasculature, the placenta, or the vessels of the umbilical cord.

Another feature of the present invention uses a method which senses concentrations of substances in the umbilical artery or vein, the placenta, other structure of the fetal compartment, and evaluates this sensed data, and delivers drugs based upon this evaluation to a target in the fetal compartment or in the placenta in order to achieve a desired therapeutic result and/or in order to protect against a substance that could affect the fetus.

Another feature of the present invention uses a method which senses data from at least two sensors in the fetal compartment, in the maternal compartment, or in both compartments, and creates an input/output ratio or other index (which may be based upon a model) on which drug delivery to a uterine target or directly to the fetus, may be based.

Another feature of the present invention uses a method which senses intra-uterine, placental, umbilical (e.g., umbilical vein), amniotic and/or maternal levels of toxic substances (or substances which may become noxious when above certain levels), such as antidepressant drugs or their metabolites, and dispenses substances to counteract the effects that such unwanted substances may have for the fetus.

Another aspect of the present invention provides a method of using a drug delivery system for decreasing the risk of premature labor or miscarriage, by sensing physiological and chemical changes of the womb and delivering drugs to stop the process of premature labor or miscarriage (e.g., premature contractions), if either the physiological or chemical changes indicate that miscarriage may be beginning.

Further, another aspect of the present invention provides drug delivery to modify the content of breastmilk in order to optimally meet the needs of a developing infant. Sensing biological compounds in the milk or in the infants and then changing the drugs which are dispensed is not discussed in the prior art. The drug delivery system can deliver fluids to the mammary glands and related system of ducts and glandular tissue, in order to alter the content of the milk and other secretions, or in order to deliver fluids containing, for example, nutrients, immunoglobulin agents, hormones or synthetic hormonal analogs or antagonists or agonists, and other substances in order to modify the amount and content of milk that is produced and imbibed by the infant.

BRIEF DESCRIPTION OF THE FIGURES

These and other features of the preferred embodiments of the invention will become more apparent in the following detailed description in which reference is made to the appended drawings by way of example only, wherein:

FIG. 1a shows an exemplary embodiment of a drug delivery device;

FIG. 1b shows an alternative exemplary embodiment of the drug delivery device of FIG. 1a;

FIG. 1c shows an alternative exemplary embodiment of the drug delivery device of FIG. 1a;

FIG. 2 shows a partial view of an exemplary embodiment of the drug delivery device of FIG. 1a having a mixing chamber;

FIG. 3 shows an alternative exemplary embodiment of the drug delivery device of FIG. 2, now with two mixing chambers;

FIG. 4 shows a variable volume embodiment of the mixing chamber of FIG. 2;

FIG. 5 shows an exemplary embodiment of the drug delivery device of FIG. 1a;

FIG. 6 shows an exemplary embodiment of the drug delivery device of FIG. 1a;

FIG. 7b shows a further embodiment of the two-lumen catheter of FIG. 7a;

FIG. 10 shows a DDS tester/calibrator/filling apparatus for use with the medical drug delivery device of FIG. 1a;

FIG. 12a shows an embodiment of a multiple catheter hub connection assembly (CHCA);

FIG. 12b is shows a single catheter connection assembly (CCA) as a further embodiment of the assembly of FIG. 12a;

FIG. 14 shows a method for operating the device of FIG. 1a;

FIG. 15a shows one embodiment of a drug pump implanted in a mother for drug delivery to the fetus; and FIG. 15b shows one embodiment of a method of using the drug pump to treat the fetus.

DETAILED DESCRIPTION

Figure 7A:
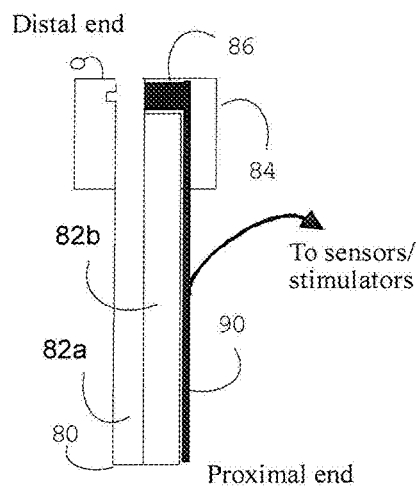
FIG. 7a shows a dual-lumen catheter having a flow control at its distal end.

The medical drug delivery system (DDS) is an apparatus which is part of a system that dispenses drugs into any region of the implantee, including the body, organs, brain, vasculature and areas related to reproduction. The terms "drug", "medication", "active agent", or "fluid" can all be used to mean a therapeutic agent delivered with the goal of producing a desired effect. The drug may often be stored within the DDS in the form of a fluid or gel, however, the DDS can also contain powder forms of drugs which are mixed with, dissolved or suspended within fluids prior dispensing them to an implantee. The types of fluids which can be delivered by the DDS include, but are not limited to, medications, vitamins, nutrients, chemicals, antibiotics, hormones or hormonal drugs, catalysts, gene/germ therapies, anticoagulants, chemotherapeutics, antigens, anti-tumor agents, analgesic, anti-inflammatory agents, antioxidants, parasiticides, and others. Other drugs which can be delivered are listed in prior art (e.g., U.S. Pat. Nos. 5,980,508, 6,571, 125 & US 2003/0093063 A1, & US2003/0130645 A1, which are incorporated by reference herein). The DDS can deliver fluids that contain nanoparticles or that activate drugs or nanoparticles (termed "catalysts"), and/or cause the membranes of the nanoparticles to disintegrate and release drugs. The DDS can emit light or energy at a particular frequency within its internal components (e.g., via a non-thermal laser generator located in the mixing chamber), within its catheters, or from the tip of the catheters in order to activate, for example, photosensitive drugs/nanoparticles that are contained within the fluids it releases to various targets (e.g., porfimer sodium, Photofrin, Verteporfin). Nanoparticles (and the similar "microemulsions" and microfabricated particles) can contain substances such as medications, and can, for example, be introduced into the body to move along in the bloodstream toward their targets, or can be delivered locally.

The types of medical conditions that the DDS might be used to treat include, but are not limited to cardiovascular abnormalities and diseases, arthritis, pain disorders, disorders of the spine, neurological or psychiatric pathology, migraine disorders, fetal disorders, infections, cancer, diabetes, systemic illnesses, biological and metabolic abnormalities requiring treatment. The DDS can be used in medical, contraceptive, gynecological, pharmaceutical, veterinary, and research applications. Additionally, the DDS can be implanted in a mother and instead of, or in addition to, delivering drugs to the mother, can deliver drugs directly to a developing fetus, or into the umbilical cord, or to an area near the fetus (e.g. the amniotic fluid) in order to provide drug to the fetus or in order to effect a therapeutic change in that area. The DDS can also be used to change the characteristics of the breastmilk so that therapy can be achieved after birth.

Terminology used herein is for illustration and convenience only and is not to be taken as a limitation of the invention. Words such as "upper", "lower", or "downward" can be used to describe embodiments shown in the figures. However, the components of the DDS can be oriented and configured in many directions and the terminology should be understood as encompassing such variations unless specified otherwise. More specifically, "upstream" or "proximal" refer to a point in the fluid path that is closer to reservoirs while "downstream" or "distal" refer to a point in the flow pathway which is operationally closer to point at which the fluid will be delivered to the implantee. Operating components in a "forward" direction causes fluid to move distally while causing fluid to travel in a "reverse" direction signifies moving fluid upstream towards the reservoirs. Further the illustrations are not drawn to scale, and the various components can be different shapes and sizes as long as the function does not deviate from the structures illustrated in the figures. For example, the width (i.e., internal circumference) of the lumens of the catheters may be much smaller than those which are shown here, or may vary in their width at different points (e.g., at their distal tips), but in order to illustrate internal components of the catheters, the catheters were shown with large internal widths.

Turning to FIG. 1a, an implantable DDS 10 is shown. In this exemplary embodiment, the internal components of the system 10 are enclosed in an implantable housing 12 which may be made of titanium with a plastic outer coating. Within the housing 12, is located fluid containment means which is realized in FIG. 1a by a first reservoir 14a and second reservoir 14b, which are connected to a catheter hub 16 or output port. The catheter hub 16 allows a catheter to be attached to the DDS. For example, catheters can be slipped over, or screwed onto, the hubs, or the DDS can be manufactured with the catheters glued to or formed upon the catheter hubs. In this specification, a catheter refers to a single lumen through which fluid may travel. In the case of a multiple lumen catheter, each lumen can be connected to a separate catheter hub. The first reservoir 14a is connected to the catheter hub 16 by a fluid channel 18a, which in this example, is realized by a connection tube. The fluid channel 18a allows fluid to travel from the first reservoir 14a to the catheter hub 16 (or to an intervening internal component such as a mixing chamber 40—see FIG. 2—which it enters prior to arriving at the catheter hub 16) and fluid channel 18a may be formed as part of the reservoir 14a. The second reservoir 14b is also connected to the catheter hub 16 by fluid channel 18b, which in this case is also a connection tube. The first and second reservoirs 14a-b can also be referred to as "Res1" and "Res2", respectively. Flow from Res1 14a through the fluid channel 18b to the catheter hub 16 is controlled by the control apparatus (labeled as "CA" in the figures and also referred to as flow control module) 22 which controls flow by operating one or more pumps to cause fluid to flow and also manipulating the state of flow controllers (e.g., 20a-b) to control the path through which this fluid may travel. For example, the control apparatus can deliver fluid from Res1 14a by operating a pump 23 so that fluid is pushed out of Res1 14a and changing the state of flow controller 20a for the Res1 14a in order to control the flow of fluid, which in this case entails permitting fluid to flow from Res1 14a to the catheter hub 16. The flow controller 20b for Res2 14b is also shown.

Sensors such as the sensor 21 placed in the catheter hub 16 can measure the rates at which fluids travel, or "flow rate" and send this information to the control apparatus 22. The term "sensor" can refer to a sensor placed anywhere, either within or outside of the DDS housing, which provides sensed data relating to physical, chemical, physiological or other measurements relating to DDS operation, drug delivery, or the implantee. Sensors of the DDS can also include electrical (e.g., to measure the amount of residual charge in power supply, current flow, or impedance), chemical, optical, thermal, flow, volume, position, pressure, gas, oxygen, and biosensors or other types of sensors. A sensor may provide sensed data relating to multiple characteristics, for example, the flow rate, concentration, and pressure of a fluid which is being delivered by the DDS. Accordingly, a sensor may be an aggregate of several types of specialized structures each configured to sense a different fluid characteristic of the environment in which it is located.

The sensors utilized by the DDS can include, but are not limited to, electrical (e.g., EKG electrode), chemical (e.g., pH), electrochemical sensors (e.g., microelectrode arrays made by Quanteon for measuring substances such as glutamate), or optical sensors (e.g., which can detect O2, CO2, and PH levels, and which can take the form of pulse oximeters or chromophore-based IO biosensors having one or more sensing fibers), and can detect physical measures (e.g., pressure, temperature, flow, acceleration), enzymatic changes, or the state of tissue or an organ. The sensors can be biosensors which are capable of sensing one or more specific molecules or other biological substances, either directly or by means of their metabolites. As is known to those in the art, sensor technology is continually advancing, however, some types of sensors which may be used are now described. The sensors can be similar to, based upon, or incorporate, nanotechnology such as Nanogen's Nano-Chip™. Electronic Microarray, which uses a tiny, silicon chip that is capable of rapid identification and precise analysis of biological molecules. Additionally, an interaction between molecules may also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. U.S. Pat. No. 5,791,344 to Schulman et al. entitled "Patient Monitoring System," proposes a system to monitor the concentration of a substance in a subject's blood wherein one enzymatic sensor is inserted into a patient to monitor glucose. Similarly, EP1011797 to Schulman et al, entitled "System of Implantable Devices for Monitoring or Affecting Body Parameters," proposes using microsensors to measure, for example, glucose level, oxygen content, temperature, and other measures. There are also a number of implantable medical devices and systems which monitor physiological data associated with the heart via telemetry (e.g., U.S. Pat. No. 5,720,771 to Snell entitled, "Method and Apparatus for Monitoring Physiological Data From an Implantable Medical Device"). Additionally, US application 20030171711, entitled "Closed-loop drug delivery system" employs a chromophore-based IO biosensor having one or more sensing fibers implanted directly into patient tissue. The contents of these prior art examples are hereby incorporated by reference as if recited in full herein. When possible, the DDS can rely upon completely implanted sensors, but may also communicate with, external devices, or may utilize information derived from assays, or laboratory techniques, in order to obtain accurate sensed data of the desired measures.

Figure 9:
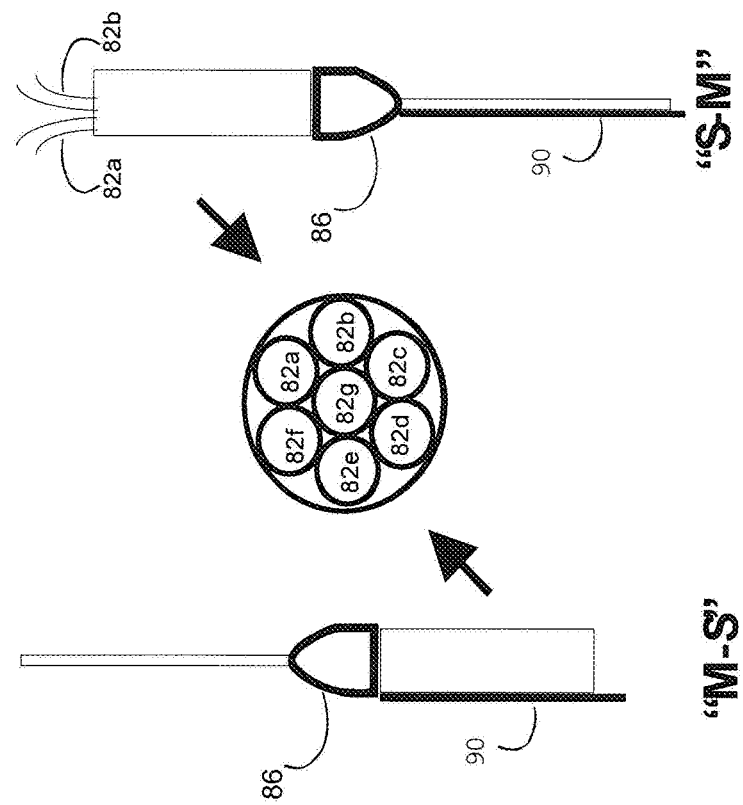
FIG. 9 shows illustrative embodiments of multi-stage catheters with flow controllers.

The term "flow controller" can refer to one or more valves (e.g., a piston, umbrella, disc, poppet, duckbill, ball, flapper, shuttle, gate, or other type of mechanism which functions as a valve to halt or redirect flow) which have at least one "open" state where fluid may pass, and a "closed" state where fluid may not pass. The flow controller, generically referenced as reference numeral 20, can use more than one type of valve or mechanism to control flow within, into, and out of the DDS and its catheters. The flow controller can also incorporate a pump to actuate a direction and/or magnitude of the fluid flow within, into, and out of the DDS. Accordingly, the term "flow controller" can include one or more valves and/or pumps. In an "open" state the flow controller may use several valves some of which are open and some of which are closed to direct fluid along a specific path, and accordingly the "open" state refers to whether a particular fluid path is "open", allowing fluid to pass or "closed", inhibiting fluid from passing. The flow controller can take the form of a "hub" structure which receives fluid from at least one source at its proximal port(s) and direct this fluid to one or more target paths through its distal ports. The number of proximal ports can be less than, equal to, or greater than the number of distal ports. One example of a flow controller which utilizes a hub type of structure is shown in FIG. 9. Depending upon the pumping operations of the DDS, the fluids can travel through the hub in a proximal-to-distal direction, or vice-versa (i.e., the flow control hubs can guide fluids bi-directionally). Flow controllers can be passive in that one fluid channel (e.g. a connection tube) can be continuously connected to several fluid channels (via, for example, a manifold), or can be active in that fluid path is dynamically determined by the state of one or more valves. Alternatively, the flow controller can control flow by exerting pressure upon the fluid channel (which may be a deformable, flexible, tube) in order to cause a specific portion to collapse, thereby halting flow.

The flow controllers of the DDS can be realized using different types of mechanisms which are described in the prior art and which are currently used in implantable pump devices. For example, US 2002/0193751 A1, incorporated herein by reference, discloses flow controllers, such as flow diverter or flow regulator based upon one of the following: a rod element, a pump, a solenoid, or a rotatable valve, which may or may not have a diversion conduit, a deformable conduit which may be squeezed shut by gas or hydraulic, pressure. However, in this art, these flow controllers are used to divert fluid in order to provide a simple mechanism for adjusting the rate of drug flow, rather than to halt flow, to send fluids to different catheter hubs thereby allowing different reservoirs to send fluid to different catheter hubs, and to isolate different fluids, as occurs in the DDS described here. U.S. Pat. No. 5,643,247, incorporated by reference herein, includes microparticle switching devices for stopping or redirecting flow, or for use as mechanical actuators or minipumps, and which can be used in the DDS, including the catheters (e.g., at either proximal and distal ends, and, for example, to accomplish inter-lumen flow control or circulation of a fluid circuit). The plurality of flow controllers 20 for the DDS is referred to collectively as a flow control system operated by the flow control module 22 as described herein.

The states of the flow controllers 20a, 20b can be determined by the control apparatus 22 or flow control module. Alternatively, rather than the state of the flow controllers 20a, 20b being controlled by the control apparatus 22, the state can be pressure sensitive, for example, the flow controller can enter an open state only when positive pressure on one side is more than a specified amount. This type of pressure sensitive control of the flow controller can not be used when a reservoir serves more than one catheter hub since operating the pumping means for a reservoir and creating a pressure increase would set flow controllers 20a, 20c for both catheter hubs 16a, 16b to their open states and controlled delivery of fluid from only one catheter would not be realizable (e.g., see FIG. 1c). The states of the flow controllers enable the DDS to route fluids within its internal components. For example, flow controllers 20a,b are operated by the control apparatus 22 to control the flow of fluids so that these may travel from each reservoir 14a,b to a specific catheter hub 16a. Flow controllers (e.g. 20r) also allow for the control of fluid flow during filling and refilling operations. Any set of mechanisms which enable the flow of fluid to be controlled so that it is encouraged or inhibited from flowing along one or more fluid paths is understood to be a fluid "flow controller". In the embodiment shown in FIG. 1a the fluid flow controller is realized by the control apparatus and the flow controllers whose states it determines in order to direct the flow of fluids along the different fluid channels of the drug delivery device DDS.

The DDS is filled in order to provide the fluid for subsequent drug delivery. At least one replenishment mechanism is incorporated into the DDS which serves to securely join with an external fluid source connector so that the DDS can be filled with fluids. In FIG. 1a, a replenishment mechanism is shown which is comprised of an inlet/input port 24 which resides in the housing 12, and which includes a re-sealable port 26 or "septum", which is designed to make a secure connection with an external fluid source connector (e.g., the septum may be punctured by catheter which terminates with a syringe). The inlet port 24 allows fluid to travel through the inlet port fluid channel 18r, when permitted by a flow controller 20r for regulating flow of fluid from the inlet port to internal components of the DDS (e.g. reservoirs 14a,b, channels 18a,b,r). In FIG. 1a the inlet port fluid channel 18r allows fluid to travel from the inlet port 24 to the catheter hub 16, although, alternatively, the port 24 can be connected by inlet port fluid channels 18r,18r' directly to one or more of the reservoirs 14a,b (e.g. see FIG. 1b) or to other internal components of the DDS. Additionally, several inlet ports 24a,b, inlet port fluid channels 18r,18s, and flow controllers 20r,s can allow for different fluids, that are dispensed through an external fluid source connector coupled between the fluid source and at least one of the inlet ports 24a,b, to be routed to different components of the DDS (e.g. see FIG. 1c). Further the DDS can have one type of replenishment mechanism that is configured for refilling the DDS prior to implantation, and another replenishment mechanism that is configured for refilling the DDS once it is implanted. Additionally, the DDS can have a replenishment mechanism that utilizes a multi-lumen catheter which is configured to be used with the DDS testing/calibration/refilling apparatus (both of which will be described). As is known in the art, the inlet port 24 can incorporate a membrane to filter the fluid entering the implantable drug delivery system.

At least one non-leaking reservoir (e.g. 14a) holds fluid that will be dispensed by the DDS. The reservoirs can be embodied in many ways. For example, each of the reservoirs can be lined with a balloon made from an elastic material and can utilize a plunger that collapses against one side of the balloon, in order to create a positive pressure that forces fluid to be dispensed, as is taught in the U.S. patent application Ser. No. 10/099,060 (the '060 application), incorporated by reference herein. At least one reservoir pump 23

(see FIG. 11) which is controlled by the control apparatus 22, can modify the positions of the plungers in order to control flow from one or more reservoirs. Alternatively, the reservoirs 14a-b can be realized using a dual chamber reservoir wherein a first chamber contains the infusate and another is pressurized with a gas or fluid which causes the infusate into or out of the first chamber under the control of the control apparatus 22, which utilizes the positive/negative pressure of the gas or fluid as pumps 23 for at least one reservoir. Other embodiments of the fluid containment means are also possible.

The pumps 23 for at least one reservoir 14a, as well as the other pumps of the DDS and its catheters, can be realized using a stepper motor, lead screw and anchored lead nut, as is taught in the '060 application. Additionally, the pumps can be realized through a piston, diaphragm, bellows, screw or other type of pump and can operate via hydraulic means, spring means, stored pressure, and many other means as are described in the prior art. The pumps 23 may be, for example, mechanical (e.g., spring powered or gas powered), electro-mechanical (e.g. screw type, hydraulic, piston, worm gear, peristaltic or displacement mechanisms, or pulley mechanism as described by, for example, U.S. Pat. No. 6,394,981, the "981" patent), or osmotic, where a valve under control of the control apparatus 22 may determine how much liquid is exposed to a swellable agent in order to adjust the amount of pressure imposed on a drug by the pump. The DDS may contain more than one type of pump 23 and more than one type of reservoir. Additionally, rather than having a separate pump 23 for each reservoir, one pump 23 can be used to accomplish the pumping operations for one or more reservoirs, for example, using a gear assembly. Although in FIG. 1a various components of the DDS (e.g., the reservoirs, pumps 23, or rechargeable power supply) are located inside the DDS housing 12, these can also be distributed so that some components are situated in separate locations that are easily accessed and that are external to the housing (such as in the CHCA and/or catheter 80—see FIGS. 7a,b,c,d and 8), as is described in U.S. Pat. No. 4,588,394, which is incorporated by reference herein. U.S. Pat. No. 6,551,235, incorporated by reference herein, shows an alternative to gear pumps, wherein a valveless pump consisting of a magnetically manipulated cylinder is used to pump fluid. Such a pump could be incorporated into the connection means and could be used to draw fluid from the reservoirs rather than, or in addition to, having the pumping means 23 exerting a positive pressure on the reservoirs. Valves which could be used in the pump are made by Lee Company, Westport, Conn. and can be, for example, a solenoid valve, latching solenoid valve, IMH orifice for liquids, or a VHS micro-dispense valve. Accordingly, it is recognized that pumps 23 and assorted valves of the flow control system are collectively referred to as flow controllers 20.

The control apparatus 22 controls the components of the DDS to achieve controlled flow of fluids used during drug delivery, for example, by independently activating the pumps 23 to cause increased or decreased pressure to be produced within any reservoir contained in the DDS and controlling fluid flow along specified paths. The control apparatus 22 can either communicate with pumps or, as occurs in many of the embodiments illustrated in the FIGs of this application, can contain the pumps for the reservoirs. The control apparatus 22 contains hardware/circuitry (which may run according to a software program) that allows the control apparatus 22 to control drug delivery, operate the DDS in its various modes, sense changes in the implantee, and achieve many of the other operations described herein. Alternatively, some of the functionality achieved by the components of FIG. 11 can be realized in the form of software which is executed by the processor 304. The control apparatus 22 also provides power to/controls/communicates with/pumps, sensors, and flow controls of the catheters. While the electrical wires and connections are not shown in the figures, to prevent cluttering of the figures, it is understood that electrical/hydraulic connection, which may be in the form of a wire/tube harness, connects the control apparatus 22 (and/or the power supply) to each of the components (e.g., pumps, sensors, flow controllers 20) that it controls in the DDS and its catheters 80.

Figure 11:
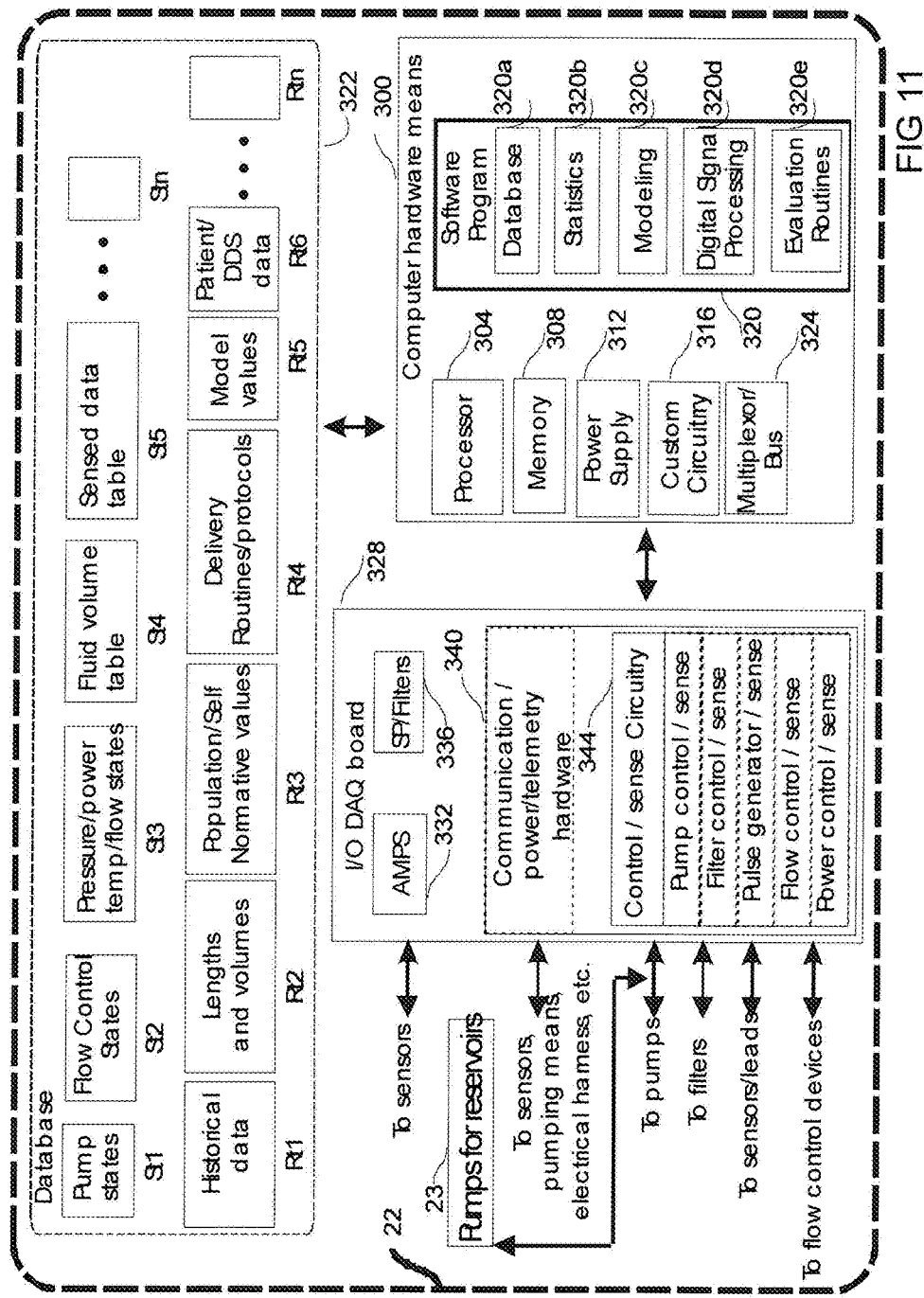
FIG. 11 is a block diagram of a preferred embodiment of the control apparatus of FIG. 10.
Figure 12:
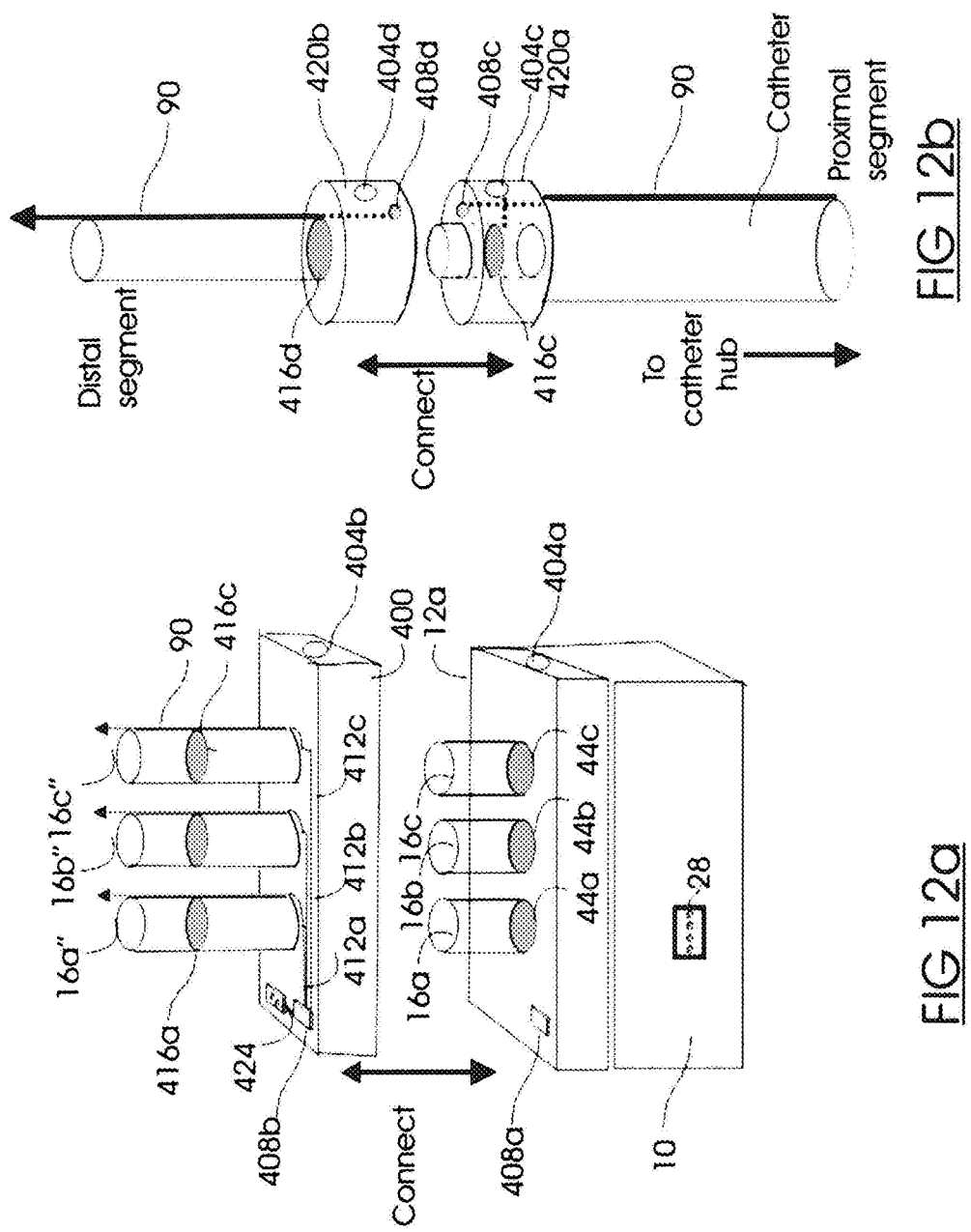

A preferred embodiment of the control apparatus 22 of FIGS. 1A-C is shown in FIG. 11. The control apparatus 22 includes sufficient computer hardware 300 for accomplishing its tasks. As is well known in the art, the computer hardware 300 includes, for example, components such as a processor 304 with a real-time clock, memory 308 (e.g., EEPROM, RAM, flash) for storing information such as delivery protocols or DDS events (e.g., activity, flow rates, sensor levels, etc.). The computer hardware 300 of control apparatus 22 includes, or is in functional contact with, a power supply 312, such as a rechargeable battery which provides the power needed to run the DDS. The computer hardware can also contain custom circuitry 316 which contains, for example, alarm circuitry which triggers an alarm when the software program 320 determines the DDS is malfunctioning. The software program 320 can exist in the memory 308 and can be loaded, modified and updated by the implantee, manufacturer, or medical personnel. The software program 320 enables the computer hardware 300 to perform all DDS operations and contains software subroutines or "modules". For example, modules of the software program 320 can include a database module 320a which includes a database 322 and associated routines for retrieving/storing/querying information in the database, a statistics module 320b for performing univariate and multivariate statistics upon data, or transforming the data into factor or discriminant scores (as has been previously described by the inventor in U.S. Pat. No. 6,066,163, and its related applications, incorporated by reference herein), a modeling module 320c for performing pharmacokinetic modeling, which can be based upon sensed data, or for performing modeling of pumping operations (e.g. in order to determine how the DDS operates to dispense a drug along a certain fluid path while taking into consideration the amounts and types of fluid already stored in that path). The modeling module 320c enables the software program 320 to run simulations of the DDS in order to accurately determine the drug delivery which will occur when the DDS components are operated according to a specific set of instructions and enables the creation of accurate, mathematical models of how fluid will flow within the physical drug delivery system. This is beneficial, for example, when the implantee's fluids at the tip of the catheter are flowing at a certain rate (and therefore exert a backflow pressure upon fluid to be dispensed) and/or the DDS regimen requires that the dispensed drug is of a specific concentration which is related to this rate (e.g. a flow sensor located in the intestine senses the rate of substances moving along the intestine and specified amount of drug is dispensed at two different locations in a manner that is related to this rate).

The digital signal processing (DSP) module 320d contains DSP routines for performing, for example, filtering, frequency analysis, and many other DSP routines as is known in the art. The evaluation routines module 320e contains routines for determining if a positive result has occurred, in which case drug will be dispensed according to a drug delivery regimen, or negative result has occurred, in which case no drug will be delivered. The evaluation routines module 320e can contain algorithms for evaluating the sensed data, such as, pattern recognition and template matching routines, and algorithms related to performing evaluation of, for example, whether sensed data meet, or fail to meet, threshold criteria or statistical criteria which can be univariate or multivariate. When the DDS contains electrical leads for providing electrical stimulation instead of, or in addition to, pharmacological stimulation the positive and negative results of the evaluation routines module 320e will similarly determine if electrical stimulation occurs. It is obvious that the software program 320 can contain additional software modules, or alternatively, may contain fewer modules and instead these modules can be either accomplished by analogous hardware, or can be located in the external patient controller which may execute its software routines much more quickly and without using power of the implanted DDS.

The computer hardware 300 of the control apparatus communicates with, and provides power to, the programmable input/output data acquisition hardware 328 (DAQ) via its multiplexor/bus hardware 324. The DAQ 328 contains circuitry which permits the control apparatus 22 to control, communicate, and/or provide power to all the other components of the DDS, its catheters, and external components such as remote sensors, the external patient controller, the pump tester/calibrator/filling apparatus (TCFA) accessory, and other components which may or may not be in direct physical contact with the DDS, but which can be used with the DDS to assist in drug delivery. The DAQ 328 contains amplifier circuitry 332 for amplifying data sensed at external sensors, for example, EMG activity. These signals can then be passed through signal processing/filtering circuitry 336 which may consist of hardware that is able to provide rapid or real-time signal processing and filtering of the sensed data. Additionally, some sensors may contain amplifying/filtering/signal processing circuitry within them and the components of the DAQ can act as a second stage of amplifying/processing or the sensors can communicate directly with input/communication channels of the DAQ hardware. Accordingly, the DAQ 328 also contains communications/power/telemetry hardware 340, for communicating with and providing power to the components of the DDS. For example, the control apparatus 22, can communicate with the external patient controller or external instrumentation that monitors information that is relevant to the drug therapy (e.g., a patient's heart rate), the TCFA, or with sensors which may be coupled to the catheters either through a direct physical link or through telemetry. The communications/power/telemetry hardware 340 can also allow for controlling and/or sensing the internal operations (e.g., pump movements), levels (e.g., fluid levels in reservoirs), and states (e.g., flow control states, pressure levels or flow rates) during DDS operation. The communications/power/telemetry hardware 340 can also connect to an electrical harness (although this is not shown in the figures to prevent cluttering of the figures) which provides an electrical/communication connection from the CA 22 to all other components of the DDS, and it should be understood that such a harness allows the DDS embodiments shown in, for example, FIGS. 1-3, to operate.

The control/sense circuitry 344 of the communications/power/telemetry hardware 340 also contains circuitry for controlling the states of the flow controllers of the catheters. The communications/power/telemetry hardware 340 further contains specialized control/sensing circuitry 344 which can contain multiplexors, communication hardware, and specialized control, processing, and sensing circuitry for controlling components and sensing information during pump operation. The control/sensing circuitry 344 which is configured to communicate with (e.g., receive information sent by, or send power and control commands to) sensors of the DDS. The control/sensing circuitry 344 contains pump control/sensing circuitry for achieving pumping operations, filter control/sensing circuitry for achieving filtering operations, pulse generator/sensing circuitry for stimulating electrical leads or sensing information from these leads, flow control/sensing circuitry for achieving flow control/sensing of the fluids during drug delivery operations, and power control/sensing circuitry for modulating and monitoring power usage related to the power supply 312. The control/sensing circuitry 344 may also have dedicated circuitry for processing data, for example, data that are sensed by external sensors located outside of the DDS housing 12 which may only be sent to the computer means when a specified condition is met. The control/sensing circuitry 344 can control/receive information from external sensors which can sense physiological, chemical, EKG, EEG, and other signals. In some embodiments, the external sensors are connected to the control apparatus via an external sensor/stimulator connection port 28 (e.g., see FIG. 1a). When the sensors are electrical, such as in the case of EEG, the control apparatus can also send stimulation signals out of external sensor/stimulator connection port 28 to the electrical sensor/stimulation lead.

The control apparatus 22 can activate the internal components of the DDS in a specified manner to achieve desired drug delivery. In the embodiment of the control apparatus 22 shown in FIG. 11, controlled delivery is made possible, in part, by the database software module 320a of the software program 320 of the control apparatus 22, which includes a database 322 having one or more tables containing information, termed "data". For example, the database can contain state tables ("Sts") which indicate current DDS characteristics, such as pump states St1 (e.g., positions) and flow control states (e.g., "open", "closed", or which of several "open states" is currently set to allow for various flow paths). A table of flow control states St2 provides the DDS to switch between different pumping modes and operations and permits the pump DDS to operate efficiently. For example, if a mode requires that a flow control be set to its open state and it is already in that state then time and energy are not wasted sending an additional command for the flow control to change to an open state. Additionally, the software program 320 can use the flow control state table St2 to monitor that the flow controls (e.g. 20a, 88) are in the correct states and are not malfunctioning or blocked. The state tables can also include pressure/power/temperature/flow state tables St3. For example, the pressure level tables can include intra-catheter pressure levels and pressure levels which exist outside of the DDS, in the implantee, and can be used in order to adjust pumping operations so that fluids are dispensed as intended by the drug delivery regimen. Further, the software program 320 loaded into the memory 308 and implemented by the processor 304 of the computer hardware 300 of the control apparatus 22 can periodically check the pressure/power/temperature/flow state tables St3 of database software module 320a to provide that the power supply 312 contains at least a specified amount of charge, and if not the processor 304 can send an alarm signal through the multiplexor/bus 324, to the communication/power/telemetry hardware 340 which transmits this signal to an external patient controller and warns the implantee that the DDS must be recharged. The state tables can also include a fluid volume table St4 which contains updated information about the amounts, concentrations, and types of fluids contained in the different reservoirs, catheters, catheter fluid circuits, and other components of the DDS.

Figure 8:
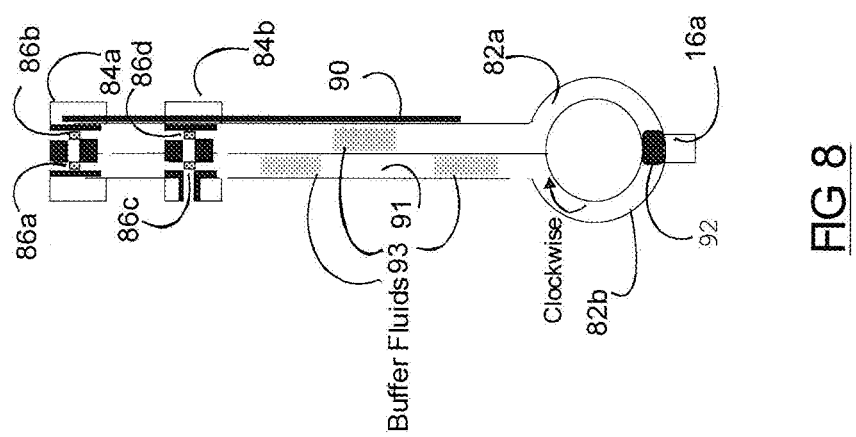
FIG. 8 shows the dual lumen catheter of FIG. 7a with a pump flow controller.

The information fluid volume table St4 can be used along with information in other tables, for example, by the modeling module 320c of the software program 320 to determine which DDS operations are necessary to cause flow within a fluid circuit (e.g., the drugs and buffer fluids which are circulated in the dual lumen catheter of FIG. 8) in order to cause a particular drug to flow so that it is adjacent to a flow controller (e.g., 86a of FIG. 8) which can dispense this drug to the implantee, and to then dispense a particular drug. The state tables can also include sensed data table St5 which can contain information such as the current concentration of a particular drug in a mixing chamber (e.g., 40 of FIG. 2), pressures and flow rates at the distal tip of the catheter or along the catheter, or the current estimate of the muscular tremor of an implantee which has been obtained by having the processor 304 use the digital signal processing software 320d to analyze a digital representation of sensed data is provided by the control/sense circuitry of the communication/power/telemetry hardware 340 of the DAQ board 328 after an EMG signal sensed by an EMG sensor has been amplified and filtered by amplifier hardware 332 and filter hardware 336. The information contained in the sensed data table can be used, for example, to determine if a drug in the mixing chamber 40 has reached a specified concentration as indicated by a sensor in the mixing chamber 40, or if additional diluent must be added. Other types of state tables can be included as well.

The database 322 can also contain a plurality of reference tables ("Rts") which hold reference information that is relevant to achieving a desired drug delivery or information related to past pump activity, information such as delivery routines and protocols used to deliver a particular treatment regimen, number of hours of use, amount of drug delivered between various dates, average power consumption, and other types of reference information. A historical data reference table Rt1 can include, for example, a record of all past sensed data, a partial record of past sensed data, statistical summaries of the characteristics of past sensed data, and a record of pump events. Pump events can include general records of delivering drugs, their amounts and the times of delivery, and specific records which can include all DDS operations such as activating a pump or opening a flow control. A lengths and volumes reference table Rt2 can contain information about the physical dimensions of various DDS components, such as the lengths and volumes of the catheters which were implanted in the implantee. A population/self normative values table Rt3 can contain population norms appropriate for the age/sex/weight of the implantee (and of the fetus if the DDS is used for treatment of a fetus). This table can contain normative values for sensed information that is, for example, sensed by external sensors (or sensed by external instrumentation and sent, via telemetry to the DDS) such as tissue state, pressure levels, concentration levels of drugs, metabolites, and chemicals present in the implantee which can further be qualified in terms levels which existed at specific times before, after, or during prior deliveries. This table can also contain normative values for subjective measures inputted by an implantee using an external controller. A delivery routines/protocols table Rt4 can contain information related to dispensing drugs according to different treatment regimens. A model values table Rt5 contains information related to pharmacokinetic modeling of the implantee. Models can be based upon normative values or can incorporate values sensed by the sensors of the DDS. A patient/pump reference table Rt6 can contain information about the bodyweight and age of the implantee, and information about the DDS such as serial numbers of components, DDS identification numbers, software program ID and version number, the viscosities and types of fluids contained in the DDS. Other types of reference tables can be included as well. The values in the database 322 can be accessed or updated by the software program 320, loaded into the memory 308 of the computer means 320. The database module 320a and the database 322 can also be realized partially or completely in hardware rather than software form. An illustrative example of how the control apparatus 22 may perform drug delivery by using the database is as follows:

i) the software program 320 uses the database module 320a to check the delivery routines/protocols table Rt4 of the database 322 and determines that sensing is to occur at a particular sensor ii) Sensing causes the sensed data to be updated in the sensed data table St5 iii) according to the evaluation routines module 320e which compares the sensed data to a self normative value contained in the population/self normative values table Rt5, via the statistics module 320b, a positive result has occurred and drug must be dispensed iv) the software program 320 determines that a particular drug at a particular concentration must be delivered from a specific catheter hub 16a, refers to the fluid volume table St4 and determines both that the fluid to be delivered is in Res1 14a and also that there is only buffer fluid in the catheter attached to that hub 16a, and then refers to the lengths and volumes table Rt2 to determine how much fluid must be dispensed in order for a desired amount of drug to be dispensed from the tip of the catheter v) the software program 320 then operates the computer hardware 300 to cause the necessary flow controllers 20a, 20b to be set to the correct states (e.g., 20a set to open state, 20b set to closed state) and operates the pump 23 for Res1 in order to cause the fluid to be delivered to the implantee.

As reflected in this example, in order to deliver a drug out of a specific catheter the DDS the software program 320 of the control apparatus 22 can use information held in its database 322 in order to provide appropriate control operations for its internal components. The software program 320 and information contained in its database 322 is used to control the flow of fluid in the DDS by manipulating the internal components of the DDS, such as by changing the state of the flow controllers 20 as different pumps are activated, and thereby permitting fluids to be dispensed from one or more reservoirs to one or more catheters at specified concentrations and rates.

The communication/power/telemetry hardware 340 of the control apparatus 22 allows the DDS to communicate with external instrumentation that is often used in conjunction with implanted devices, such as a specialized computer or an external patient controller. The communication/power/telemetry hardware 340 can contain an alarm warning which can activate an auditory, visual, or vibratory warning (in the DDS or the external controller), and can transmit a signal through the internet or phone or over a wireless connection (e.g. via the external controller). The communication/power/telemetry hardware 340 facilitates the external instrumentation to modify the DDS operation and drug treatment (e.g., allows for patients or medical personal to program the DDS or allows for patients to administer or change a dose) and facilitates other operations which respond to patient commands, allows setting of routines and regimens of drug administration, and allows the DDS to deliver drugs in response to sensed data, for example, to create closed-loop drug delivery. The communication/power/telemetry hardware 340 also facilitates data to be sent to the external instrumentation which can perform operations such as signal processing on such data. Such data may be, for example, biological, chemical, physiological measures recorded from the patient, or summaries, statistics, transformations of these measures such as PCA factors or discriminant scores.

The control apparatus 22 works according to data relevant for different drug delivery regimens which are stored in the delivery routines/protocols tables Rt4 of its database 322 of the DDS, and which may cause predetermined amounts of fluids to be dispensed at specified rates, for predetermined amount of times, and in pre-determined patterns (e.g., a continuous rate, large bolus, small bolus, repeated small bolus doses delivered in a rapid or slow manner, etc.). For example, U.S. Pat. No. 6,475,180 (the '180 patent), describes several delivery modes, such as a basal rate delivery which also allows for patient controlled delivery to be periodically superimposed, repeatable constant doses, constant rate, allows for switching from one mode to another, and describes a drug pump which can perform internal self tests and calibration operations. Further the '180 patent describes an external patient controller which can communicate with external instrumentation and measurement means that can include temperature sensors, blood pressure sensor, EKG monitor, or EEG monitor.

The drug delivery device DDS of FIG. 1*a* delivers drugs in response to the sensed data. Sensors can be located both internal to and external to the DDS's housing 12. Internal sensors can include, for example, power sensors for the rechargeable battery, air/gas detectors, pressure, level, and temperature sensors, motor position sensors. External sensors can sense concentrations and chemicals which exist in external fluids that are located in different areas of the body of the implantee, as well as temperature, physiological processes such as EKG/EEG, etc. Data, sensed by these sensors can be analyzed by the computer 300 of the DDS or can be sent to the external patient controller for analysis. The patient can also input subjective experiences such as being nauseous.

The DDS can provide the external patient controller (e.g. the TCFA of FIG. 10) with DDS component information about how much drug is left, can provide a log of usage (e.g., a rate of use calculated as a percentage of total drug at start) and related information such as amount of power used to accomplish various types of drug delivery, amount of pressure required to deliver drug, etc, and can issue warnings to the user, which alert the user to problems or potential future problems which may occur, such as lack of power or drug. For example, the control apparatus 22 can sense data from pressure detectors, which can serve to function as occlusion detectors, which detect when flow is blocked, for example when a dedicated circuit determines pressure is above a specified threshold level. The DDS can automatically modify, or allow the patient to modify via the external patient controller, a previous delivery regimen based upon recent trends in the history of the implantee in order to compensate for variations in the implantee's schedule. One example of this is a "time shifting" the drug delivery regimen where a regimen is shifted forward or backward in time. For example, if the control apparatus determines that, over the last 4 days, an implantee has gone to sleep 6 hours earlier than for the previous 2 weeks by analyzing the sensed EEG data, as may occur when an implantee travels from Europe to America, it may adjust the drug regimen accordingly or propose such an adjustment to the user. The delivery regimen can be proactive, and base its delivery regimen on a historical pattern of delivery which it then shifts in time. For example, it could use the average pattern of delivery over the last 5 days to determine pattern of delivery for the sixth day, but shift the cycle forward by ½ an hour. This would be beneficial, for example, when a drug is more effective when given 1 hour before a meal rather than in response physiological changes that occur due to that meal. In other words the DDS can be programmed to calculate the average drug delivery protocol over a short period such as a week, and then shift the protocol forward or backward in time to obtain desired results.

Drug delivery is also improved by enabling the DDS (by means of either the control apparatus 22 or external patient controller) to provide an estimate of, or warning based upon, the amount of time which the remaining drug will last which can be calculated using prior usage patterns or level indices. The DDS can use its sensors and tables to generate level indices. Level indices refer to the amount of drug, buffer, or diluent which exists in the DDS at the current time. An absolute level index refers to the amount of drug, buffer, or diluent which is contained within components of the DDS such as 1 or more reservoirs or catheters or both. Unlike the prior art the DDS can also use predicted level indices. Absolute level indices can be adequate when a DDS does not dilute drugs or use buffer fluids since the volume of drug in the reservoirs 14*a,b* is equivalent to, rather than directly related to, the amount of drug which can still be dispensed. A predicted level index refers to the amount of drug, buffer, or diluent which is contained within components of the DDS within the context of the drug delivery regimen, lengths of the catheters, and other relevant variables. For example, if the buffer fluid is used to push a drug through the length of a 100 millimeter catheter having a fluid volume of 1.5 ml and there are 4.1 ml of buffer fluid left in the reservoir, then even though there is a substantial amount of buffer fluid left, there is only enough for 2 more deliveries of the drug. Additionally, in the case of a drug which is diluted by a diluent in order to obtain a desired concentration for delivery, the absolute amount of drug is only meaningfully interpreted using information about the concentration of the stored drug, the concentration of the drug that is to be delivered to the patient, and the rate at which it is to be delivered. Predicted level indices therefore use information about such factors as the stored drug concentration, concentration needed during drug delivery, past patterns of delivery, future demands of delivery for a particular regimen, volumes of the components of the DDS, such as the length (volume) of one or more catheters, and other related factors which may affect the functional amount of fluids stored within the DDS. Predicted level indices can include guardbands based upon the variance of past patterns of delivery which occur due to variation in a patient's needs. Predicted level indices can include estimates of the amount of drug remaining and can be translated into units that are meaningful to the patient, such as 'number of deliveries, which are possible using remaining fluid levels', or 'amount of time before specific fluids are used up or reach a specified level'. 'Low reserve' warnings can be triggered by one or more drug level indices and are transmitted by the DDS to the patient controller to warn the implantee. US 20020087113 describes a drug management module for determining whether the drug should be replenished based upon the drug usage information which is based upon absolute measures of drug in the drug delivery system. The drug management module of this prior art DDS does not use predicted level indices which incorporate information related to dilution and final concentrations of delivered drugs or the use of buffer fluids.

The control apparatus 22 of the DDS controls all operations of the DDS that are required during operation and maintenance. For example, due to the software program 320 that has been uploaded into the computer hardware 300, the processor checks the real-time clock and determines that a specified amount of time has elapsed since the last sensing operation occurred. For example, the processor 304 reads the measurement of a chemical sensor which senses glucose level and determines that the reading is above a pre-specified level. According to the software 320, the control apparatus 22 causes a specified amount of insulin to be dispensed by activating the pumping means for Res1 14a while setting the flow controller 20a for Res1 14a into an open state. The movement of the pump 23 causes a warning to be generated because data for the Res1 14a kept in the fluid volume table St4 indicates that the reservoir is diminished below a specified level. The telemetry circuitry of the control apparatus 22 sends a signal to an external controller indicating that Res1 is low and will need to be replenished.

The implantable DDS 10 of FIG. 1a provides for the fluids in the separate reservoirs to be sent into a particular catheter, and moreover this is accomplished while inhibiting inadvertent mixture of fluids. The independently operated flow controllers of Res1 14a and Res2 14b assist in this advantage (e.g., the fluid from Res1 14a is inhibited from entering into the connection means of Res2 14b when its flow controller is in a closed state). For example, if there were no flow controllers, then when the pumping means of the DDS were not operating, fluid from the catheter could enter either connection tube and even begin to mix with the fluid in the reservoirs (further, drugs that are held in reservoirs at higher concentrations could diffuse to fluids held in the connection tube or catheter). When using dilution and buffer fluids, issues of diffusion and osmosis become much more relevant and flow controllers 20 act to form a seal between fluids which contain different concentrations of one or more solutes. Setting the flow controllers 20 to a closed state while the pump is not active can decrease this risk. Additionally, during operation, if the fluid of Res1 14a is being pumped at a different rate, e.g. twice as fast, as the fluid being pumped from Res2 14b, then the fluid from Res1 14a could provide resistance to the fluid in Res2 14b and decrease the accuracy of the amount that enters the catheter. Further, for some purposes, the drugs kept in the first and second reservoirs 14a,b should not be mixed until administration to the patient. The DDS can allow for this. For example, by operating the implantable drug delivery system 10 according to a sequential activation subroutine of the software program, the accuracy of drug administration can be increased and drugs in the two reservoirs are not mixed until they are dispensed into the catheter hub 16. The sequential activation subroutine can cause the control apparatus to sequentially alternate the state of the flow controllers 20a,b while simultaneously sequentially activating (or alternating) the pump for the first and second reservoirs 14a,b.

The embodiments shown in FIGS. 1b-13 contain components which are very similar or identical to those shown in FIG. 1a. Accordingly, the same reference numerals have been used for the corresponding components.

In the embodiment of the DDS 10 shown in FIG. 1b, the DDS 10 includes many of the same components as in FIG. 1a, but also permits fluid from the implantee's body to be drawn upon to refill a reservoir, in this case Res2 14b. Accordingly, the Res2 14b contains an inflow fluid channel which may consist of inflow catheter 30 which permits fluid to travel from outside the DDS housing into Res2 14b. The inflow catheter 30 may have a filter 34 on its distal tip, which may be a semi-permeable membrane. Additionally, the inflow catheter is coupled to a filter 25 so that fluid in the inflow catheter 30 can flow into an input port of the filter 25 when flow control 20k is set to an open position which directs flow into the filter 25 (and does not permit flow to continue more proximally in the inflow catheter 30) and out of an output port of the filter 25 and into Res2 14b when flow control 20n is set to an open position. The filter 25 may have its own pump which is under control of the control apparatus 22 or can rely upon the pump 23 of Res2 14b to cause fluid to flow through it. As will be described, the filter 25 can rely upon physical, chemical, or other modes of filtering to filter fluids drawn into the DDS. The proximal tip of the inflow catheter 30 has an inflow flow controller 32 which is under the control of the control apparatus 22. When operating the DDS according to some of the delivery regimens, the states of the flow controllers 20b, 32 are set so that fluid drawn into the DDS is routed out to the catheter hub 16 rather than back out of the inflow catheter 30. For example, the inflow flow controller 32 is set to a closed position, which does not permit fluid to pass, while the flow controller 20b for Res2 14b is set in an open position which allows fluid to flow into the catheter hub 16. The pump 23 for the reservoir is then operated in a forward position which causes fluid to leave the reservoir, travel through the catheter connection means and reach the catheter hub 16. Drugs from other reservoirs can be mixed with this fluid in the catheter hub 16. When the DDS is operated in one embodiment of the "implantee replenishment mode" fluid from the implantee is drawn into the inflow catheter 30 and then used to dispense drug. For example, the following steps could occur. The inflow flow controller 32 is set in an open position, which permits fluid to pass, while the flow controller 20b for the Res2 14b is set in a closed position which does not allow fluid to pass. The pump 23 for Res2 14b is then operated in a reverse direction (to create a "negative/suction pressure" or "vacuum") which causes a human fluid, for example, gastric juices of the stomach such as bile, to enter the Res2 14b from an external source, for example, the stomach, liver, pancreas, small intestine, colon, gallbladder or other part of the digestive system. Instead of being functionally connected to a reservoir, e.g., Res2 14b, in an alternative embodiment (not shown) the inflow catheter 30 can simply be connected to the catheter hub 16 by a fluid channel which has a pump and which may also have at least one flow controller in order to route fluids from the implantee directly into the catheter hub. The DDS of FIG. 1b, is also different from FIG. 1a, in that it contains an inlet port 24 which is connected to Res1 and Res2 by inlet port fluid channels 18r and 18r' respectively, which use flow controllers 20r and 20r'.

When the implanted drug delivery DDS is used to treat disorders of the digestive system, the drugs which may be held in other reservoirs 14a,b can be, for example, appropriate analogues or regulators of gastrin, secretin, motelin, insulin, acetylcholine, adrenaline, or cholecystokinin (CCK) or may be nutrients, proteins, vitamins, antacids, enzymes, or other substances. Two types of nerves (extrinsic and intrinsic) help to control the action of the digestive system. Extrinsic nerves come to the digestive organs from the unconscious part of the brain or from the spinal cord. They release acetylcholine, which causes the muscles of the digestive organs to contract, and adrenaline which causes the stomach and pancreas to modulate (e.g., increase) production of digestive juice. Adrenaline also relaxes the muscle of the stomach and intestine and decreases the flow of blood to these organs. Accordingly, the DDS can, for example, use these two substances to modulate muscle activity in an acute, chronic, tonic, or sequential manner (e.g., as in the case of mimicking peristalsis along distributed musculature).

When the implanted DDS is used to treat disorders of the CNS, the human fluid can be the cerebral spinal fluid (CSF), and the drugs can be, for example, appropriate synthetic analogs or regulators of substances found in the CSF or in the brain such as neurotransmitters. When the implanted system is used to treat the spinal column or joints, the human fluid is, for example, synovial fluid, and the drugs which are held in the other reservoirs are, for example, analgesics, anti-inflammatory drugs, antihistamines, or other drugs appropriate to treating a disorder. The implanted system can be used, for example, to provide analgesia, chemotherapy, treatment of tumors, medical or nutritional treatment. The implanted system can also be replenished by other fluids found in the human body such as interstitial fluid, water, urine, blood, lymph, serum, plasma, amniotic fluid, breastmilk, synovial fluid and spinal fluid, CSF, and extracellular fluid, and the targets for therapy can be any organ, set of organs, or area in the human body. In the embodiment shown in FIG. 1b, the fluid channel 18a for Res1 14a terminates more distally within the catheter hub 16 than the fluid channel 18b of Res2 14b, and a catheter hub division 36 containing a catheter hub flow controller 38 is located between the locations where the fluid channels 18a and 18b connect to the catheter hub 16. In one method of performing the Sequential Bolus mode the drug from Res#1 14a is loaded first into the catheter hub 16 and then the fluid from Res#2 14b is used to push the drug through the length of the catheter to the target site of the patient.

The DDS can be used for diluting a drug kept within the pump or for delivering a small amount of drug to a distal target, or for inhibiting residual drug remaining in a catheter due to prior drug delivery, which occurs when sending different drugs from the same catheter.

In another embodiment of the DDS, two or more reservoirs 14a,b are able to provide different fluids to two or more catheter hubs 16 (output ports) by relying upon fluid channels and flow controllers 20 which are under control of the control apparatus 22. In FIG. 1c, the implantable DDS 10 includes many of the components of the system shown in FIG. 1a, and in addition to a first catheter hub 16a, there is now a second catheter hub 16b. Although not shown, each of the catheter hubs can be functionally connected to one or more mixing chambers rather than being directly connected to the fluid channels. Also, although these are not shown, a catheter #1 is understood to be connected to catheter hub 16a, a catheter #2 is understood to be connected to catheter hub 16b, and so on. The fluid channels connect the reservoirs to the first and second catheter hubs 16a,b which, in this example, is achieved by connection tubes 18a, 18b, 18c, and 18d, where connection tube 18c connects the Res1 14a to the second catheter hub 16b, and connection tube 18b connects the Res2 14b to the first catheter hub 16a. The Res2 14b is also connected to the catheter hub 16b by a fluid channel, which in this case is a connection tube 18d. Two inlet ports 24a,b are shown in this embodiment, each connected to a separate reservoir using different inlet port fluid channels 18r,s and flow controllers 20r,s.

If fluids are to be sent out of catheters 1 and 2, then the pumps 23 must pump about twice as much fluid volume compared to when the fluid only is dispensed out of one of the catheters (assuming catheters have similar volume). Accordingly, the control apparatus 22 controls the pumps 23 of the reservoirs 14a,14b to provide the fluid which is to be delivered, and modifies the state of the associated flow controls 20, to deliver drugs from one or more catheters according to a drug regimen. For example, if simultaneous delivery is necessary, and the drug regimen requires that 0.4 ml of fluid from each of Rest and Res2 must be sent through catheter 1 and 0.8 ml of fluid from each of Rest and Res2 must be sent through catheter 2, then the pumps 23 which serve reservoirs 1 and 2 are operated to deliver 2.4 ml (0.8 ml of fluid, and 1.6 ml of fluid to catheters 1 and 2, respectively) and flow controllers 20a and 20b are set in the open state for ½ the time that flow controllers 20c and 20d are set in the open state. The implanted drug delivery system of FIG. 1c may contain two or more catheters and two or more reservoirs, and the control apparatus can control both the pumps 23 and the flow controllers 20 in order to specifically route the desired amount of fluid contained in each reservoir 14a,b to the specified catheter via the output ports 16. The DDS can also operate its flow controllers 20 and pumps 23 in a sequential manner in order to deliver different amounts of fluids to each reservoir 14a,b from the input ports 24a,b. The DDS of FIG. 1C could also contain additional reservoirs 14a,b which contain drugs, diluents, or buffer fluids. It is recognized that the pumps 23 can be considered as a type of flow controller 20 of the flow control system.

The use of a diluents and buffer fluids reduce the volume needed for drug storage since the drugs can be highly concentrated. Accordingly, the diluent(s) can utilize the majority (e.g., 70%) of the storage space while the drugs require only, for example, 30%. If one substance is used more than the others, the limiting factor is the amount of diluent rather than any of the particular drugs, which may normally each reside in equally sized chamber areas. For example if drugs A, B, and C each required 33% of the internal capacity, but the user required mostly drug A over an extended period, then drug A would be depleted faster than drugs B and C, requiring its refilling. By storing a highly concentrated form of drug A, B and C, and using a diluent, the limiting factor may become the diluent, which resides in 70% of the storage space, thereby allowing for greater amount of use prior to refilling. The use of a diluent also enables various concentrations of a drug to be dynamically created as needed. The use of a diluent also enables the amount of drug released to be only partially dependent on the volume of fluid released, since concentration or volume or both can be modulated.

In FIG. 2, a partial view of an exemplary embodiment of the implantable DDS 10 is shown in which a mixing chamber 40 enables the fluids from various reservoirs 14a,b to be mixed together, prior to their entrance into the catheter hub 16a. Although not shown in this figure, the mixing chamber 40 may have two or more compartments, flow controllers 20 between these compartments (may include pumps), and stirring or vibrating mechanisms, in order to assist in drug mixing operations (e.g., see FIG. 4). In the illustrative embodiment the fluid containment means are realized using five reservoirs 14a-14e, each having its own fluid channels, which are connection tubes 42a-42e that lead to the mixing chamber 40. Reservoir flow controllers 20a-

20e work in conjunction with the control apparatus 22 and pumps 23 of the reservoirs 14a-14e to enable the desired amounts of fluids from reservoirs 14a-14e to enter the mixing chamber 40. The reservoirs 14a-14e can all be the same size or can be different sizes. For example, the reservoirs which hold very concentrated levels of a drug may be relatively small and reservoirs which hold pusher fluids or diluents may be relatively larger. A catheter hub flow controller 44, which is under the control of the control apparatus 22, may also be provided in order to restrict fluid in the catheter from entering into the mixing chamber 40 and to prohibit fluid from the mixing chamber from traveling through the catheter hub 16 and entering into the catheter prior to delivery of a drug as dictated by a drug treatment regimen. A sensor 21, which sends sensed data to the control apparatus 22 of the DDS may be located in the mixing chamber 40 to sense characteristics of fluids, such as the concentrations of drugs being mixed in the mixing chamber 40.

In FIG. 3, a partial view of one embodiment of a DDS 10 is shown in which a first 16a and second 16b catheter hub is each attached to a mixing chamber 40a, and a third catheter hub is attached to a third catheter. Each mixing chamber 40a-b is connected to all of the reservoirs 14a-14c in the DDS. Alternatively, not all reservoirs may be attached to each of the mixing chambers 40a-b. Further, the number of mixing chambers, reservoirs, and catheters can be more than or less than that which are shown in FIG. 3. Accordingly, as is shown in FIG. 3, more than one catheter hub 16a,b can be connected to a single mixing chamber 40a. Each catheter hub that is attached to a mixing chamber will have its own catheter hub flow controller 44a-c (part of the generic flow controllers 20). Although not shown in this figure, the mixing chamber may have two or more compartments, flow controllers 20 between these compartments and pumps which operates under control of the control apparatus 22, sensors for sensing pressure, presence of gas, or drug concentration, and stirring or vibrating mechanisms, in order to assist in drug mixing operations (e.g., see FIG. 4).

Operational Modes

The DDS may operate in several operational modes including, but not limited to, the following: a Continuous mode, a Bolus mode, a "Sequential Bolus" mode, a "Flow-Return" mode, a "Flow-circulation" mode, a "Replenishment" mode, an "Implantee Replenishment mode", a "Sample-Push" mode, a "Filter" mode, a "Purging" mode, and a "Shunt" mode.

The Continuous mode and Bolus mode are where drugs are dispensed continuously, or at specific times, respectively. The Bolus drug delivery may occur according to many strategies, such as at least one of the following: in response to sensed data, in response to user commands, according to a specific chronological time, and according to a drug regimen.

One embodiment of the system and method of the current invention, as shown in FIG. 1a, allows the delivery variable concentrations of a drug and functions by using drugs at a high concentration and a diluent which are both output from the DDS simultaneously, at rates which produce the desired concentration. For example, if a continuous infusion of Drug A at a concentration of 9 mg/ml is desired, and Res1 14a contains a concentration of Drug A at 9 mg/ml, then only Res1 need be activated. However, if a concentration of 4.5 mg/ml is desired then the DDS system can dispense Drug A from Res1 14a at rate R, and a diluent from Res2 14b reservoir at rate R. If 3 mg/ml is desired the Drug A is dispensed at rate R and the diluent is dispensed at rate 2R. In this manner, the desired concentration of a drug can be dispensed by the DDS. An implantable DDS 10 which contains a system and method for delivering variable dosing of a drug may comprise a Res1 14a which is filled with at least the maximum concentration of a drug which is to be dispensed by the DDS to the patient. A Res2 14b contains a diluent, which may be an inert substance, which can be used to dilute the drug of the Res1 14a to the desired concentration. The control apparatus can control the pumping means and the flow controllers so that the drug and the diluent are dispensed simultaneously or in an interleaving fashion where the two substances are allowed to mix within the catheter.

In Sequential Bolus mode, a drug bolus is pushed from the DDS through the catheter attached to the output port 16 by a buffer fluid. The buffer fluids can be for example, a drug, a fluid that enhances the effects of a drug or the metabolism of a drug (i.e., an adjuvant), a nutrient, or a neutral/inert fluid, and may be primarily or totally miscible or non-miscible. Preferably the buffer fluid is an inert fluid that is mostly non-miscible with respect to the drug(s), so that it does not dilute the drug(s). If the buffer fluid is non-miscible with respect to one or more drugs, then one of the other reservoirs can be filled with a diluent so that various concentrations of drugs can be created prior to bolus delivery. The Sequential Bolus mode allows the DDS to deliver one or more drugs, and/or different concentrations of a particular drug in an exact bolus manner through at least a single lumen of the catheter to help inhibit problems created by "residual fluid" which is in the catheter due to prior dispensing of a drug.

The DDS can operate in a Sequential Bolus mode that can be helpful, for example, when more than one drug is dispensed through a specific catheter. In one method, this is achieved using the mixing chamber 40 (e.g., see FIG. 4) that allows a buffer fluid to enter the catheter "behind" the drug and thereby push the drug through the catheter. For example, the mixing chamber is first filled with the desired mixture of drugs from the reservoirs 14a,b. Subsequent to the filling of the mixing chamber, the catheter hub flow controller 44 is set to its open state, and flow controller which may be a plunger 46 attached to a pump 48 of the mixing chamber 40 is operated to cause the plunger 46 to push the drug through the catheter hub 16 and into a catheter (in the figure, the pump 48 is realized using a rod attached to the DDS pump 23, which, together with the plunger 46, provides as a volume adjustment mechanism for the mixing chamber 40). The catheter hub flow controller 44 is set to its closed state and the associated pump of the mixing chamber 40 is then operated in reverse direction as a buffer fluid in one of the reservoirs is pumped into it. The catheter hub flow controller 44 is then set again to its open state, and the pump is operated to push the drug mixture through the catheter into the desired target area. This mixing pump functionality can also be supplied by the DDS pumps 23. Alternatively, the Sequential Bolus mode can be accomplished using only the catheter hub (e.g., see FIGS. 1a & 1b), where the drug is pumped into the catheter hub first and then the buffer fluid is pumped through the same catheter hub. The Sequential Bolus mode can address the issue of residual drug in the catheter. In the drug delivery pumps of the prior art, a certain amount of drug from prior drug delivery will often be contained in the catheters and other areas of the implanted drug delivery system that contain fluid (internal components such as the catheter hub). The area in which this "residual fluid" resides is termed "dead space". For the DDS, when the buffer fluid is used to push the drug through the catheter, then the next drug can be delivered by the same catheter merely by pumping the buffer fluid and drug through the catheter and displacing inert buffer fluid used during the previous administration. If drug, rather than inert fluid, was the residual fluid contained in the catheter, then it would be necessary to eliminate this (e.g., deliver this fluid) prior to the new drug being delivered, and this might cause unwanted effects in the implantee. For example, the first drug (from the prior delivery) might act to increase heart rate, and the second drug might decrease heart rate. If the second drug can only be delivered by pushing the residual amounts of first drug out of the catheter, then delivery of the second drug, would functionally act to increase, and then decrease, the heart rate rather then just decreasing heart rate. It is also recognized that the DDS components, as controlled by the CA 22, can manage the flow of buffer fluids internally in order to assist in the return of unused drug fluids to their respective reservoirs 14.

By using a Sequential Bolus mode, where the drug is pushed through the catheter by a buffer fluid, the problem of unused drug in the catheter is addressed. This problem of residual fluid can also be addressed using a Flow-Return mode. The Sequential Bolus mode, or other drug delivery mode, can be operated in conjunction with a Flow-Return mode in order to provide for further advantage over the prior art. In the Flow-Return mode either a buffer fluid or a drug used during a previous drug delivery is drawn back into the DDS (e.g., back into the reservoir 14 from which it originally resided) in order to clear the catheter, and/or other areas of the drug delivery system DDS (e.g., the mixing chamber 40), from the residual fluid which was not dispensed during that previous delivery. Further, by using a Flow-Return mode, without the Sequential Bolus mode, the drug can be pumped out of the reservoir 14 until the required amount is delivered and then the remaining drug in the catheter is drawn into the reservoir 14 by operating the pump 23 and flow controllers 20 to cause the fluid to flow back into the designated reservoir 14. As in the case of the other modes available in the DDS, the Flow-Return mode can be aided by special catheter 80 designs as will be illustrated in FIGS. 7*a-d*.

When the Flow-Return mode is used with the special catheter 80 designs, and other modes, drug delivery performance can be greatly improved. A "Flow-Circulation" mode can be used with, for example, either a single lumen catheter 80 which is connected at both ends to the DDS in order to form a fluid circuit or "loop", or using a multi-lumen catheter 80 (e.g., FIG. 8). The fluid circuit can contain a sequence of drugs separated by buffer fluids. The drugs and buffer fluids can be circulated within the catheter 80 until the specific drug required for the present delivery operation is adjacent to a region from which it is to be dispensed (e.g., the catheter tip region). This circulation can be achieved using the pump 23 of either the reservoirs 14 or mixing chambers 40 (other pump controllers 20) of the DDS, or can be achieved using a catheter pump 92 as will be discussed (e.g., FIG. 8). The flow controls 20 located in the catheter 80 are then operated by the CA 22 of the DDS so that when the pump flow controllers 20 of the DDS are operated, and the correct flow controllers 20 are set to their open state, a specific drug is delivered. The Flow-Circulation mode causes drugs and buffer fluids to circulate in the lumen 82*a,b* of the catheter 80, but this mode can also be used with the Flow-Return mode to cause these fluids to be drawn back into the fluid reservoirs 14*a,b* of the DDS. Using an internal fluid circuit of the catheter lumens 82*a,b* provides for both residual buffer fluids and residual drugs which have been pumped into the multi-lumen catheter 80 from previous delivery may be re-used (or re-stored in the DDS) rather than interfering with subsequent drug delivery. This also enables the buffer fluids to be used more efficiently since less fluid is used to deliver a specific drug from the catheter 80. In order to operate the Flow-Circulation mode effectively, the database of the control apparatus 22 must have an accurate model which consists of information, such as information about the fluid circuit, its sequence of drugs and/or buffer fluids, the volumes of these fluids, the catheter volume and length, and the flow controllers 20 and other means by which the fluids are delivered.

The implantable DDS can operate in a Replenishment mode. In the Replenishment mode, fluids from outside of the body of the implantee are used to fill the drug-delivery DDS so that these can serve as a drug, buffer fluid or diluent during treatment. When multiple reservoirs 14*a,b* are included, the external drugs are routed to the correct reservoir. By operating the internal components of the DDS (e.g., the flow controllers 20) in a coordinated manner these external fluids can be guided into appropriate reservoirs 14*a,b*. For example, the medical personnel can use an external patient controller (not shown) operatively coupled to the DDS to send commands to the CA 22 which cause the fluids that he or she provides in the fluid source to be guided into the correct reservoirs 14. A further example of a type of external patient controller is the pump tester/calibrator/filling apparatus (TCFA) accessory. One embodiment of the DDS and the external patient controller uses a fluid delivery tube to route fluid to the input port 24 of the DDS. During the refilling procedure, a specific drug is made available to the input port 24 and flow controllers 20 in the inlet port 24 act as the routing mechanism which provides that the drug flows to the targeted reservoir (e.g. 14*a* from the inlet port 24 and the drug fluid is inhibited from flowing into the other reservoirs (e.g., 14*b*) connected to the inlet port 24 by keeping the flow controllers 20 for these other reservoirs 14*b* in their closed state. Additionally, the internal pumping flow controllers 20 and external refilling instrumentation of the TCFA can operate together to decrease the risk that negative and positive pressure levels exceed specified ranges and also to ensure that the pressure levels in the fluid pathways and reservoirs 14 of the DDS, which might cause unwanted effects, are minimized (e.g., to ensure that negative pressure does not draw in air or body fluid which is proximal to the syringe and can therefore slip between the re-sealable port and the syringe during the refilling process). For example, a specified reservoir pump 23 can be operated in a reverse direction while the flow controllers 20 of the inlet port 24 are set to the correct states so that a particular reservoir 14 is filled as directed by the CA 22, and the external source of drug fluid applies a similar positive pressure to the fluid which is used to replenish the DDS. It is recognized that the TCFA can monitor the amount of fluid (as well as flow rate, pressure, etc. . . . ) of the fluid being directed into the input port 24. If the inlet port 24 routes the drug fluid between the inlet port 24 and the mixing chamber 40, then the reservoir flow controllers 20 which terminate within the mixing chamber 40 housing can be operated to control flow into the different reservoirs 14. In a preferred embodiment, when operating in the Replenishment mode, the DDS can also cooperate with a DDS tester/calibrator/filler apparatus to help increase the speed, accuracy, and ease of the refilling operations.

The internal pumps 23 of the DDS act in conjunction with, or communicate with, an external pump associated with the fluid source in order to refill the internal reservoir 14. By having both the external and internal pumps work together, the vacuum produced in the reservoir 14 when the pump 23 is operated in a reverse manner can not draw in unwanted fluid which may, for example, slip in between a needle and the septum of the input port 24 of the DDS. Further, provided is refilling more than 1 reservoir with different drugs from the single inlet port 24. For example, in one embodiment the DDS uses a method of refilling the reservoirs 14 wherein all the flow controllers 20 are set in their "closed" position, except for the flow controllers 20 which enable fluid to flow to a specific reservoir 14 and the pump 23 for that reservoir 14 is operated backwards to pull the substance into the specified reservoir 14, and the vacuum is substantially equivalent to help to balance the positive pressure provided by the drug supply pump associated with the fluid source, thereby helping to decrease the risk of an influx of air or increased pressure.

The Implantee-Replenishment mode enables fluid from the implantee to be drawn into the DDS and subsequently used as a drug, buffer fluid and/or diluent. The Implantee-Replenishment mode normally will use an inflow catheter. 30 of FIG. 1b, whereby fluid is drawn into the DDS from the implantee and then used to deliver drugs through one of the catheter hubs 16. Alternatively, the Implantee-Replenishment mode can be used where fluids are drawn in from the catheters 80 connected to the hub 16 which are not the inflow catheter and within which the drugs of the other reservoirs 14 are delivered. However, it is often preferable to use the inflow catheter 30 because it could be disadvantageous, for example, to deliver drug and then draw fluid in from the same distal site, which may contain a portion of the drug just delivered. Further, the inflow catheter 30 can draw in fluid which it filters using either a filter on its distal tip 34 (see FIG. 1b), or a filter located anywhere along its length. The filters used to filter the fluid entering the inflow catheter 30 may be a physical, chemical, electrical, osmotic or other filter or combination of several filters. The implantee replenishment mode provides the fluids of the DDS to last a longer time as compared to current technology. By using the fluids available inside the implantee, a relatively endless supply of buffer and diluent fluids (and certain biological fluids that can act as therapeutic agents), as compared to current systems, can be used without the need for the DDS be refilled.

The Sample-Push, Filter, Purging, and Shunt modes, like the Implantee Replenishment mode, normally utilize fluids from the inflow catheter 30 (although any of the catheters can be used). When operating in a Sample-Push mode, fluids can be drawn into the DDS from the implantee and can then be routed through the catheter hub 16 to the attached catheter which transports the fluid to the distal location where these samples can be accessed by medical personnel. In other words, if a DDS uses, for example, 5 catheters, then one of these catheters can be used to send fluid where medical personnel can easily access it. The end of this specific catheter, termed the "sample-push catheter" may be fitted with a small fluid containment system (e.g., a receptacle) in order to hold this fluid prior to its access by medical personnel. In this way, samples of substances which are proximal to the sites of drug delivery can be easily obtained for comprehensive analysis, for example, using chromatography, DNA, RNA, protein, or chemical assays and other analysis techniques. When the DDS operates in a Filter mode it may draw in fluid through the attached catheter to the hub 16 and, after filtering it by means of physical, chemical, electrical, or other means, the filtered fluid may be redeployed by the DDS through the same lumen of the catheter or through an alternative path. The filtrate can be disposed of by operating the DDS in a Purging mode, which is a variant of the Sample-Push mode, so that filtrate does not accumulate past a specific level within the DDS. For example, when operating the DDS of FIG. 3 in a Filter mode, the fluid to be filtered may first be drawn into the mixing chamber 40 through catheter hub 16a. Next, one or more filters such as an electrochemical filter, a nanotube filter (e.g., nanotube membranes can be used to cleanly separate small molecules on the basis of molecular size as described in Wirtz et al, 2002), a chemical filter, or other filter acts to remove filtrate from the fluid. In the next step, the filtered fluid is drawn into the reservoir 14a,b, such as Res1 until a specified amount of fluid has been filtered or a certain amount of filtrate has been obtained. In the next step, a buffer fluid is used to push the filtrate out of catheter hub 16b and into the connected second catheter which acts to purge the filtrate from the DDS and into, for example, an area of the implantee where it will not be harmful or the systemic circulation. The Purge mode can also be used to send unwanted air or gas which has entered the DDS (due to, for example, a chemical reaction which occurred during mixing of drugs or due to gas that was present in implantee fluids that were drawn into the DDS) so that this does not interfere with pumping operations or become mixed in the catheters attached to the hub 16 with the fluids to be dispensed. In another embodiment of the Filter mode, the fluid which is drawn into the DDS undergoes a transformation. For example, a chemical can be mixed with the fluid to change its chemical nature (e.g., increase its PH level). Additionally, substances can be mixed with the fluid which is drawn in from the implantee in order to functionally neutralize an unwanted characteristic of the implantee fluid by, for example, causing certain molecules in the implantee fluid which has been drawn into the DDS to bind with a therapeutic drug that acts to competitively bind with (or break down or transform) those molecules. After this fluid has been altered or "functionally filtered" with respect to the unwanted characteristic, it can be re-dispensed from the DDS through the same or different catheter attached to the hub 16. Since some of these changes require time it is sometimes advantageous to treat the fluid of the implantee within the DDS rather than by delivering fluid outside the DDS into the fluids of the implantee. Further, the filtering operations can be guided by sensors which are incorporated into the filter. The filter for the DDS can be located in the mixing chamber 40, or may exist adjacent to the mixing chamber 40 and can contain at least one flow controller 20 controlled by the CA 22 for allowing fluids to enter and exit through different paths connected to the mixing chamber 40, and can be configured so that the filtrate or unwanted fluid can be purged from the DDS in a manner than is not harmful to the implantee.

When the DDS operates in a Shunt mode, it first operates its pump 23 to draw fluid into the DDS through the hub 16a and then pumps this fluid through another catheter attached to a hub (e.g., 16b) to, for example, shunt fluid from the body of the implantee or to redirect this fluid to another area within the body of the implantee. In the shunt mode, and other modes, the DDS does not have to actively pump fluid from the implantee into the DDS, but rather the fluid of the implantee can enter the catheter 80 (or inflow catheter) due to natural pressure which biases the fluid to leave an area of the body and enter the DDS (i.e. passive rather than active fluid flow actuation, where, for example, the DDS sets the flow controllers to their open state so that a fluid path serves as a conduit between two catheters).

When operating the DDS in its various modes, the total volume of all components of the drug delivery DDS should be known. The fluid volume of any component of the drug delivery DDS, for example, within each reservoir 14, connection pathways 18, mixing chamber 40, and catheters 80 attached to the hub 16 and inlet port 24 are determined in order to properly control the delivery of fluids. These parameters are either sensed by the CA 22 or are sent to the CA 22 as commands and/or data signals from an external controller, such as but not limited to the TCFA. For example, if a surgeon attaches 3 catheters to the DDS hub 16 which are 18 cm, 12 cm, and 6 cm long, with different internal lumen volumes, the DDS will have to operate differently than when dispensing fluid without these three catheters. When a surgeon chooses the length of the catheters which will be used with the drug delivery DDS, or modifies the length of the catheter so that it efficiently delivers drugs to a desired area of the patient, the lengths and volumes of the catheters are programmed into the Lengths and Volumes table Rt2 of the DDS. (see FIG. 11) which is stored in the memory 308 of the CA 22, which is stored in the computer 300. Additionally, if the mixing chamber 40 has a pump 48, or other means by which the volume of the chamber 40 is modified, then the value of this real-time volume is updated in the Fluid Volume table St4 of the database 322. By utilizing both the volumes of the fluids in the catheters and the real-time volumes of the DDS components such as the mixing chamber, calculations are performed by the processor 300 which allow appropriate amounts of fluids to be pumped, thereby achieving desired drug delivery.

The Mixing Chamber

Embodiments of the DDS can incorporate a mixing chamber 40. The mixing chamber 40 may have pressure, chemical and other sensors, and flow controllers 20 which control the flow of fluids into and out of this chamber 40. The mixing chamber 40 provides many advantageous over the prior art, for example the mixing of fluids can occur independently from their delivery through the catheters 80 connected to the hub 16. When fluids are mixed to obtain specific concentrations of drug, the concentration can be checked by chemical sensors in the mixing chamber 40 prior to the delivery of the drug to the hub 16 and ultimately the attached catheter 80. Other advantages occur when the mixing chamber 40 is used with various delivery modes of the DDS as is described in different areas of this specification.

The mixing chamber 40 may have an adjustable internal volume. The volume can be adjusted to create positive pressure to expel fluid from the chamber 40, a negative volume to draw fluid into the chamber 40, or to adjust pressure as drug is pumped into the chamber 40 by the reservoir pump 23. In FIG. 4, a partial view of one embodiment of the DDS is shown where a volume adjustment mechanism is provided in the mixing chamber 40 which, in this example, is a plunger 46 which is attached to a pump 48, which may be a rod attached to a pump 23, for moving the plunger in forward D1 or reverse D2 directions, in order to make the volume of the mixing chamber 40 larger or smaller to accommodate the volumes of fluid intended for mixing in the chamber 40. The movement of the plunger 46 can cause a negative pressure with respect to the fluid in the catheter hub 16, the reservoirs 14, and/or inlet port 24 and thereby, when respective flow controllers 20 are in their open position, cause the fluid to be drawn into the mixing chamber 40 via the port(s) 16,24. The volume adjustment mechanism can be operated in conjunction with the pump 23 of the reservoirs 14 so that the pressure differential which occurs between the mixing chamber 40 and the other internal components of the DDS (e.g., the catheter fluid pathways 18) remains below a desired level. Alternatively the mixing chamber 40 can change its volume by being realized in the form of an elastic chamber (similar to a balloon), which expands as fluids enter it. A plunger 46 can be operated against the outside of this mixing chamber 40 to cause fluid to exit from the chamber 40. The mixing chamber 40 can aid in the delivery of drugs from the DDS. For example, when the catheter hub flow controller 44 is set to an open position and the reservoir flow controllers 20 are set to their closed position, movement of the plunger 46 in the forward (D1) direction causes fluid to enter the catheter hub 16. The mixing chamber 40 can be used when refilling the DDS from an external source, during the Replenishment mode, in order to route fluids to specific reservoirs 14. For example, the mixing chamber 40 can contain flow controller 20$p$ and connection means 42$p$ which transmit fluid between the mixing chamber 40 and the inlet port 24. By operating the flow controllers 20, drugs which are delivered to the inlet port 24 can be routed to specific reservoirs 14. The ability of the mixing chamber 40 to change its volume can be advantageous during mixing, and refilling operations, because the mixing chamber 40 can decrease pressure that may normally act against fluid flowing into or out of the chamber 40 via the fluid pathways 42 connected thereto. The prior art does not contain mixing chambers, or adjustable volume mixing chambers, and requires that drugs be mixed completely in the catheters and/or once delivered, to the patient. The lack of the mixing chamber in prior art can result in the problem that when drugs are to be mixed, they must be dispensed to the catheter and this will necessarily cause drugs to be delivered from the distal end of the catheter. The mixing chamber 40 of FIG. 4 contains a filter 25. When this filter has its own pump, the filter 25 can also act to circulate fluids within the mixing chamber 40 to assist in the mixing of drugs.

The mixing chamber 40 may have its own sensor 21 for sensing the concentration of the drug in the fluid contained in the mixing chamber 40. The mixing chamber 40 may have its own pump (see FIG. 4), which is operated by the control apparatus 22. If the mixing chamber 40 has its own pump (e.g., a motor means actuating a plunger), this may be operated by the CA 22 so as to increase the volume of the mixing chamber 40, as fluid enters from the reservoirs 14, and to decrease the volume of the mixing chamber 40, in order to dispense the fluid from the mixing chamber 40 into the catheter hubs 16, when associated flow controllers 20 of the adjacent fluid pathways 42 are configured to operate in cooperation with the movement of the plunger 46. By adjusting the volume of the mixing chamber 40 so that it is equal to that pumped into and out of the mixing chamber 40, the effects of compressible air or gas which may become stuck in the mixing chamber 40 can be decreased. When the mixing chamber 40 does not contain a mechanism for volume adjustment, e.g., 46 & 48, then the pressure from the fluid in the reservoirs 14 which enters the mixing chamber 40 can be used to pump the fluid from the mixing chamber 40 into the catheter hubs 16 by setting the reservoir flow controllers 20 and the catheter hub flow controllers 20 to their open positions while the reservoir pumps 23 are activated in the forward direction.

Additional Examples of Alternative Embodiments of the DDS

The DDS can be realized in a rotational embodiment, whereby there is an inner component which can be rotated relative to an outer component that contains at least one catheter hub 16. In order to dispense fluid from a specific reservoir 14, the inner component is rotated until that reservoir 14 is in functional contact with the specified catheter hub 16. In FIG. 5, an exemplary illustration of a DDS 10 is shown which is realized through a rotational embodiment. The reservoirs 14 reside within a cylindrical housing 60 which may be rotated so that any of the individual reservoirs 14*a-c* can achieve functional connection with one of several catheter hubs 16*a-c*. In the embodiment which is shown, the internal cylindrical housing 60 includes 3 reservoirs 14*a-c*, a control apparatus 22, and catheter connection means, which in this case are connection tubes 18*a-c*. The internal cylindrical housing 60 is rotatably mounted within the DDS and its perimeter forms an inner ring 62 within which is embedded the flow controllers 20*a-c*, for the reservoirs 14. Under control from the control apparatus 22, the inner ring may rotate within an outer ring 64, for example, due to a motor, which may be a small motor which is capable of rotating the inner component so that a given reservoir flow controller 20 is positioned to functionally connect with the catheter hub flow controllers 44*a-c* of a specified catheter 80 attached to the hub 16. In one embodiment, one of the multiple reservoirs 14 contains a buffer fluid in order to push the drug through to the distal end of the catheter 80. The rotational embodiment of the DDS may deliver fluids in a continuous mode, a bolus mode, a Sequential Bolus mode, a flow-return mode, replenishment mode, or other operational mode as described herein. One advantage of the DDS of FIG. 5 is that less fluid is stored in the catheter connection pathway/tube 18 and the connection pathways/tubes 18 do not require much space. When there are several catheters 80 and many reservoirs 14 and connection tubes 18, the amount of drug in the connection tubes 18 may become relatively large and may act to deplete the amount of drug stored in the reservoirs by more than a desired amount.

The DDS can enable the fluid stored in one or more reservoirs 14 to be delivered out of one or more catheters 80 via the hub 16 using a dynamic catheter connector mechanism such as but not limited to the tube 18. In FIG. 6, an implantable drug delivery system 10 is shown which includes multiple catheter hubs 16*a-c*, multiple reservoirs 14*a-c*, and a control apparatus 22. The DDS contains a dynamic catheter connector tube 18 which allows any of the reservoirs 14*a-c* to become physically connected to any of the catheter hubs 16*a-c*. In the specific embodiment shown here, the bottom end of a flexible catheter connection tube 18 is moved along an inner track 70 until it is positioned for functional connection with a specific efflux region of the reservoirs 74*a-c* through which fluid can be pumped. The top end of the flexible catheter connection tube 18 is moved along an outer track 72 until it is positioned for functional connection with a catheter hub 16*a-c*. A flow controller 20*a* controls the flow of fluid from the reservoir tips 74*a-c* into the connection tube 18, and a flow controller 20*b* and catheter hub flow controllers 44*a-c* control the flow of fluid from the catheter connection tube 18 into the catheter hub 16. When the flow controller 20*a* is not in contact with the efflux region of the reservoir 74*a-c* the inner track 70 provides a watertight seal with the efflux region of the reservoirs 74*a-c* (alternatively each efflux region may contain a flow controller 20 which is not shown). Similarly, when the upper end of the dynamic connector tube 18 is not in contact with the catheter hub 16, the catheter hub flow controllers 44*a-c* halt flow out of the catheters 80 (alternatively, the outer track 72 provides a watertight seal with the catheters 80). Alternatively, additional flow controllers 20 can be incorporated into the design in order to control the unwanted flow of fluid in the catheters 80 and reservoirs 14. A dynamic connector 18, such as the flexible connection tube, provides for fluid communication between the reservoirs 14 and the catheter hubs 16. By controlling the movement of the top and bottom end of the dynamic connector 18 appropriately, the control apparatus 22 can provide a functional connection between any of the reservoirs 14 and catheter hubs 16 as used in the particular drug delivery regimen programmed into the computer 300 of the CA 22. The dynamic connector 18 embodiment of the DDS may deliver drugs in a continuous mode, a Bolus mode, Sequential Bolus mode, Flow Return mode, Replenishment mode, or other mode as desired. The medical drug delivery system, may be completely implanted or may exist partly outside of the body, as is sometimes done with insulin delivery systems, for example, the MiniMed Paradigm™, insulin product, pager-sized device typically worn on a belt, drug is delivered through a transcutaneous catheter. Accordingly, some parts may be mounted externally or implanted subcutaneously.

Various components of the medical drug delivery system can be miniaturized considerably compared to the embodiments shown in the FIGS. The scale of components in the FIGs are for illustration purposes and do not necessarily represent the sizes and scales of the components. For example, miniaturized embodiments of the connection means, reservoir flow controllers, CFCMs, pumping means, and other components of the implanted DDS, can be based upon technology such as that described in U.S. Pat. No. 6,408,878, which is incorporated by reference herein, and which describes microfabricated elastomeric valves which may be switching valves, on/off valves, and pump systems which can be incorporated into the design of the implanted DDS of the current invention. For example, the connection means and flow controllers which serve to guide fluid from the reservoirs to one or more catheters can be embodied in a very thin silicon-based or elastomeric multilayered plate which is functionally connected to the reservoirs and one or more catheters. While the relatively small size of the microfabricated elastomeric valves and pumps can not provide the pressure, resistance, or responsiveness needed for a system which uses catheters to deliver drugs to sites distal to the pump, the microfabricated components can used in conjunction with the larger components of the implanted DDS to deliver precise amounts. In this manner a hybrid micro/macro network is utilized by the drug delivery system, where the microstructure feeds the larger components which are capable of dispensing the drugs more efficiently and at greater pressures.

The use of a buffer fluid becomes even more important when 2 or more drug reservoirs are used in the implanted drug delivery system. In the case where 2 or more drugs are routed through a single catheter, the buffer technique enables the drugs to be delivered more precisely than prior art. For example, if one drug is excitatory and the other is inhibitory, then sending out both drugs from a single catheter can be difficult or even impossible since the drug already in the distal portion of the catheter must clear the catheter prior to the newly introduced drug being transported down the length of the catheter to the distal end. If there is a neutral buffer fluid in the catheter, this may be dispensed through the distal end of the catheter as the subsequent drug makes its way through the catheter with no ill effects.

The medical drug delivery system contains a method for delivering a drug bolus functions by having at least one active drug and a pusher substances, each of which are output from their respective reservoirs consecutively. For example, a given dose of drug is dispensed from a Res1 14*a* into the catheter. This drug takes up ⅛ of the entire catheter length. The Res2 14*b* holds an inert solution, which may be a diluent, but which in this application serves as a pusher fluid which acts to push the drug from Res1 14*a* down the remaining length of the catheter, so that it is delivered as a bolus of a certain strength to the target located at the distal end of the catheter. The amount of pusher fluid that is dispensed is sufficient to send the drug through the distal end of the catheter and is calculated based upon the length and radius of the catheter. Utilizing a neutral fluid buffer has several advantages. When a certain dose is required by the target, normally the drug which has been dispensed earlier must clear the entire length of the catheter. By using a buffer fluid and buffer mode, only the specific amount of drug that is required is delivered to the target. Further, the system may be made more efficient by operating the pumping means for the buffer reservoir in a reverse manner, after the drug is delivered, in order to draw the fluid back into the buffer reservoir in order to use as little of the buffer solution as possible. The dual catheter designs may assist this type of operation.

Specialized Catheter Operation

Figure 7B:
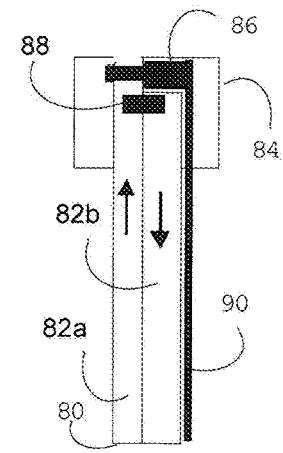
Figure 7C:
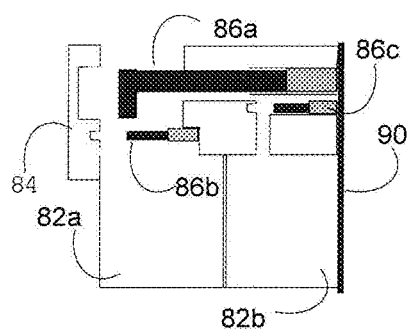
FIG. 7c shows a further embodiment of the two-lumen catheter of FIG. 7b.
Figure 7D:
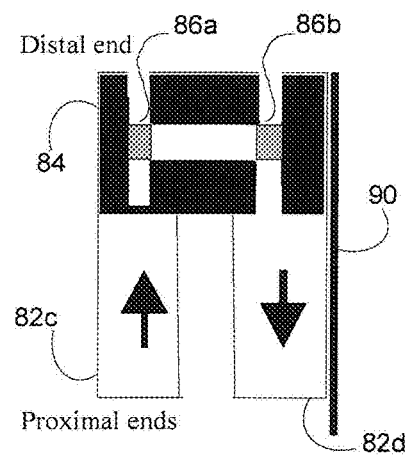
FIG. 7d shows two single lumen catheters as an alternative embodiment of the two-lumen catheter of FIG. 7b.

In FIGS. 7*a-d* multi-lumen catheters 80 are shown, which contain only two lumens, although more lumens are possible. Turning now to FIG. 7*a*, a dual-lumen catheter assembly 80 is shown, which here contains a first lumen 82*a* and second lumen 82*b*. The catheter 80 has a distal end which here contains a cap or flow control system 84 connected to the first distal end of the lumen 82*a* and the second distal end of the lumen 82*b* for connection to the target site of the patient. The flow control system 84 may contain an anchor mechanism for anchoring the distal end of the catheter 80 to a target delivery area of the patient as is described in U.S. Pat. No. 6,537,241, and U.S. Pat. No. 6,471,689 (the '689 patent), incorporated by reference herein. As described in the '689 patent, the catheter cap 84 can be designed so as to deter blockage of its opening (for example, due to acute fibrous tissue encapsulation and cellular deposition), can be coated with surface treatments, and/or can be configured so as to encourage vascular ingrowth while inhibiting blockage of drug delivery. The flow control system 84 has at least one directional flow controller embodied in a catheter flow control mechanism (CFCM) 86 (e.g. a catheter version of the DDS flow controller 20) that can have at least one "open" state which directs fluid to flow between two locations and a "closed" state which directs fluid by inhibiting fluid flow between the two locations. When more than one open state or position is possible the different open states can allow for fluid to travel along different fluid paths. For example, position 1 is an open position wherein output fluid can be dispensed from at least one lumen 82*a,b* of the catheter 80 to the target site of the patient, position 2 is an open position which connects the first 82*a* and second lumen 82*b* but prevents output fluid from exiting the catheter 80 (hence facilitating inter-lumen fluid flow), and position 3 is closed position which inhibits flow between the first 82*a* and second 82*b* lumen and also prevents fluid from flowing from the distal ends of the lumens 82*a,b* to the implantee. One embodiment of the flow controller 86, which has been realized in the form of a piston valve, is shown in an open state in FIG. 7*a*. In FIG. 7*b*, the CFCM 86 is shown in a closed state such that fluid can not be delivered to the implantee. A different type of flow controller termed an inter-lumen flow controller mechanism (ILFCM) 88 is also shown. The ILFCM only permits fluid travel between the distal ends of the lumens of the catheter. Accordingly, the controllers 86,88 direct fluid between the lumens 82*a,b* as inter-lumen fluid flow, as well as direct fluid out of the distal ends of the lumens 82*a,b* as output fluid flow. The operational states of the CFCM and ILFCM can be controlled by at least one communication link 90, which allows communication, power, and control signals to be sent along the outside of a catheter 80 or is contained in the body of the catheter 80. The communication link 90, for example, can be a single wire or can be several wires and allow for communication of control signals between the catheter cap 84 and the control apparatus 22 of the DDS. The communication link 90 can use both electrical/hydraulic methods of actuating components along the catheter 80. The DDS sends control signals via the communication link 90 to the flow controllers 86,88 of the flow control system 84, in order to manipulate the controller 86,88 into one of the state positions, for example as described above. When the catheters 80 are formed/connected upon the catheter hubs 16 then there is a continuous connection between the electrical communication link 90 and the control apparatus 22. However, when the catheters 80 are, for example, obtained separately and then attached to the DDS, the catheter hubs 16 can contain electrical connections which are used to connect the CA 22 to the electrical communication link 90 of the catheter 80. None of the FIGs contain electrical circuitry diagrams to avoid cluttering of the figures, but it is understood that in most embodiments the control apparatus 22 communicates with and supplies power to the other components of the DDS though wires or other means of transmitting power and/or communicating (e.g. fiber optics). The electrical link 90 can also be used to power an irradiation device located at the tip of the catheter 80, as directed by the CA 22, in order to activate photosensitive drugs (not shown), or can be attached to a sensor. The DDS can also communicate with the catheter cap 84 via telemetry. If the CFCM or ILFCM are incorporated into the catheter cap 84, then the power and control signals initiated by the CA 22 can be directed by the cap 84 which can contain a power source and microcircuitry which is in communication with the control apparatus 22, for example, by means of telemetry. The CFCM 86 and catheter cap 84 can obviously be used when more than two lumen 82*a,b* are in the catheter 80 or with a single lumen catheter 80 as well. In FIG. 7*c*, an exemplary embodiment the catheter cap 84 is shown with three discreet flow controllers 86,88, which in this example are 3 solenoid valves, which control fluid flow out of the catheter 80 and between the 2 lumens. For example, when CFCM 86*a* and CFCM 86*b* are in the open position and CFCM 86*c* is in the closed position then output fluid may be delivered from the first lumen 82*a*, and when the CFCM 86*b* for the first lumen 82*a* is closed and the CFCM 86*a* and CFCM 86*c* are open then output fluid can be delivered from the second lumen 82*c*. Setting only CFCM 86*b* and CFCM 86*c* to the open position and CFCM 86*a* to the closed position permits inter-lumen fluid flow between the two lumen of the catheter. FIG. 7*d*, shows a cross sectional schematic of an alternative embodiment of the cap 84, wherein CFCMs 86*a*, 86*b* control both output and inter-lumen fluid flow. It is recognized that the flow control system 84 determines if fluid is delivered from the first lumen, or the second lumen, or flows between lumen in a closed system which forms a fluid circuit wherein a sequence of drugs 91 and buffers 93 (see FIG. 8) can be circulated through the lumen of the catheters 80. Several catheter caps 84 can be located along the catheter 80, each of which permits fluid to be dispensed to the implantee or re-directed internally.

Referring again to FIG. 7d, the two single lumen catheters 82c,d are shown connected at their distal ends by the flow control system 84. Flow controllers 86a,b can be set to a first open state position which allows fluid to flow from the two single lumen catheters 82c,d into the implantee. A second open state position which allows fluid to flow from the first single lumen catheter 82c and the second catheter 82d, or a closed state which inhibits fluid from flowing between the two lumens 82c,d and their distal tips.

In a Flow-Return mode a drug can be transferred to the distal region of one lumen 82a of the catheter 80 for drug delivery, but instead of displacing fluid that has previously entered that lumen 82a by delivering it to the patient, the CFCM causes the fluid to flow into an adjacent lumen 82b, for transport back to the reservoirs 14 of the DDS. For example, in FIG. 3, the catheter hubs 16a and 16c can be routed to the first 82a and second 82b lumen, respectively. Accordingly, fluids may be circulated within the lumen of the catheter 80 and thereby enable multiple drugs to be delivered without requiring that drugs in the catheter 80 be delivered to the patient in order to enable subsequent drugs to be delivered. For example, in FIG. 8 the two lumens 82a,b have multiple drug fluids 91 separated by buffer fluids 93. The flow controller 86, 88 can be operated via the link 90 by the DDS, such that the sequence of fluids 91, 93 can be rotated between the lumens 82a,b as inter-lumen fluid flow to position a selected fluid 91,93 resident in the catheter 80 adjacent to the distal end of one of the lumens 82a,b. Once positioned, the flow controller 86, 88 can be operated by the DDS to direct the selected fluid out of the catheter 80 as output fluid.

In FIG. 8, a dual lumen catheter 80 is shown which includes a catheter pump flow controller 92 which can circulate the fluids 91, 93 in a clockwise or counterclockwise manner through the interconnected lumens 82a,b, and which can draw additional fluid into the lumen of the catheter 80 from the DDS catheter hub 16a, and can pump fluids back into the DDS through the catheter hub 16a, such that the controller 92 can have three ports (one for each lumen 82a,b and one for the hub 16). The catheter pump flow controller 92 is connected to the DDS catheter hub 16a using a catheter hub connector 16a' which, in this embodiment is formed upon the catheter hub 16a of the DDS and permits electrical/hydraulic control continuity between the dual lumen catheter and the control apparatus 22 of the DDS 10. The catheter pumping means 92 may contain chemical or other sensors that can help detect what fluid it is pumping (e.g., buffer 93 or drug 91). The dual lumen catheter contains a first CFCM 86a for controlling flow between the first and second lumen and for dispensing drug from the tip of the catheter. Additionally, more proximal to the DDS housing is a second CFCM 86b which controls the flow of fluids along and between the lumen of the catheter 80 and which can also release fluid into the implantee. In this embodiment, the first and second CFCM are housed within catheter caps 84a, 84b. Both the catheter pump 92 and CFCMs are under control of the control apparatus 22 of the DDS. During normal operation, several fluids 91 are contained in the lumen 82a,b at once and are separated by buffer fluids 93. The drugs 91 and buffer fluids 93 can be circulated with the CFCMs 86a, 86b until a specified drug 91 is positioned to be delivered from, for example, catheter cap 84a. A pump flow controller 20, which may be the catheter pump 92, is then operated in a clockwise manner with the flow controller 86a set to an open state which causes the specified drug 91 to exit from the distal tip of the catheter 80. In one embodiment the catheter 80 can incorporate a microchip (see US pat application 20030105455) which dispenses fluids into the diluents or buffer fluids 93 as they circulate in the fluid circuit made up of the two lumens 82a,b connected to the hub 16. The fluid circuit can then act as a fluid path for allowing the microchips to deliver their contents to distal locations while optimizing the use of buffer fluid 93 (or diluent fluids) in the process.

FIG. 8 shows a flow controller 86 and a catheter cap 84 configured so as to permit fluid to travel between two lumens 82a,b or to be dispensed from the distal end of the catheter 80. In the figure the first and second lumen 82a,b are physically connected by a shared lumen wall. In an alternative embodiment, the two lumens 82a,b are physically separated and form a single lumen which acts as a loop through which the fluids may travel. The two ends of the loop are connected to a catheter pump 92 or to two separate catheter hubs 16. The fluid circuit may deliver drugs 91 to several locations in a single organ or may deliver drugs to different organs.

When the catheter 80 contains two or more lumen 82a,b its radius is increased. In applications such as neurostimulation which sometimes requires thin catheters 80 to be used, the volume of multi-lumen catheters 80 can become undesirably large. This problem can be overcome by utilizing a multi-stage catheter 80 with at least two stages that are separated by a CFCM. In FIG. 9 two types of multi-stage catheters 80 are shown, both of which contain 2 stages. In the multiple-single (termed "M-S") multi-stage catheter 80 shown on the left side of the figure, the first stage is a multi-lumen catheter 80 containing 7 lumens which are connected to different catheter hubs 16 of the DDS. The multi-lumen catheter 80 terminates in a CFCM 86 which can be operated to determine the lumen from which fluid will flow into the second stage, which is a single lumen catheter 80. The CFCM 86 can be simple and utilize, for example, a valve that determines which of the multiple lumen can send fluid to the second stage, or can also include components such as a catheter pump flow controller 92 and connection pathways 18 and output ports 16. The CFCM 86 or other components which connect the stages of the multi-state catheter system can be powered by at least one electrical/communication link 90 which can be controlled by the control apparatus 22 of the DDS, or can be controlled by the DDS using telemetry. The electrical communication link 90 can also be extended to the second (or even third) stage of the multi-stage catheter 80 (although this is not shown in the figure). The center of FIG. 9 shows a diagram which illustrates that the multi-lumen segment of the catheter 80 can have multiple lumens. In the figure, the multi-lumen catheter 80 has 7 lumens, although it may contain more or less than this amount. On the right side of the figure, a single-multiple ("S-M") multi-stage catheter 80 is shown. The S-M catheter 80 is useful when a single drug from a single catheter hub 16 should be sent to several different delivery areas that are not adjacent. The S-M catheter 80 is also useful when sending multiple-drugs from a single catheter hub 16 to many areas. The S-M catheter 80 is also useful when operating the DDS in Sample-Push, Purge, or Shunt modes where increased diversification of pump operation, due to its various modes, may be difficult to achieve with only 1 or 2 catheter hubs 16. The S-M catheter 80 may also be more cost effective than providing a DDS with several different catheter hubs 16 and their related internal components which enable proper function. Accordingly, rather than different lumen 82a,b originating at different catheter hubs 16, a single lumen 82 can carry the fluids to location closer to the delivery sites and then, using a CFCM

86, multiple catheters 80 can carry the fluids to their specific targets. Both the S-M and M-S catheters 80 can be sued with the DDS 10, or with generic drug pump 6.

Drug Delivery System Tester/Calibrator/Filler Apparatus

The complexity of filling, re-filling, testing and calibration operations, which subsequently permit more accurate drug delivery, is greatly increased for implantable devices which are capable of delivering complex delivery regimens and which may contain multiple fluids that are stored within multiple reservoirs. Instruments which assist these operations permit implantable drug pumps (e.g. DDS) to be filled, tested and calibrated much more quickly, easily, and accurately than using strictly manual methods. A tester/calibrator/filling apparatus (TCFA) improves the accuracy of drug delivery and facilitates the creation and testing (and fine tuning) of different (e.g., customized) treatment regimens, testing of the internal components of the delivery system, calibration, filling of the various internal components of the implantable drug pump with specific fluids, and other operations, all of which are termed "TCFA operations". While the TCFA 190 can be used with the DDS (e.g., 10, of FIG. 1*a*), it can also be used generically with implantable drug pumps (e.g., 6 of FIG. 10) that are produced by various manufacturers. The TCFA 190 may be a self contained and specialized desktop instrument (with display and other means offered by a computer), a handheld instrument, and/or may be comprised of distributed components which are under the control of a personal computer (PC) which controls the TCFA via a computer link 188.

Figure 10:
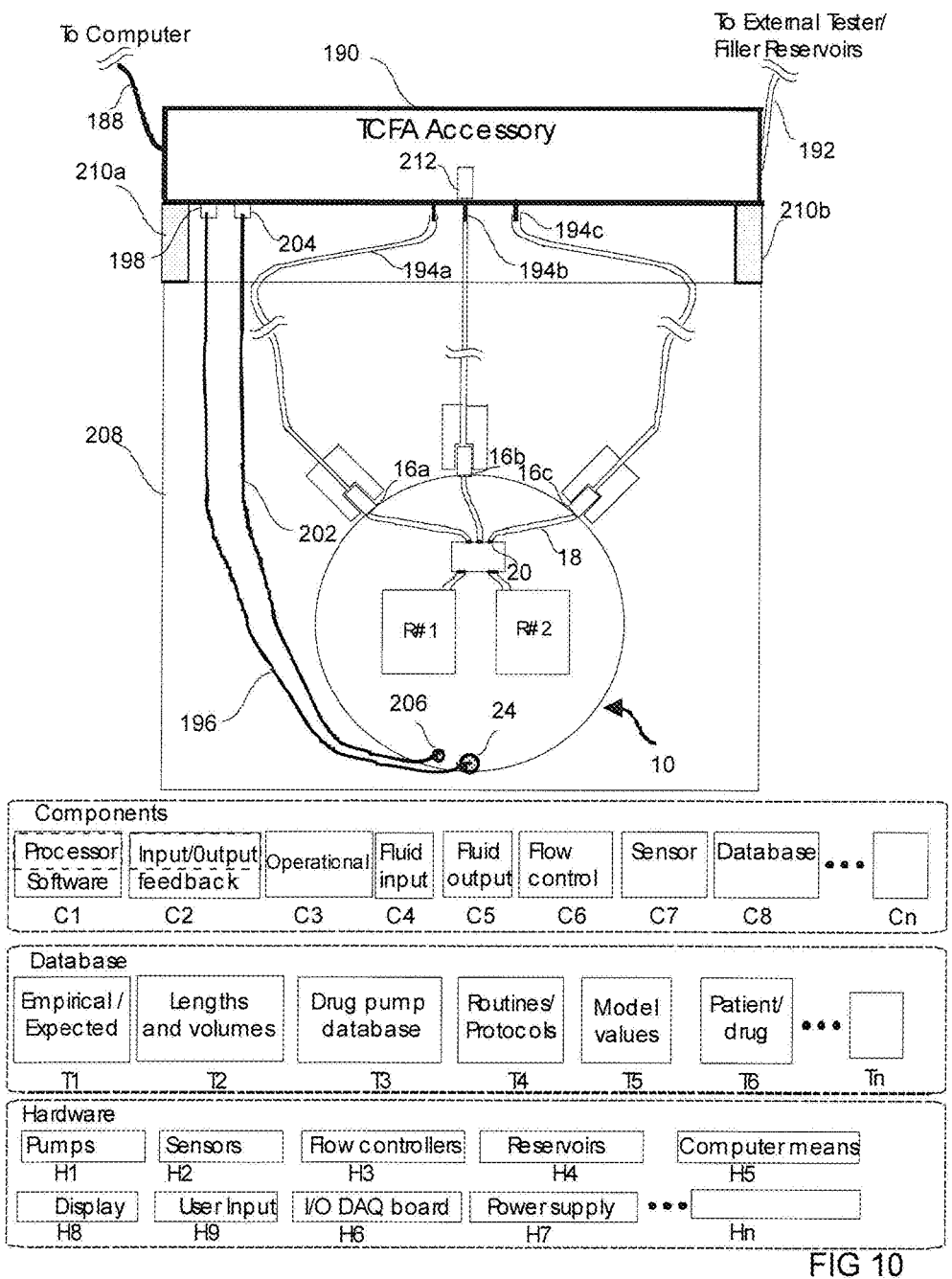

Referring to FIG. 10, the TCFA operations are controlled by a processor component C1, which may be a PC, and which operates based upon specialized software programs that control the TCFA operations. The processor component C1 provides for effecting the commands of TCFA software programs embodying TCFA operations in conjunction with the coupled drug pump 6, performing calculations and operations and other capacities which would be typically expected from a motherboard of a computer H5, and allowing for controlling of, and communicating with, TCFA components. The component C1 interacts with the other components Cn, such as the operational component C3 which sends and receives command/data signals for the respective hardware Hn (e.g. turn pumps H1 on/off, sense fluid characteristics data through sensors H2, etc. . . . ) and can access the database tables Tn, as further described below. An input/output component C2 provides for enabling communication between and the user (e.g., via a display H8 keyboard, physical or virtual switches and knobs H9, or combined as a GUI) and the operational component C3 via the processor component C1, for example modifying pumping operations of the pumps H1, or receiving/sending command/data signals with an external patient controller (not shown). The input/output component C2 can utilize an DAQ card H6 such as a e-series DAQ from National Instruments to provide a physical link for communication and data transfer between the TCFA and the drug pump 6 (which can also enable the TCFA to provide the drug pump 6 with power via a power supply H7). The input/output component C2 can also communicate/control, via telemetry. The TCFA contains or is in functional connection with the operational component C3 which provides for achieving the TCFA operations as dictated by the processor component C1 and includes control circuitry for controlling pumps H1, pressure/chemical/flow/optical sensors H2, flow controllers H3, reservoirs H4, and other hardware necessary to perform TCFA operations in connection with the drug pump 6. The input/output component C2 can utilize a software interface for programming or controlling the TCFA can be a user friendly graphical user interface (GUI). The GUI can have similar look to that utilized by DigiStat's modular software architecture (e.g., "Therapy Prescription" see <http://www.unitedms.com/digistat.shtml>, incorporated by reference herein) which is used to create clear, intuitive software embodiments of delivery regimens. GUI's can act as "virtual instruments" which can enable software routines to perform the, for example, filling/testing/calibration TCFA operations by controlling both pump 6 and TCFA operations in accordance with user commands directed to the component C1.

The TCFA also has a fluid input component C4 to measure input fluid values (such as but not limited to pressure, temperature, volume, weight, flow rate, etc. . . . ) during the filling of at least one reservoir of the pump 6 and can also actively control the transfer of fluid from the fluid sources connected to the TCFA (or connected to drug pump 6 directly) via the source catheter 192 and/or fluid delivery catheter 196 connected to the input port 24 of the drug pump 6. The fluid input component C4 may also control a mixing flow controller H3 directed by the operational component C3 to provide the required drug fluid. The TCFA also has a fluid output component C5 to measure output fluid values (such as but not limited to pressure, temperature, volume, weight, flow rate, etc. . . . ) during the emptying of at least one reservoir R#1 through the output port 16*a,b,c* and can also actively control the transfer of fluid from the drug pump 6 connected to the TCFA via the fluid delivery catheters 194*a,b,c*. The input and output components C4,C5 are directed by the processor component C1. The TCFA can also have a flow controller component C6 directed by the processor component C1 and/or the operational component C3 to direct the operation of the flow controllers H3 (e.g. the open/closed states of the flow controllers H3 of the TCFA for directing fluid in the internal fluid pathways of the TCFA as well as through the catheters 194*a,b,c* and 196. The TCFA can also have a sensor component C7 for communicating with the various sensors H2 that are contained within the TCFA for fluid monitoring purposes (for example), in the pump 6 for fluid monitoring purposes (e.g. reservoir R#1 fill states), and external to the TCFA and pump 6 for monitoring environmental conditions and fill state of the fluid sources connected via the fluid connection 192. The component C7 can be in communication with the processor component C1 and other components Cn as desired. The TCFA can also have a database component C8 for coordinating access to the databases 322 via the processor component C1. It is recognized that the above described example components Cn can be as shown or the functionalities of such can be combined or reconfigured as apparent to one skilled in the art.

Figure 14:
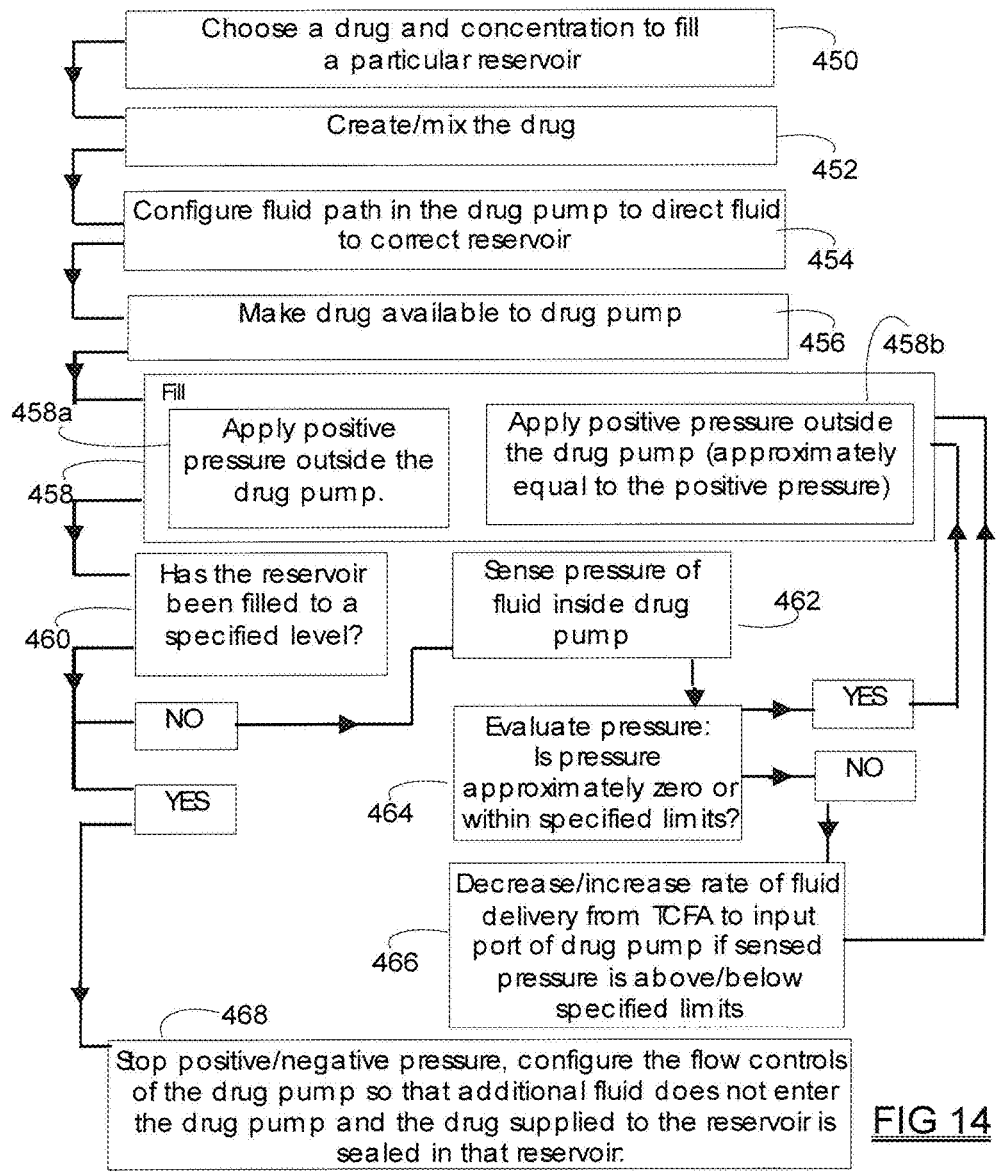

The TCFA, which is shown in FIG. 10, allows users to perform specific steps in testing/calibration/and filling operations using, for example, software routines, physical knobs, dials, and switches rather than requiring users to rely upon strictly manual means. For example, simply running a "fill reservoir #1 with Drug A" software subroutine of a TCFA software program, the processor component C1 can achieve the same result as manually performing 10 operations. For example, referring to FIG. 14:

Step 450 Choose drug A to fill a reservoir which in this case is reservoir #1: The user designates what drug should be supplied to the drug pump 6 by the TCFA by interacting with an input/output component C2 which permits the user to select a drug from a selection of drug options T6 (e.g. the list of drugs can be displayed in a software program), a diluent from a list of diluent options, and a concentration from a list of concentration options, these options being obtained from a list of available drugs from a database component C8 and displayed to the user via the display H8. The user's choices are sent from the input/output component C2 to the processor component C1, which will operate the other components Cn of the TCFA to achieve the filling operation chosen by the user; Step 452 Obtain/mix the drug: The processor component C1 directs the fluid input component C4 to provide the drug which will be supplied to the drug pump 6. If the drug is not available at the correct concentration, the fluid input component C4 may control a mixing element (one of the flow controllers H3) of the operational component C3 to provide the required drug. For example, a mixing element of the operational component C3 obtains a specific drug and a specific diluent which may be contained within reservoirs H4 of the TCFA190, and mixes these in order to obtain the concentration of the drug (the "desired drug") which will be used in a reservoir R#1 of the drug pump 6. It is recognized that the flow control component C6 could be used to operate the mixer element and the sensor component C7 could receive signals indicating the parameters of the mixing operation through appropriate sensors H2; Step 454, Configure fluid path in the drug pump 6 to direct fluid to correct reservoir R#1,2: The processor component C1 directs the flow control component C6 to send control signals to the fluid flow controller 20 of the drug pump 6 (e.g., the control apparatus 22 changes the states of flow controllers 20 in the case of the DDS) to cause fluid to flow into reservoir #1 of the drug pump 6 (e.g., flow controller 20*r* of the inlet port connection means 18*r* and flow controller 18*a* of reservoir #1, shown in FIG. 1*a*, are set to "open" state). In other words, the fluid paths in the drug pump 6 are configured via the various flow controllers 20 (through the processor component C1 and the component C6) to direct the input fill fluid to the proper reservoir R#1,2. It is recognized in the case of the DDS as pump 6, the component C1 would be in contact with the CA 22 to direct the DDS to configure the controllers 20 of the DDS. It is recognized that the internal fluid paths of the TCFA would also be configured in cooperation with those of the pump 6 via controllers H3 to direct the input/output of fluid via the correct ports 194*a,b,c* and 198; Step 456 Make the drug available to drug pump 6: The processor component C1 directs the fluid input component C4 to measure the filling and can also fill the dual lumen TCFA fluid delivery catheter 196 with the desired drug obtained from the fluid source so that the drug is available at the distal dip of the delivery catheter 196. It is recognized that the component C4 could interact with the sensor component C7 to receive signals indicating the fluid parameters (values) of the filling operation through appropriate sensors H2; Step 458*a* Apply positive pressure outside the drug pump. The processor component C1 directs the fluid input component C4 to pump fluid through the TCFA fluid delivery catheter 196 as well as measuring fluid values of this fluid such as the volume, flow rate, pressure, and color of this fluid, and to create a specific positive pressure to cause the fluid in the catheter 196 to enter the input port 24 of the drug pump 6. This step may occur slightly before step 456 so that the input port 24 and catheter 196 are "flooded" with the drug which is to fill the specified reservoir R#1,2 rather than residual fluid from a prior filling, priming, or drug delivery operation; Step 458*b* Apply negative pressure inside the drug pump 6 which approximately equal to the external positive pressure. The processor component C1 directs input/output component C2 to send a control signal via the communication link 202 which causes the pump 23 of the selected reservoir #1 to be operated in a reverse manner in order to draw the drug into reservoir #1 of the drug pump 6. The input/output component C2 can send the control signal directly to the drug pump using the power/communication cable 202, by telemetry, or indirectly by communicating with an external patient controller; Step 460, Determine that the reservoir is filled to a specified level and halt positive and negative pressure causing fluid to flow for filling the reservoir: the sensor component C7 senses via sensors in the pump 6, for example through the CA 22 if the reservoir R#1 has been filled to a specified level. The processor component C1 determines that the reservoir R#1 is filled to a specified level and if so, tells the fluid input component C5 to stop the delivery of fluid and orders, via the input/output component C2, the drug pump's 6 control apparatus 22 to stop operating the pump 23 in a reverse direction. The processor component C1 may determine that the reservoir R#1 has been filled to a specified level from the sensor component C7 which receives sensed data from a pressure, volume, or flow sensor, or other sensor, in the drug pump 6 and determines that this data indicates the reservoir R#1 is full or from the sensor component C7 which receives sensed data from a pressure, volume, or flow sensor, or other sensor, in the fluid input component C4 of the TCFA and determines that this data indicates that enough fluid has been supplied to the drug pump 6 that the reservoir R#1 is full, the volume of the reservoir R#1 being obtained either from the database component C8 or supplied by the user who inputs this information by the input/output component C2, for example, by pushing a button. The filling operation can be halted in a slower manner where decreases in the flow rate of the fluids continues until the fluid has stopped flowing (e.g. the rate of filling decreases as the reservoir is filled from 95% to 100% of its capacity so that the rate reaches zero at 100%). The user can also use the input/output component C2 to increase or decrease the rate of flow or halt the flow of fluids being used to fill a reservoir R#1. If the reservoir R#1 is filled, then the operation proceeds to step 468 as further defined below, otherwise step 462 is done to sense the pressure of the fluid inside the drug pump 6 using the sensors in the pump 6 via the CA 22 to provide pressure signals to the component C7 via the component C2; Step 464 Measure that the negative and positive pressures are approximately equal. If the drug pump 6 has internal pressure sensors which are able to sense pressure, then the sensor component C7 can communicate with the sensors of the drug pump 6 through the input/output component C2 and determine if there is positive or negative pressure in the drug pump 6. a negative pressure that is equal to the pressure of the fluid being supplied by the TCFA, the pressure sensors should sense relatively low pressure. The sensor component C7 can determine if pressure is above or below a specified level at step 464, then the sensor component C7 can provide adjustment information to the processor component C1 which either adjusts at step 466 the pressure of the fluid supplied to the drug pump 6 or directs the input/output component C2 to send a control signal (for example via the CA 22) to operate the pump 23 of the reservoir #1 in order to decrease this pressure. If the pressures are within tolerance, then steps 458*a,b* and 460 are repeated, otherwise step 466 is completed and then steps 458*a,b* and 460 are repeated; Step 468 Configure the flow controls 20 of the drug pump 6 so that additional fluid does not enter the drug pump 6 and the drug supplied to reservoir R#1 is sealed in that reservoir. If step 460 indicates a filled reservoir R#1, then the processor component C1 directs at step 468 the flow control component C6 to send control signals to the fluid flow controllers 20 of the drug pump 6 (e.g., via the control apparatus 22 to change the states of flow controllers 20) to inhibit additional fluid from entering the drug pump 6 and sealing the drug supplied to reservoir #1 within that reservoir (e.g. for the DDS the 18*r* and 20*a*, of FIG. 1*a* are set to "closed"). Once the reservoir R#1 is filled, purging of the supply catheter 196 can be done so that it is ready to receive the next drug to be supplied to the drug pump 6 for the next reservoir R#2, if desired. For example, the processor component C1 directs the fluid input component C6 to purge a dual lumen TCFA fluid delivery catheter 196 with an inert fluid and clears out the previous filler drug fluid.

Rather than 10 operations, as is described in this simple example, filling the drug pumps 6 with, several drugs can require several hundred operations, which may require several hours to perform manually. The TCFA can operate according to software routines that enable it to function completely automatically (e.g., in a closed loop configuration) or semi-automatically, where specific steps of multistep testing/calibrations/and filling operations occur automatically (e.g. fill reservoir #1 with drug A), but are done in conjunction with intervention from a user and/or allow the user to modify TCFA operation in real time (e.g., decrease speed of filling reservoir #1 by 25%). During calibration and testing of delivery regimens, rather than using the drugs themselves, other fluids can be used. These fluids can be mixed with dyes or chemicals which enable their identification as they pass through the sensors located at various locations in the drug pump, catheters, and the TCFA. Additionally, the TCFA can mix the dyes with the drug which will be used during drug delivery so that optical sensors in the drug pump can determine the presence of various drugs located in its internal components.

The TCFA programming software contains checks for providing that the drug regimen doesn't include incorrect infusion parameters, such as incorrect rates, volumes, concentrations, doses, or mixtures due to, for example, the interactions of different drugs. This can be accomplished, in part, by checking the values chosen by a user against a table contained in a database T1-Tn of the TCFA which contains other information such as the age and weight of a patient and ensures that the drug regimen is not dangerous to the implantee. The database T1-Tn of the TCFA can also contain, for example, software routines which enable previous user designed drug regimens to be realized by a specific type of drug pump model, transformation values to transform drug regimens made for one drug pump model into regimens appropriate for a different model, regimens provided from the manufacturer for different drug pump models, treatment regiments for various types of drugs, information about the drug pump make or model, a drug pump ID#, serial numbers of the DDS and its catheters, drugs, information entered by TFCA users, and software routines for performing tests such as flow rate tests, occlusion pressure tests, and other tests for different drug pump embodiments. All information and software routines located in the TCFA and drug pump databases T1-Tn & 322 may be shared between these two devices. The drug pumps can send error signals to the TCFA when components malfunction, or the TCFA can generate an error message when the flow of fluids deviates from what it expects, indicating that one or more pump 6 components are not operating correctly.

It is recognized that the database T1-Tn b can be located within the TCFA or located remotely (such as but not limited to the database of the DDS), or a combination thereof. The TCFA also is coupled to a fluid source either directly (as shown in FIG. 10) and/or indirectly (not shown) such that the fluid input component C4 monitors the fluid contents of the direct fluid connection between the fluid source and the input port 24 of the DDS. Further, it is recognized that the TCFA components can be embodied as hardware, software, or a combination thereof.

The performance of drug delivery systems can be greatly improved when these are filled correctly. For example, the TCFA can help to decrease the risk that air pockets will enter the internal components during the filling operations. Further, by enabling DDS operation to be tested, differences can be determined by the processor component C1, which exist between different systems, can be compensated for empirically by adjusting the Fluid Volume reference table St4 of the database 322 of the drug pump (and/or drug pump database table T3 of the TCFA) to be adjusted to account for these differences. For example, the amount of buffer fluid which must be released, prior to a bolus amount of drug being pushed through the distal tip of a catheter, can be measured and a correction factor representing the difference between the standard volume (as provided in the manufacture's specifications) and the empirical volume needed for this operation can be stored in the database 433 of the DDS (or otherwise programmed by the flow control component C6) to enable the DDS to operate in a specified manner in several of its modes. In many applications a surgeon may use different lengths of output catheters 194*a,b,c* made from different materials and these types of empirically derived measurements (which can serve as correction factors) will be essential. Further, when using multiple drugs, the TCFA can be used since filling of the DDS without a TCFA might be difficult and time consuming even for trained personnel. Additionally, mistakes made while filling the TCFA can greatly hinder performance once the DDS is implanted.

The database Tn contains tables that assist the TCFA in performing its operations. The database contains an empirical/expected table T1 which contains the empirical values of the drug pump pumping operations and capacities, which are empirically derived during calibration operations and during testing of the drug pumping operations, and the expected values, which can be provided by the manufacturer. During calibration the TCFA can produce a series of calibration correction factors coordinated by the processor component C1 which it then sends to the drug pump 6 so that the actual pumping operations produce the desired results, as described above. The TCFA then tests the drug pump 6 and determines if the differences between the empirical and expected values are below some specified amount (e.g. 1% error), and if not it may perform the calibration again. Alternatively the TCFA may adjust the drug delivery regimen that it downloads into the drug pump according to these correction values. The database can also contain a lengths/volumes table T2 which contains the lengths and volumes of the catheters which are to be used. The values in the lengths/volumes table can be input by the surgeon depending upon how the drug pump 6 will be used, and can be useful in creating correct drug delivery therapies, especially if the lengths of the catheters used during calibration and testing of the drug pump are different than those that will ultimately be implanted. The lengths and volumes table is also important to create a drug delivery therapy that will accurately deliver drugs from the tip of the catheter or which will use flow recirculation modes, wherein information about the catheters. The drug pump database table T3 can contain all information located in the database 322 of the drug pump 6, including what drugs, concentrations, and residual volumes are currently within the drug pump 6 (which is very useful when refilling a drug pump 6 that has already been implanted). The routines/protocols table T4 contains values used during the TCFA operations including the correction factors from the empirical/expected table T1, user defined (i.e., custom) correction values, and other values used to modify and adjust the TCFA operations as determined by the processor component C1 by the software program of the TCFA. The model values table T5 contains values related to simulation models which the TCFA uses to iteratively adjust the TCFA operations to minimize amounts of error in delivery operations of the drug pump 6. The model values are also useful when the user wants to design new drug delivery protocols which will be sent to the CA 22 of the drug pump 6 and allow for, for example, sending a specific concentration of a drug from a particular catheter after it has been mixed with a dilution fluid. Accordingly, the model values table can work with modeling software in the TCFA software program of the component C1 to enable the creation of customized delivery regimens specific to an individual needs of the implantee. The model value table T5 can work with the drug pump database table T3 in order to send fluids to an implanted pump 6 which has a specific amount of residual drug in each of its different reservoirs. For example, if there are 3 reservoirs which are 10%, 30%, and 20% full, then the TCFA should send a sequence of fluids to the drug pump 6 which corresponds to approximately 90%, 70%, and 80% of the total reservoir volumes in order to fill these reservoirs. Delivering more or less than this amount may cause the drugs supplied by the TCFA to enter into the wrong reservoirs, or may cause other types of problems during the refilling process. The patient/drug table T6 can contain information such as the age and weight of a patient that can be accessed by the software program for use in calculations which ensure that a drug delivery regimen is not dangerous to the implantee.

Prior to implantation in the patient, the drug pump 6 should be calibrated and tested. Using complex drug delivery regimens needs the calibration and testing of both specific operations and also series of operations that combine to allow for the regimens to occur. For example, not only should fluids be measured as these are dispensed from reservoir #1 and reservoir such as by the fluid output component C5, but drug delivery regimens which require the two drugs to be delivered sequentially and simultaneously should also be tested to detect any changes that occur during either of these operations, a consequence of such as but not limited to the sharing of internal fluid passageways of the drug pump 6 by the two or more drugs. The testing and calibration of the pump 6 can occur using automated routines of the processor component C1 in cooperation with the other components of the TCFA. For example, a test (which could be included in multiple test battery of a software program) could comprise iteratively filling all the reservoirs a number of times and dispensing fluids via a set of pathways according to delivery regiments which would be used during the treatment of the implantee. This transfer of fluids to and from the pump 6 is monitored by the fluid input and output components C4,C5. During each iteration the empirical values for TCFA measurements of the delivered fluids are recorded by the respective components C1-Cn, and the processor component C1 compares to the desired values stored in the database T1-Tn, and correction values are automatically generated by the processor component C1 which are used in the subsequent iteration (e.g., by subtracting the measurements of the delivered fluids from the desired fluids to obtain the differences which are used as correction factors). This process is continued by the processor component C1 in cooperation with the other components C2-Cn until the differences between the empirical values and the expected values are within a certain range. The expected values can include manufacturer drug pump 6 specifications and/or patient drug delivery requirements, which can be stored in the database T1. The correction factors can then be used to modify the drug delivery routines of the drug pump 6, including programmed operation of the flow controllers 20, and can be stored in the database 322 of the drug pump 6 or the database T1-Tn of the TCFA. This iterative process can also be done due to variations between how the pump 6 will function for different patients, who may require unique differences such as the lengths and internal volumes of the catheters (and internal lumens) to be used, the number of catheters which will be used, and other variations.

The TCFA 190 is shown in FIG. 10. The TCFA can contain means to pump fluids into the DDS which may include for example, internal pumping means, reservoirs, flow control means, and flow/pressure sensors. Alternatively, the TCFA may be realized in a more distributed design where the different hardware components (e.g., pumps and reservoirs) are located outside a single housing, and, for example, are under control of the respective components C1-Cn of the TCFA, namely the input component C4, the output component C5, the flow control component C6, and the sensor component C7. In a distributed embodiment, the TCFA can send or receive fluid through one or more TCFA catheters 192.

The TCFA can receive fluids from any of the catheters of the drug pump 6, via the TCFA input ports 194$a,b,c$, which may be transparent and which may have markings which indicate volumes contained along the lengths of the ports, to which the distal ends of the catheters (or lumen) may be attached. During TCFA operations, testing catheters which may have similar volumes to the catheters which will be used during actual drug delivery, but which have different types of sensors which assist in conducting the TCFA operations, may be used. The testing catheters can be transparent so that fluids traveling through them can be viewed by user and may be usefully labeled with measurement marks (e.g., the marks are distances equivalent to 1 ml spacing) so that fluids traveling through the catheters can be visually evaluated. It is recognized that these manual measurements can be supplied to the input/output components C2 via user input to the TCFA. Additionally, when performing TCFA operations on a pump 6 which will use concentric multi-lumen catheters when implanted, the concentric multi-lumen catheters can be substituted with individual catheters which have equivalent volumes, and which can be individually connected to different ports 194$a,b,c$ of the TCFA. The TCFA ports can also be configured to accept specialized catheters such as concentric multi-lumen catheters. The TCFA can also have at least one outflow catheter 196, which transmits fluids from at least one TCFA outflow port 198 to at least one replenishment means, which is realized here as an inlet port 24 of DDS 10. It is recognized that the TCFA outflow component C5 could be coupled to a catheter (fluid connection) directly connected to the fluid source. Alternatively more than one outflow catheter 196 can be connected to more than one inlet ports 24 contained in the pump 6. Further, rather than having a single lumen, the catheter 196 can contain two or more lumens and catheter flow control means to control the flow of fluids within these lumens and to control flow of fluids from these lumens into the pump 6, as shown in FIGS. 7$a$-$d$. Accordingly, the TCFA can operate in a fluid recirculation mode, wherein fluids are circulated within the lumen of the catheter 196 until a desired fluid is adjacent to replenishment means of the pump, as described above with reference to FIG. 8 of the dual lumen catheter. Next, the TCFA and pump 6 are both operated to cause this fluid to enter into the pump 6. It is recognized that the pertinent components of the TCFA, as described above, are used to configure operation of the pump 6 during the specific mode (such as but not limited to initialization, calibration, testing, and filling) of the TCFA. Further, when delivering more than one type of fluid to the pump 6, using the fluid recirculation mode enables the catheter 196 to be flushed between delivery of different fluids to the pump 6.

A power/communication means such as a power/control cable 202 can bring both power and control signal from a TCFA control/power output plug 204 of the TCFA to an input plug 206 on the pump 6. Even though the implantable pump 6 has its own power means, and can have telemetry capability for assisting in (e.g., synchronizing, coordinating) the TCFA and pump 6 operations through the flow control component C6, the power/control cable 202 is useful since when performing TCFA operations it may be advantages not to deplete the internal power means of the pump 6. Alternatively, the power/control means can be incorporated into the outflow catheter 196 and the pump 6 replenishment means can be configured to receive the power/commands from the catheter (and send these to the control apparatus 22 of the pump 6) so that only one connection is made between the TCFA and pump 6 (as would be beneficial when the pump 6 has already been implanted). During operation of the TCFA, the pump 6 may be partially implanted in a patient or may be submerged in a tank 208 of saline or other fluid. The tank 208 may be heated to body temperature either by the TCFA, for example, by a servo controlled hot plate or other heating means. In the embodiment shown in FIG. 10, the pump 6 is shown with three catheters 80 of different lengths attached, at their distal tips, to the TCFA. Further, the outflow catheter 196 and power/control cable 202 enable fluid and electrical communication between the TCFA 190 and pump 6, and the TCFA 190 sits on top of the tank 208 with two positioners 210a, 210b which provide a secure connection between the TCFA 190 and the tank 208. A viewing chamber 212 is shown, which is one of several that can be provided in the TCFA, so that gas or fluid traveling through the pump 6 catheters 80 and into the TCFA can be viewed.

As fluids from the DDS are pumped through a catheter from the pump 6 output port and into the TCFA through one of the TCFA catheter input ports 194 the output fluid can be sensed by sensors 21 & H2 which communicate with the sensor component C7, such as but not limited to pressure/flow/optical/chemical sensors located in the pump 6 and/or in the TCFA. Additionally, the TCFA may exert a variable amount of resistance upon the fluid, under direction of the input/output flow components C4,C5, which enables the TCFA to approximate resistances that may occur in the body of the implantee (due to, for example, pressures of fluids or rates of flow in the drug delivery targets) Further, the fluids can be directed into holding reservoirs to hold fluids sent back into TCFA from the pump 6, into the reservoirs R#1,2 from which they were originally dispensed can be re-deployed to the pump 6, can be purged into waste reservoirs, or can be sent through extended catheters, which may be transparent, so that the history of all the fluids which have been pumped can be visually examined. When there are sensors in the pump 6 (coupled to the sensor component C7) which sense the internal operational states of various components of the pump 6 (e.g., a reservoir R#1 is full) or in the calibration catheters, the values from these sensors can be sent from the pump 6 to aid in TCFA analysis by the processor component C1.

The TCFA can operate in several modes (i.e., according to software routines) such as initialization, calibration, testing, and filling. Some illustrative examples of these modes are as follows. An example of initialization mode occurs when the fluid output component and flow control component C5,C6 coordinate the provision of fluids, such as buffer fluids which can be used to "prime" the pump 6, through all the fluid containing components of the implantable pump 6. Each of the DDS fluid reservoirs can be selectively filled sequentially by having the flow control component C6 send commands to the pump 6 for operating its flow controllers 20 (such as valving and/or pumps) in accordance with the fluids delivered as monitored by the output component C5. An initialization procedure may include several steps, such as 1. filling each of the reservoirs, connection means, and catheters, 2. completely emptying each reservoir by operating the associated pump 6 in the forward direction, 3. re-filling each reservoir by operating the associated pump 6 in the reverse direction, where steps 2 and 3 are repeated several times (i.e. iteratively) in order to reliably flush, for example, gas from the pump 6 internal fluid passageways and fluid reservoirs and to test the general operation of the pump 6 components.

In a calibration mode, the individual flow controllers 20 of the pump 6 are each operated according to a set of calibration tests (in cooperation with configuration signals supplied by the flow control component C6) and the amount of input/output fluids as monitored by the respective components C4,C5, such that the input/output fluids in respect to the DDS are measured in order to calculate the fluid volume, pressure, and/or flow rates through each catheter when one or more pumps 23 are activated. It is recognized that the processor component C1 in cooperation with the sensor component C7 and the input/output components C4,C5 are used to determine and record the amount and operational state values of the pump 6. It is recognized that the amount value can include volume, weight, and/or flow rate of the input/output fluids. The user can also assist in the calibration operations. For example, if the fluids include dyes so that an operator can visually detect the presence of a fluid, then when a particular color of fluid enters a viewing chamber 212, the operator can enter this change into the processor component C1 and/or respective input/output component C4,C5 indicating, for example, a fluid has been dispensed from the distal tip of a catheter. Both the fluid used during calibration as well as the fluid used during normal pump 6 operation may have dye added to produce specific colors for specific fluids. In addition to aiding a technician using the TCFA, in identifying fluids due to these unique colors, the DDS may also contain optical sensors coupled to the sensor component C7 which can be used to identify fluids by the color of the fluid while it is proximate the sensor. Alternatively, instead of, or in addition to using different dyes, chemical sensors coupled to the sensor component C7 can be used which automatically detect the presence of one or more fluids used during the calibration procedures. By using 2 or more non-miscible liquids during the testing procedure, the user can enable the processor component C1 to determine the empirical fluid capacities of different components of the pump 6 so that differences between the manufacture's specifications and the actual operational fluid capacities and fluid dynamics of the pump 6 can be determined, and used to adjust pump 6 operation to optimize drug delivery. It is recognized that the recorded values can be stored in the database T1-Tn, along with the manufacturers specifications and patient drug delivery requirements.

In testing mode, the TCFA controls the pump 6 according to data collected in the calibration mode and which has been updated in the databases T1-Tn & 322 (i.e., the Fluid Volume tables) of the pump 6 and/or TCFA. Using this operational information, the processor component C1 coordinates the operation of the different reservoirs of the pump 6, through the flow control component C6, using a series of testing routines in order to ensure that the pump 6 is operating correctly. The testing mode may test the implantable pump 6 in continuous fashion mode, a bolus mode, a flow return mode, a replenishment mode, and an implantee refilling mode, and in other modes. In a testing mode, the processor component C1 and the flow control component C6 may control the pump 6 to sequentially send specific amounts of fluid from Res1 to a series of catheter hubs, and then may repeat this test when fluid is also sent from Res2, in order to insure that the delivered fluid has the correct flow rate, pressure, volume, and drug concentration, as sensed via the sensor component C7.

In filling mode, the pump 6 is filled with the input fluids, via the fluid output component C5 of the TCFA, that the pump 6 will use during drug delivery. For example, an inert fluid may first be used to completely clear the pump 6 of all testing fluids (the filling mode may begin by invoking an initialization routine which primes the pump 6) and then each reservoir, connection means, and even catheters are independently filled with the appropriate fluids to be used after implantation. When the filling operations are complete, the pump 6 is ready to be inserted into an implantee. This TCFA can also be operated in filling mode after the pump 6 is implanted in an implantee to refill the reservoirs of the pump 6. The filling mode can also include transmitting the software routines, with the final values which have been obtained during the calibration/testing procedures, from the TCFA to the pump 6.

The feedback component C2 of the TCFA can contain notifications and/or checks for ensuring that the drug regimen doesn't include incorrect infusion parameters, such as incorrect rates, volumes, concentrations, doses, or mixtures due to the interactions of different drugs. This can be accomplished, in part, by checking the values chosen by a user against a table contained in the database of the TCFA which contains other information such as the age and weight of a patient and ensures that the drug regimen is not dangerous to the implantee. The database of the TCFA can also contain, for example, a list of software routines and customized values which enable previous user designed drug regimens to be realized by a specific type of pump 6 model, transformation values to transform drug regimens made for one pump 6 model into regimens appropriate for a different model, regimens provided from the manufacturer for different pump 6 models, treatment regiments for, various types of drugs, information about the pump 6 make or model, a pump 6 ID#, serial numbers of the pump 6 and its catheters, drugs, information entered by TFCA users, and software routines for performing tests such as flow rate tests, occlusion pressure tests, and other tests for different pump 6 embodiments. All information and data related to user modifiable variables in software routines located in the TCFA and pump 6 databases may be shared between these two devices. The pump 6 can send error signals to the feedback component C2 of the TCFA when the pump 6 components malfunction, and feedback component C2 can generate an error message to the user of the TCFA when the flow of fluids deviates from what it "expects", indicating that one or more pump 6 components are not operating correctly.

Some modern drug pumps 6 are realized in the form of microchips. Further, in some embodiments of the pump 6, microchip drug delivery circuits may also be incorporated into the pump 6 catheters as was described previously. Like the pump 6 embodiments described in much of this specification, the microchip drug pumps can store different substances or concentrations of substances. For example, a pump 6 can be implemented in a microchip such as those being developed by Microchips Inc (see US pat application 2003/0105455 by Santini). Current microchips are designed as a series of reservoirs or "wells", each of which is reversibly "capped" with a reservoir cap which can oscillate from an "open" or "closed" state depending upon, for example, an electrical charge applied to the cap. Accordingly, in an alternative embodiment of the TCFA can be used in order to perform TCFA operations on the microchip pump 6. The TCFA, is modified so that it could operate with a miniature drug pump which has a series of miniature "wells" which store fluids in order to control fluid flow to a particular well, set its "cap" in an open position, fill the specified well, and functionally "close" the cap. With very small wells, though injection is a preferred method of filling the wells, the wells can be filled individually by capillary action, by molecular/chemical/electrochemical binding, by pulling or pushing the material into the wells using a vacuum or other pressure gradient, by mechanical, electrochemical, or electromechanical means, or by any combination of these or similar well filling techniques. When the wells of the microchip are small enough, these can be refilled with very small amounts of fluids, and even molecules, and the TCFA is able to remove the residual fluid from the microchip DDS which was not used in filling these wells. The TCFA can also test the operation of the microchip, for example, it can test the operation of any well "caps" or pumps which were included on, or which worked in conjunction with, the microchip, and can be used to test any sensors included on the microchip, and calibrate the microchip pump 6 so that it may accurately be used with any external pump and catheter systems which may be incorporated for drug delivery to distal targets.

The different modes in which the TFCA operates can include different groups of software commands or routines used in combination with the various components C1-Cn as described above. In general, TCFA operation can be controlled by software routines which include low level commands and higher level commands. Low level commands include such choices as deliver 30 ml to pump 6, set a specified flow control to the open state, etc. and provides warnings, for example, if a user attempts to deliver drug to the pump 6 and has not provided a path by setting the appropriate flow control to the "open" state, then the action does not occur and a warning is issued. Higher level commands include such commands as "fill reservoir #1 with drug X which should be diluted to concentration Y", "purge reservoir 1 fluid from pump 6 through catheter #2", "run calibration test on all reservoirs", and can include commands that cause entire software routines to execute, such as "calibrate pump 6" which performs entire calibration procedures automatically, etc. The software that runs the TCFA can be based on a command language, can be graphically based which may include table based commands. For example the following table could be used to fill the pump 6 for the first time:

| Order | Component | Function | Amount | Fluid | Concentration |
|---|---|---|---|---|---|
| 1 | All Reservoirs | Calibrate | ALL (5 ml) | Buffer | .01 mg/ml |
| 2 | All Reservoirs | Purge | ALL (5 ml) | Buffer | .01 mg/ml |
| 3 | Reservoir #1 | Fill | ALL (5 ml) | Buffer | .01 mg/ml |
| 4 | Reservoir #2 | Fill | 4 ml | Drug #5 | 1. mg/ml |
| Etc . . . | Etc . . . | Etc . . . | Etc . . . | Etc . . . | Etc . . . |

One example of the method of filling would entail the following steps:
- a. attaching the replenishment means to the pump 6 TFCA using an external fluid source connector containing at least two lumens,
- b. operating the pump 6 TFCA to flush the external fluid source connector with an inert fluid,
- c. operating the pump 6 TFCA to fill the external fluid source connector with a fluid which is to be stored within the pump 6,
- d. operating the flow controllers of the pump 6 and the pump 6 TFCA to cause desired fluid to enter a specific reservoir, and
- e. iteratively repeating steps b and c until the pump 6 is filled in step d, the pumping means 23 of the pump 6 can be operated to create a vacuum pressure that is equivalent to the positive pressure exerted by the TFCA so that pressure gradients are kept below a specified level during refilling.

Some systems/devices for testing the operations of medical drug delivery instruments and drug pumps 6 are already commercially available. For example, the DALE4100 Infusion Device Analyzer or the DNI Nevada Infutest 2000 are instruments which allow testing and measurement of infusion pump output only including, for example, flow rate, volume, occlusion/pressure measurements related to steady, non-bolus testing, bolus delivery with or without a basal-rate rate superimposed, and dual/multi rates. Further, the IDA-4 Multi-Channel Infusion Device Analyzer allows analysis of 4 channels of fluid output from one or more devices to be measured simultaneously with accuracy of +−0.1% at flow rates between 50 and 100 ml/hr and +−0.2% at all other flow rates. While these devices assist in testing of medical drug delivery instruments and drug pumps 6 (although these are not implantable), they only receive fluids from the instruments being tested and do not provide one or more fluids to the drug delivery system for purposes of testing, calibration, filling or refilling. None of these devices allow for the drug pumps 6 which are able to hold multiple fluids to be refilled by ensuring that different fluids are routed to the different areas of the pumps. None of these devices enable the iterative adjustment of the drug delivery operations until the error of delivery is reduced enough to approximate achieving a desired regimen. None of these devices communicate with the internal components of the drug pump 6 in order to cause them to operate so as to minimize pressure gradients during refilling operations as would be beneficial during the refilling of a drug pump 6 once it is implanted in an implantee. None of these devices utilize colored fluids and optical sensors to calibrate and test the operation of the pumps. None of these devices utilize chemical sensors to test which of several drugs is being pumped as can occur when multiple drugs are used, when multiple catheters are used, and when multiple drugs are delivered through the same catheter. None of these devices utilize a dual-lumen catheter for delivering fluids to the drug pumps in a manner that permits greater control over the fluids being sent to the drug pumps 6, which can be important when these drug pumps 6 are implanted.

DDS Implantation and Replacement

From time to time the DDS 10 may have to be replaced due to malfunction, or for filling or upgrade purposes. It may be inefficient to remove the catheters, sensors, and stimulation leads which were previously implanted by a surgeon when replacing the DDS and subsequently requires a surgeon replace these. Further, when the catheters and or stimulation leads are implanted in an area such as the brain, removal and replacement may decrease the therapeutic effect because the new stimulation leads or catheters may not reach the same area. Alternatively, the catheters can be removed from the DDS catheter hubs and used with the replacement DDS, but this is difficult when the catheters contain electrical leads and also may decrease the security of the connection between the catheters and the catheter hubs. Accordingly in one embodiment of the DDS it is configured to function with a multiple catheter hub connection assembly (CHCA) 400. The multiple CHCA 400 allows the catheters, sensors, and stimulation leads to remain implanted and greatly facilitates replacement of the DDS.

FIG. 12a shows a DDS 10 and a multiple CHCA 400. A customized top 12a formed into the housing of the DDS is configured to receive the multiple CHCA 400, which is removably secured by means of a DDS fastener 404a which interlocks with the CHCA fastener 404b and is set in an "unlocked" state during replacement and a "locked" state after implantation (more than 2 fasteners can be used). The state of the CHCA fastener 404b can be determined electronically by, for example, the DDS control apparatus, or can be physically determined by the user, for example, by squeezing or snapping/unsnapping the fastener 404b. The customized top 12a also includes a power/communication connection 408a which is connected to the control apparatus 22 makes functional contact with a power/communication connection 408b of the CHCA 400. The power/communication connection 408b, in turn, is individually connected to the electrical means 90 of each catheter hub via CHCA circuitry 412a-c which can be embedded in the CHCA 400. When the CHCA 400 is attached to the customized top 12a of the DDS the catheter hubs of the DDS 16a-c interlock with the catheter hubs of the CHCA 16a"-c". During drug delivery the flow controls for the catheter hubs of the DDS 44a-c and the flow controllers for the catheter hubs of the CHCA 416a-c (note: 416b not shown) may be in an open or closed state depending upon the drug delivery regimen of the DDS. However, during replacement flow controls 44a-c and 416a-c are set in a closed state so that fluids do not leak out of the DDS 10 or the catheters. In addition to the external sensor connection means 28 of the DDS 10, the CHCA 400 may have an external sensor/stimulator connection means 424, which is functionally connected to the power/communication connection 408b of the CHCA 400 which can communicate with and supply power to external sensors and stimulators so that, like the catheters, these do not have to be replaced during DDS replacement. In the embodiment shown in the figure a multiple CHCA 400 has several catheter hubs. Single CHCA embodiments are also possible so that each catheter hub 16a-c of the DDS receives a single CHCA. Alternatively, as is shown in FIG. 12b the catheters can be divided into a proximal segment which is connected to a catheter hub of the DDS 10 and a distal segment which delivers the fluids to the implantee. The proximal segment contains a proximal segment connector 420a which securely connects to a distal segment connector 420b. Like the CHCA 400 of FIG. 12a, the segment connectors 420a and 420b have fasteners 404c,404d which can be set in their "closed state" to cause the connectors 420a and 420b to stay connected, and which can be set in their "open state" during replacement operations (the state change occurring either electronically or by the physical intervention of a surgeon). In other embodiments, the connectors can also be attached by being screwed together, clipped together, kept together using an external fastener or otherwise attached. Connectors 420a, 420b and also have power/communication connections 408c and 408d, respectively, which maintain power/communication continuity between the proximal and distal segments of the catheter. Additionally, like the CHCA 400 of FIG. 12a, the proximal and distal segment connectors 420a, 420b contain flow controls 416c and 416d, respectively, which deter fluids from flowing during replacement operations.

Figure 13:
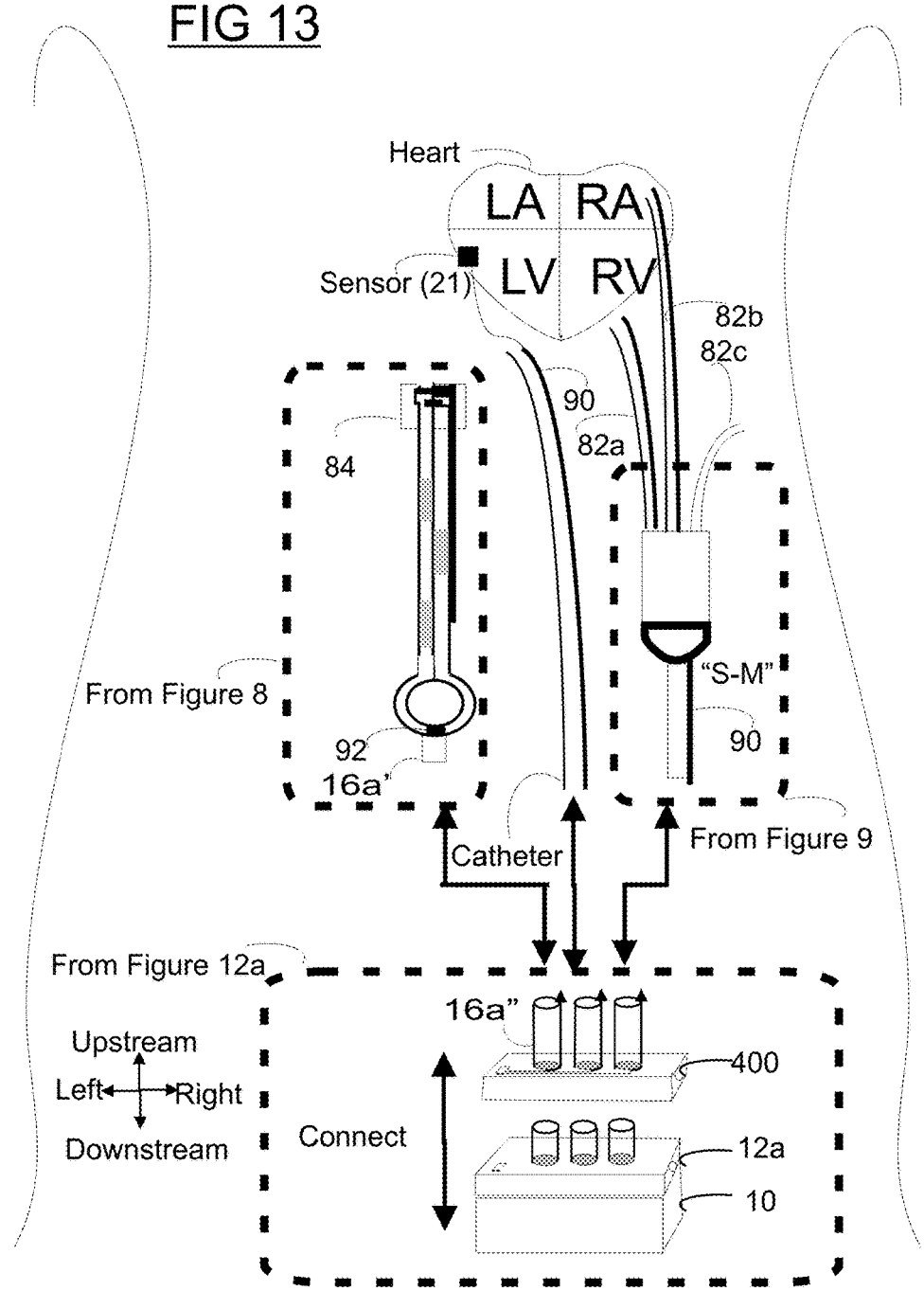
FIG. 13 shows the DDS of FIG. 1a implanted in the body of an implantee.

FIG. 13 one embodiment of the DDS 10, which utilizes some of the components shown in FIGS. 8, 9, and 12a. Since the components illustrated in these FIGs have already been fully described, and labeling all components would make the figure too cluttered, only a few of the components are labeled so that those skilled in the art can identify these components. The DDS 10 is implanted in an implantee and is attached to a multiple CHCA 400 whose hubs are attached to 3 different kinds of catheters which are used to treat the heart of the implantee. The left catheter hub of the CHCA 16a" is connected to a dual lumen catheter which includes a catheter pumping means 92 which can circulate the fluids in a clockwise or counterclockwise manner, and which can draw fluid into the lumen of the catheter from a DDS catheter hub 16a. In FIG. 8 the dual lumen catheter is attached directly to the DDS catheter hub by the catheter hub connection 16a', but here a catheter hub connection 16a' is used to attach the dual lumen catheter to the left catheter hub of the CHCA 16a" of the CHCA 400. The middle catheter hub of the CHCA is attached to a simple catheter which contains a sensor on its distal end that is sensing data from the left ventricle of the heart. The right catheter hub of the CHCA is attached to a single-multiple multi-stage catheter which has 3 lumens exiting from its distal end. Lumens 82a and 82b are configured to deliver fluids to the right ventricle and atrium of the implantee's heart, respectively. Lumen 82c is directed to a distal location where fluid samples can be sent when the DDS operates in a push-sample mode.

Clinical Applications of the DDS

Some characteristics of the drug delivery operations will be similar across many of the different medical treatments. One general method of using the DDS, or other embodiment of a drug delivery device, to treat a medical disorder includes the steps of:
implanting one or more sensors in the body of an implantee
sensing data from one or more sensors to generate sensed data,
processing the sensed data to produce processed data, and evaluating this processed data, using an evaluation routine, and producing either a positive result, wherein drug delivery occurs, or a negative result, wherein drug delivery does not occur.

When drug delivery occurs, it can be accomplished according to a drug delivery protocol. The drug delivery protocol can determine the site, drug, volume, rate, concentration, and type of delivery method (e.g. continuous, bolus, etc). In multiple catheter embodiments, the drug delivery protocol can determine the particular catheter and the site of delivery from that catheter for at least one drug. Additionally, when several catheters are provided, the drug delivery protocol can indicate which of one or more of the catheters will dispense drugs and in what temporal order. When each of the catheters is capable of delivering more than one drug, the drug delivery protocol will also determine which drug should be sent out of each catheter. Delivering a suboptimal dose of a drug, the wrong drug, or a drug to a suboptimal location or set of locations will result in decreased performance and increased rates of depletion of the drugs stored in the DDS. When electrical stimulation leads are also utilized by the DDS, these can stimulate electrically, according to an electrical stimulation protocol, to work in conjunction with the drug delivery to achieve a desired result.

The sensed data can be data sensed by sensors, for example, electrical (e.g., EEG/EKG/EMG), pressure, flow, optical, chemical, and biosensors. The sensors can be configured to obtain signals related to at least one patient. In some applications the patient may be either a mother (taking into account the effects that treatment of the mother has on the fetus) or fetus or both. The processing, utilized to process the sensed data into processed data, can comprise signal analysis, for example, signal averaging, filtering, spectral analysis, wavelet analysis, pattern recognition, modeling and simulation, and may include statistical analysis. Alternatively, the processing may comprise operations as simple as making the sensed data available so that it may be stored as at least one value in a table of the database used by the software program which controls the drug delivery operations. The processed data can be submitted to an evaluation routine and evaluated in order to determine whether a positive or negative result has occurred. A positive result can occur if the evaluation protocol determines that some characteristic of the processed data meets (or fails to meet depending upon the comparison operation used by the evaluation routine) specified criteria. For example, the evaluation of processed data may indicate that the concentration of a metabolite, associated with increased chance of labor, has met criteria which concern a specific concentration level existing for a specified amount of time. The evaluation protocol can include comparing processed data to data stored in a population/normative values table RT3 of the database of the DDS. Rather than using sensed data, the DDS can also deliver therapeutic substances strictly according to a predetermined regimen, which may be approximately continuously, and which may be aimed towards providing prophylactic results.

The medical drug delivery systems and methods described herein can be used in many clinical applications as described in the prior art. Further, some novel applications relating to using this technology to assist in promoting healthy labor and development of the fetus as will now be discussed. These methods can be used with the DDS, or with other, or other embodiment of a drug delivery device (e.g. generic implantable drug pumps), which is capable of similar functions. The systems and methods can be used prior to pregnancy, during pregnancy, or acutely during birth.

The medical drug delivery system can be used to promote a healthy intrauterine environment. The consequences of an unfavorable intrauterine environment can extend throughout the entire life of an individual, may be irreversible, and are of major importance worldwide. While fetal growth and development are determined primarily by the genetic potential of the fetus, these can be strongly influenced by environmental factors, which can exert stimulatory or inhibitory effects. When the fetal environment is abnormal, the fetus may not develop normally, and while some compensatory mechanisms may be available, these compensations may also lead to abnormal development and medical disorders. In order to obtain its supply of nutrients, the fetus depends on the nutritional status of the mother and the capacity of the placenta to transport these nutrients to the fetus. The ability of the fetus to utilize these nutrients may also depend upon the availability of other compounds, e.g., a balanced mixture of amino acids may be needed to build proteins. The fetus also has its own growth factors, which influence growth and differentiation. Normal fetal growth is the result of an equilibrated interplay between these different factors. Any imbalance between these factors can result in disorders such as fetal growth restriction (microsomia) or fetal overgrowth (macrosomia). Abnormalities in fetal growth and development which are related to an abnormal intrauterine environment, or which are related to problems in the genetic code, anatomy, or metabolism of the fetus itself, can be treated using the drug delivery systems and methods described herein.

The DDS can be used in promoting healthy pregnancy and fetal wellbeing, reducing the risk of preterm labor or fetal insufficiency, reducing the likelihood of, or treating, infections and bacterial growth, compensating for metabolic or other disorders of the mother or fetus, and in various other medical applications. In one method, at least one sensor, such as a biosensor, is implanted into, or proximate to, a region such as the womb, the amniotic sac, the maternal side of the placenta, the fetal side of the placenta, in or near the arterial or venous passageways of the umbilical cord (or respective areas of the chorion plate), the placenta, or the uterus, and the DDS dispenses drugs based upon the sensed data that are sensed by these sensors. For example, if the umbilical venous blood supply is lacking in a specific nutrient, blood gas, or hormone or if the supply is not flowing at a normal rate, then the DDS would dispense drug to compensate for this abnormality. When the DDS is used for obstetric applications its housing can be implanted in the vagina, womb, or in a proximal area of the body cavity, and some components, such as reservoirs, can exist outside of the body.

The DDS can provide therapeutic benefit by, for example, delivering drugs, neutralizing toxins (e.g., though filtering, chemical/molecular transformation of, or binding with, the toxin), removing harmful substances from the fetal environment through passive or active shunting, and performing other operations in response to sensed data, due to a delivery regimen, and/or in response to commands sent by an external patient programmer. More specifically, in addition to delivering fluids, the DDS can also remove fluids, or filter fluids transported to or from the fetus, for example, via the umbilical cord or amniotic fluid, and can also filter fluids in the body of the implantee. In one method, the DDS removes or alters fluids and other substances from the fetal environment which may be harmful to a developing fetus. For example, since the components of the amniotic fluid can affect the fetus (the fetus can swallow and urinate into this fluid), the DDS can pump amniotic fluid through a shunt or catheter which vents this fluid in a distal location ("shunt mode") and causes more amniotic fluid to be made thereby diluting the concentration of the harmful substance, or may have means to filter a fluid, such as the amniotic fluid, before returning it to the same or similar location ("filter mode"), and thereby remove undesirable compounds such as, for example, heavy metals which are thought to contribute to disorders such as autism (e.g., Bernard, 2002). The term "filtered fluid" can refer to fluid which is physically filtered or can refer to the neutralization of a substance through chemical, electrical, or molecular alteration which removes an unwanted characteristic of a substance. The DDS may also operate in a "push-sample" mode to send samples of the amniotic fluid to a distal site so that these samples can be analyzed by various laboratory procedures. The DDS can also use the push-sample technique to discard filtrate which it has stored temporarily ("purge mode") to a distal location in order to inhibit too much filtrate from building up in the DDS.

Removal or transformation (e.g., via chemical alteration) of various substances in the fluids of the uterus, placenta, umbilical cord, and amniotic fluids can aid in treatment of various disorders. The DDS can assist in removing/transforming carbon dioxide, bicarbonate, lactic acid, and hydrogen ions (or may dispense drugs which alter or chemically bind to these substances), and thereby assist in the protection against acidosis. This can be accomplished via electrochemical or chemical changes produced within specialized structures, such as a filter. Alternatively, the DDS can deliver drugs which assist (modify), the biochemical operations or cellular activity which occur in the placenta in order to increase its transfer of certain substances. For example, the DDS can deliver drugs which assist in the binding of oxygen to fetal hemoglobin, or can deliver drugs, such as 2,3-diphosphoglycerate (2,3-DPG), which change the affinity of the (adult) hemoglobin for oxygen, thereby increasing the transfer of oxygen across the placenta. When 2,3-DPG rises, in response to anemia or hypoxia, it binds to and stabilizes the deoxygenated form of hemoglobin, resulting in a shift of the oxygen dissociation curve to the right. Increasing 2,3-DPG on the maternal side of placenta and decreasing it in the fetal blood will lead to increased oxygenation. Using the DDS to deliver drugs which manipulate PH can also increase transfer/binding of gases within hemoglobin. Using the DDS to pump or re-route maternal blood can also compensate for reduced placental perfusion with maternal blood and the consequent decrease in fetal arterial blood oxygen content due to low pO2 (hypoxemic hypoxia).

The DDS can function in several manners or modes which have not described previously. For example, a flow compensation mode refers to the DDS assisting in pumping fluids within existing structures and vessels, for example assisting in the transfer of naturally available fluids through an artery or vein, or pumping stored fluids through these structures. The DDS can use flow compensation to assist in treating abnormalities of feto-placental flow within the umbilical cord. Flow redirection refers to the DDS serving as artery or vein and redirecting fluids from one part of the body to a different part of the body to assist, for example, in correcting abnormal vascularization of a structure such as the placenta. The DDS can deliver fluids which assist the activity of biological structures such as the placenta in maternal-fetal transport of, for example, nutrients or oxygen or help in the physical or metabolic elimination of, for example, carbon dioxide or fetal metabolites.

The maternal-fetal circulation may be conceptualized as two fluid circuits that affect each other via the placenta. From a pharmacological (model) standpoint the anatomical structures and fluids of the mother are considered a maternal compartment, the anatomical structures and fluids of the fetus create the fetal compartment, and the anatomical structures and fluids in the placenta can be conceptualized as a placental compartment. Both the maternal and fetal sides of the placenta have afferent structures which carry fluids towards the placenta, and efferent structures which carry fluids away from the placenta.

The term "maternal afferent structure" refers to structures that move fluid towards the fetal side of the placenta and away from the mother such as the internal iliac arteries, utero-placental arteries and structures within the basal plate of the placenta The term "maternal efferent structure" refers to structures that move fluid away from the placenta and towards the mother, for example, the utero-placental veins.

The term "fetal afferent structure" refers to structures which move fluids from the fetus towards the maternal side of the placenta and, for example, the umbilical arteries and the placental villi which feed them.

The term "fetal efferent structure" refers to structures which move fluids to the fetus from the maternal side of the placenta are such structures as the umbilical vein, the areas of the chorion plate to which the vein attaches, and other structures.

The term "intra-uterine target" refers to any structure in the uterus. The term "uterine afferent" refers to any structure, including supporting vasculature which brings fluids to the uterus and its related structures. The term "uterine efferent" refers to any structure, including supporting vasculature which carries fluids from the uterus and its related structures.

The term "related characteristics and processes" refers to physical (e.g. flow rate), chemical (e.g., amount of a hormone), biochemical, molecular, metabolic, anatomical (e.g. structural, developmental), physiological (e.g., transfer of a substance across a membrane) or other characteristics or processes which are related to the input of, output from, or flow within a structure.

The DDS can deliver drugs based upon data sensed from sensors that can measure, for example, intrauterine pressure, intra-umbilical pressure or flow rate, fetal heart rate, and maternal factors such as the mother's heart rate, blood concentration of a substance such as C-reactive protein, or glucose level. The medical DDS can use biosensors for sensing the composition of at least the amniotic fluid, umbilical vein, umbilical artery, maternal blood, or other sensors for sensing maternal EKG, fetal EKG, or fetal EEG. The sensors can sense blood gases such as oxygen, or PH, or sound (e.g. using a fluid-proof microphone). The sensors can incorporate or be in communication with miniature microdialysis probes and analysis systems.

The sensors can sense a physical, chemical, biochemical, molecular, physiological or other change in at least one structure moving fluids towards or away from the fetus. Sensors can be located in any of the afferent or efferent structures and can sense the related characteristics and processes of these structures. Sensors can also be located in the placental compartment, maternal and fetal compartments, including in the amniotic fluid. Sensors can also be located within the mother and/or within the fetus. Drugs can be delivered to any of the afferent or efferent structures and can also be delivered to the maternal and fetal compartments, including into the amniotic fluid. Sensors can also be located in, and drugs can be delivered to, other intrauterine targets. The sites of drug delivery can be the same as or different than the locations of the sensors.

By comparing sensed data from afferent and efferent structures, either on the maternal side or on the fetal side, input/output indices can be generated. For example, ratio indices based upon sensed data from the utero-placental arteries and veins provide information about what is being transferred across the placenta, and indices based upon sensed data from the arterial and venous passageways of the umbilical cord provide information about what is being metabolized by the infant. Additionally, creating indices from data sensed from the maternal afferent structures and the fetal efferent structures can provide measures of maternal-fetal transport. Further, indices can be created using sensed data from afferent and efferent structures on both the maternal and fetal sides of the placenta. Several examples, demonstrating the usefulness of some of these input/output indices, or other indices or ratio measures, will be discussed with respect to different medical disorders.

In one embodiment of the technology, a method of providing medical treatment to a fetus comprises delivering drug to a maternal afferent structure based upon sensed data sensed by at least one sensor located to sense at least one characteristic of fluid in at least one of the following locations: a maternal afferent structure, a maternal efferent structure, a fetal afferent structure, a fetal efferent structure, the amniotic sac, the placenta. The delivery of drugs used in treatment can, for example, produce a therapeutic effect by providing the fetus with a drug needed for the treatment of a medical disorder, but can also produce a therapeutic effect by causing a, physical, chemical, biochemical, molecular, physiological or other change in an afferent or efferent structure moving fluids towards or away from the fetus.

One embodiment is shown in FIG. 15a where a drug pump 6 is shown implanted in a mother for drug delivery to the fetus. Although the potential structures from which data can be sensed include the structures of the maternal compartment 804 (including maternal afferent structures 812, maternal efferent structures 808), structures of the fetal compartment 832 (fetal afferent structures 824, fetal efferent structures 820) and structures in the placental compartment 816, or in the fetus itself 828, sensors 21a and 21b have been implanted to sense information from a maternal afferent structure and a fetal efferent structure, respectively. Data from the sensors 21a and 21b are sent back to the drug pump 6 via the data link 90 which is implanted in a catheter which delivers fluids related to therapy from the drug pump 6 to a delivery target located in a structure within the placental compartment 816. One embodiment of a method of using a drug pump such as the DDS to treat a fetus is shown in FIG. 15b and includes a series of steps which are repeated as therapy occurs. The step of sensing data 840 comprises sensing data from the sensor 21a in the maternal afferent structure 812 and from the sensor 21b in the fetal efferent structure 820. The step of performing an evaluation routine to evaluate data 824, which can include processing the sensed data using signal analysis to obtain processed data which is then evaluated to produce a positive result 858 or negative result 852. In the case of a positive result 858, drug delivery occurs and drug is delivered through the catheter to the placenta. When the drug pump 6 is the DDS, drug can be evaluated using evaluation routines 320e which compare the sensed data to normative data stored in the population/self normative values table Rt3 of the database 322 delivered according to a drug delivery protocol which is based upon values contained in the delivery routines/protocols table Rt4 of the database 322.

The DDS contains algorithms and signal processing routines for automatically processing the sensed data into processed data. For example the fetal EKG, signal can be processed in order to obtain a meaningful measure such as inter-beat interval. Other characteristics of the fetal EKG can be the variability of the inter-beat-interval, or the classification of the fetal EKG signals into normal/abnormal beats using, for example, template matching algorithms. Measures such as rates of change may also be obtained, for example, which can be a useful measure when assessing if contractions of the uterine muscles are occurring more rapidly within a given time interval. The signal processing of the sensed data which transforms it into the processed data can include operations which enable transforming sensed data into meaningful units, and the creation of statistical summaries, ratios, classifications into abnormal/normal data, and for making computations upon characteristics such as rates of change, and for filtering, frequency analysis and other operations known to those skilled in the art of signal processing and statistics.

The sensed data and processed data can be evaluated, and based on this evaluation, at least one drug can be delivered to at least one site. Performing an evaluation of sensed/processed data may include comparing the values of the sensed/processed data to reference data which can be normative data such as a self norm from a previous time or set of times, or an age and sex appropriate population norm. The outcome can be a pass/fail result and can be determined by threshold criteria or statistical criteria and may be a score, such as a z score which indicates the statistical likelihood of abnormality. Performing an evaluation of sensed/processed data may also include using the values of the sensed/processed data from the umbilical vein and the values of the sensed data from the umbilical arteries to compute an input/output function (c.f., Osada et al, 2002) for at least one sensed substance and includes comparing this input/output function to normative data which may be a self norm from a previous time, or set of times, or an age/sex appropriate population norm, and the outcome is determined by a threshold criteria or a statistical criteria. The evaluation of sensed data can cause the detection of a medical event, which is any pattern or characteristic of the sensed data which indicates that drug delivery should occur.

Depending upon the physiological, chemical, or other factor that is being measured, sensing of measures can range from thousands of times per second (e.g., measurement of EKG) to once a day or less. Comparisons of these measures with normal values can be based upon the measures themselves, or may be based upon transformations of these measures. For example, the absolute measures of arterial or venous flow can be evaluated, or these may first be normalized, for example, using fetal abdominal or head circumference. These measures can also be evaluated with respect to changes in the fetus (e.g., apnea, a pulsitility index, oxygen/NO/Carbon-dioxide levels), or in the fetal environment (e.g., during periods of quiescence or during uterine contractions). Measures may be z-transformed against reference values as has been described by the inventor previously (e.g., U.S. Pat. No. 6,463,328, incorporated by reference herein) and the DDS can work in a closed loop capacity where the fluids are dispensed until certain criteria are met, or may function partially or fully in a user intervention mode where the DDS sends information to the external patient controller so that an implantee or doctor can evaluate the sensed data and choose an appropriate intervention.

A database containing normative values which are related to the development of the fetus is useful. When the drug pump is the DDS 10, the normative values can be contained in the population/self normative values table Rt3 in the database 322 and can be normative data for any location in which the sensor can be placed and can contain normative data for the characteristics which may be sensed by the sensors. Additionally the population/self normative values table Rt3 of the database 322 can contain statistical values for the normative data that are related to the sensed measures. Normative data can come from a healthy population, from a population which suffers from a similar disorder as the disorder for which treatment is being provided, or from the individual. The database should contain normative values that change with the age or development of the fetus. For example, Kwon et al (2003) have reported developmental changes in concentrations of amino acids in ovine maternal arterial plasma, fetal umbilical venous plasma, and fetal fluids. Three unique, major findings emerged from this study: 1) Ovine fetal:maternal plasma ratios for amino acids changed greatly during gestation, 2) the marked changes in concentrations of amino acids in ovine allantoic and amniotic fluids were associated with conceptus development (for example, concentrations of alanine, citrulline, and glutamine in allantoic fluid increased by 20, 34, and 18-fold, respectively, from day 30 to day 60 of gestation and were approximately 80, 30, and 60-fold, respectively, those in fetal plasma on day 60 of gestation), and 3) alanine, citrulline, and serine were unusually abundant in ovine allantoic fluid compared with any other biological fluid in animals suggesting important utilization of these amino acids by the fetus. Kwon et al also reported ovine fetal:maternal plasma ratios for amino acids throughout the entirety of gestation. Fetal:maternal plasma ratios for glutamate and serine were remarkably low and high, respectively, during late gestation. Since in vivo studies have demonstrated that little uterine uptake of glutamate occurs from maternal plasma but that placental uptake of glutamate occurs in the ovine fetus the authors conclude that extensive placental catabolism of glutamate and a high rate of fetal utilization of glutamate likely are the major factors responsible for its low concentrations in fetal plasma compared with maternal plasma. This article shows that substances, such as amino acid levels, change over time in a manner related to fetal age and development. Additionally, the results suggest that a decrease in the allontoic:plasma concentration could be used as an index reflecting a disorder, for example, a problem with fetal absorption of an amino acid. Accordingly, the database can contain normative values for concentrations within a specific fetal structure such as the allontoic sac and can also contain indices (e.g. ratios) created using concentrations of substances from two or more areas or fluids (e.g. an allontoic fluid:fetal plasma ratio).

The database can contain normative values for levels of substances in the maternal compartments, the fetal compartments and can contain normative measures for ratio of levels of substances between these two compartments. Further the database can contain normative measures for structures within each of these two compartments such as afferent and efferent structures and their supporting vasculature. Normative values can be values from a population which may be matched for characteristics such as age, weight, volume, developmental period, metabolism, flow rates and volumes of maternal or fetal fluids, or for levels of substances which are detected by sensors which are related to the drugs being released. Normative values may also be self norm values which are calculated based upon past values sensed for the fetus, the mother, or a combination or ratio of values for the fetus and the mother. The database can contain values which are derived from algorithms, equations, statistical measures and models which utilize the information stored in the database. For example, the database can contain a set of z-scores which can be computed from past sensed data and to which current sensed data can be compared. The data can be sensed data which is sensed by sensors of the DDS and can relate to presence, absence, or concentration of a substance, pressure, flow rate, fetal heart rate, or can be data obtained via external instrumentation operated by medical personnel or data obtained from analysis using laboratory techniques which have been sent to the database from an external patient controller. The database can be contained in the DDS or can be contained in an external patient controller or specialized computer which has communication means for communication with the implanted DDS.

The database can provide reference data values which are accurately related to the development of the fetus based upon single or multiple and direct indices or indirect indices. For example, fetal weight will increase similarly to allontoic fluid volume and amniotic fluid volumes. Accordingly, rather than measuring fetal weight, amniotic fluid volumes can be used to estimate the development or age of a fetus. The developmental stage or gestational age of the fetus can also be estimated using biochemical measures which can be absolute levels of a substance (e.g., absolute levels of glutamine) or ratio measures (e.g., glutamine-to-glycine ratio). Further, ratio's of substances which are sensed at two or more different structures can be used, such as the ratio of the concentration of a substance in the amniotic fluid compared to its concentration in the allontoic fluid.

Drug delivery can entail the delivery of therapeutic fluids such as vitamins, medications, growth factors, antioxidants, nutrients, amino acids, proteins, peptides, hormones, steroid products, and drugs which modulate the availability or metabolism of these substances.

Amino acids serve as essential precursors for the synthesis of proteins, peptides, neurotransmitters, amino sugars, purine and pyrimidine nucleotides, creatine, carnitine, porphyrins, melatonin, melanin, sphingolipids, polyamines, and nitric oxide. Amino acids also function as antioxidants, regulators of hormone secretion, major fuels for fetal growth, and signaling molecules. In particular, glutamine plays an important role in fetal nitrogen and carbon metabolism. Polyamines, synthesized from ornithine are essential to placental development and mammalian embryogenesis. Nitric oxide, synthesized from L-arginine, has enormous metabolic versatility and physiological importance, including potential roles in regulating placental angiogenesis and uterine blood flow during gestation. Additionally, serine and glycine are a main source of one-carbon units for cellular metabolism, including DNA synthesis and methylation. Since amino acids play a vital role in the growth, development, metabolism, and immune response of the conceptus, and in processes related to the maintenance of pregnancy, the DDS can modulate this by dispensing amino acids or substances that affect their metabolism.

There is ample evidence that an adverse intrauterine environment has harmful consequences for health in later life. Medical conditions such as metabolic disorders of the mother are one source that can contribute to a less than optimal environment. Further treatment of maternal disorders can also introduce substances and their metabolites which enter into the fetal environment. In disorders of maternal deficiency (e.g., nutritional deficiency such as iodine, iron, and other vitamins and minerals) or maternal metabolic disorders (e.g., thyroid disorders, diabetes, lupus) the DDS can provide direct or local delivery of therapeutic substances to aid in supplementation, compensation, or normalization of maternal-fetal fluids and the fetal environment and in the treatment of the fetus with respect to these abnormalities.

The DDS can assist in pregnancy where the mother suffers from a medical disorder such as diabetes, gestational diabetes, or other condition which results in insulin dysregulation, hyperglycaemia, or hypoglycaemia. As reviewed by Holemans et al 2003, both maternal diabetes and experimentally induced hyperglycaemia result in asymmetric overgrowth, due to an increased supply of glucose and other nutrients (Freinkel, 1980), which is associated with increased insulin secretion and hyperplasia of the insulin-producing B-cells in the fetus. As a result, in adult life, a reduced insulin secretion may occur. In contrast, intrauterine growth restriction is associated with low insulin secretion and a delayed development of the insulin-producing B-cells. These abnormalities in the fetal environment may induce a deficient adaptation of the endocrine pancreas and insulin resistance in later life. While intrauterine growth restriction in human pregnancy is mainly due to a reduced uteroplacental blood flow or to maternal undernutrition it can also be due to severe diabetes complicated by vasculopathy and nephropathy. Additionally, moderate or sever diabetes can interact with other factors in the fetal environment to produce hyperinsulinaemia or hypoinsulinaemia. Animal models have verified that intrauterine growth retardation can be obtained through pharmacological, dietary, or surgical treatment of the mother (arterial ligation). The endocrine pancreas and insulin-producing B-cells assist in the fetus' adaptation to an adverse intrauterine environment and this adaptation seems to have consequences after birth. Accordingly, the DDS of the current invention can be used to regulate levels of such substances as blood glucose by dispensing hyperglycemic and hypoglycemic hormones (e.g. insulin), or substances which will aid in the proper fetal metabolism of glucose, or substances which will affect the transfer (e.g., substances which will competitively bind to glucose transporters) of glucose across the placenta in the maternal-fetal or fetal-maternal direction, or enzymes involved in glucose metabolism, or genes or drugs which influence insulin secretion, absorption, binding, or metabolism in the maternal or fetal blood. The DDS can rely on sensors which sense the maternal blood either near the placenta, systemic levels (i.e., a glucose sensor in the arm of the mother) or both, and can dispense medication either next to or within the placenta or fetal compartment.

The DDS can assist in pregnancy where the mother suffers from a medical disorder such as hypothyroidism. For example, the DDS can sense local concentration of thyroid hormone near the fetal-placental unit (FPU) and dispense this hormone to keep levels within normal limits. Studies (e.g., Haddow, et al, 1999) have described mental defects occurring in children born to mothers with untreated hypothyroidism. Hypothyroidism is relatively common, occurring in about 1 in 100 women during the child-bearing years. It becomes more common with age, a feature which is relevant since women are increasingly deferring pregnancy. Since the developing fetus is unable to make its own thyroid hormone during the early stages of pregnancy the thyroid hormone must be transferred from mother to fetus across the placenta until the fetus' own thyroid gland starts to function during the second trimester. Even then, it is important that thyroid hormone levels made available to the fetus is well regulated. Accordingly, the DDS can assist in sensing hormone levels and modulating these by dispensing drugs to keep these levels within a desired range.

The DDS can assist in pregnancy where there is a hypoxic disorder whereby the fetus does not obtain normal levels of oxygen due to, for example, flow disorders where the flow in the umbilical cord is decreased compared to normal levels. Biological disorders which affect the availability of oxygen to reach the fetus are similar to internal hypoxic events which occur in individuals after birth. These events can affect the developing brain in a manner similar to a stroke and can affect other organs, such as the heart, similar to ischemic factors such as buildup of plaque in the supporting vasculature. Stroke is a loss of brain function resulting from interference with the blood supply to the central nervous system (CNS). CNS damage occurs in stroke as a result of hypoxia and decreased glucose availability. In the case of a transient ischemic event where oxygen supply is only briefly interrupted, the DDS can assist in lessening the effects of this event by responsively dispensing medication. For example, the effects of increased amounts of free radicals are lessened by dispensing neuroprotectants such as antioxidants. Antioxidants are natural or synthetic compounds which produce therapeutic effects in several ways including the removal of $O_2$, scavenging reactive oxygen species or their precursors, inhibiting reactive oxygen species (ROS) formation and binding metal ions needed for catalysis of ROS generation. In more chronic hypoxic conditions, the DDS can provide prophylactic treatment whereby the detrimental effects of a continuous deficiency are decreased. The effects of hypoxia on the CNS are very complex and involve mechanisms which can be compensated for by delivery of drugs, such as energy failure, loss of cell ion homeostasis, acidosis, increased intracellular calcium, excitotoxicity, and free radical-mediated toxicity, all of which contribute to ischemic necrosis and apoptosis, which are associated with factors such as loss of calcium and glutamate homeostasis (Gilgun-Sherki et al. 2002). One main objective of dispensing drugs to the fetus in response to a hypoxic condition is to decrease the effects of free radicals and harmful second messenger cascades. Free radicals (oxidizing agents) are highly reactive molecules generated predominantly during cellular respiration and normal metabolism. When the fetal environment supplies less oxygen than is needed, an imbalance between cellular production of free radicals and the ability of cells to defend against them (by antioxidant protective systems which create and upregulate the substances) may occur and is referred to as oxidative stress (OS) which is implicated in the pathogenesis of acute central nervous system (CNS) injury. The hypoxic event may increase the production of reactive oxygen species (ROS), sometimes drastically, leading to tissue damage via several different cellular molecular pathways. Accordingly, treatment with antioxidants will prevent propagation of tissue damage and improve both the survival and neurological outcome. Since the effects of the free radicals are related to the hypoxic event, it is important in the case of transient hypoxic events that the DDS supply the antioxidant drugs temporally close to the time of the hypoxic event and within the "neuroprotective window". Novel combinations of drugs providing protection against various types of injuries should exploit the potential synergistic effects of antioxidants and receptor modulators in stroke (e.g, US 20020123510).

By sensing or otherwise determining the oxygen levels which are available in the fluids supplying the fetus (e.g., via sensing umbilical flow rates or changes in metabolites in fluids leaving the fetus) and dispensing drugs which minimize the effects of free radicals, the DDS can greatly attenuate the risks associated with hypoxic conditions. Further, by sensing "specific markers of cerebral injury" such as proteins or polypeptides that are associated with brain tissue and neural cells, and which can be correlated with a cerebral injury, the DDS can monitor if the dispensed drugs are adequate and adjust the delivery regimen accordingly. For example, the drugs should be appropriate to the precise OS physiology (e.g., the type of ROS involved, the place of generation, and the severity of the damage) and the fluids of the fetal compartment may contain metabolites which indicate a specific type of OS has occurred. It is obvious that similar to the brain, other organs, such as the fetal myocardium, can also be protected from hypoxia or other conditions which lead to increases in free radicals, using antioxidants and calcium antagonists such as Anipamil. Drugs which can be delivered by the DDS to protect against damage due to free radicals can include drugs which promote the transcriptional up-regulation antioxidant substances in fetal cells, decrease the production of extracellular glutamate (e.g, by blocking the presynaptic release of glutamate and/or by blocking the excitation of postsynaptic neurons), ROS scavengers, calcium channel antagonists, cytokines, vitamins C and E or analogs (OPC-14117, MDL 74,722), melatonin, ascorbic and lipoic acids, polyphenols, and carotenoids, superoxide dismutase (SOD) and catalase (CAT), metal ion chelators, Glutathione, YM737, Creatine, spin-trap scavenging agents, etc.

The DDS can also assist in pregnancy where the mother is exposed to drugs, which are noxious to the infant, either through drug abuse or due to treatment of a medical condition. For example, delivered substances could counter the effects that maternal drug abuse treatment may have on the fetus. Naltrexone is a narcotic antagonist that blocks the opioid receptors in the brain. Naltrexone also blocks the reception of the opioid hormones that our brain and adrenal glands produce: beta-endorphin and metenkephalin. Many body tissues have receptors for these endorphins and enkephalins, including virtually every cell of the body's immune system. Opiod peptides serve as a negative regulator of growth, cell migration, differentiation, and survival. Blockade of opioids by opioid antagonists such as Naltrexone (NTX), results in a stimulatory response. NTX is able to cross the placenta and can be identified in fetal tissue. This can lead to increased organ weight and development in infants. Accordingly, the repercussions of using NTX in the treatment of alcoholism and drug abuse in pregnant mothers may be long-lasting and significant for the offspring. The implications are twofold. Firstly, in the case where a mother is undergoing treatment with NTX during pregnancy, the DDS could compensate for exposure to NTX through supplementation of opioid compounds. Additionally, since NTX can cause an increase in heart cells and the size of the heart (McLaughlin, 2002), NTX can be delivered by the DDS to augment growth in a fetus with congenital heart disease. By sensing the amounts of opioids or opioid antagonists in the fetal blood, and comparing these values to normative data, compensatory drug delivery may occur to lead to improved development of the fetus.

The DDS can be used to combat the effects of different drug treatments that a pregnant implantee may undergo such as treatment of metabolic disorders or psychiatric disorders such as depression. In one embodiment, the DDS uses a method of delivering one or more drugs to a mother which comprises limiting the total amount of drug delivered with respect to a specified amount of time, said limit being based upon data relating to the infant, or to both the mother and infant. This method is different than that of the prior art which delivers drug therapy based upon measures of only one patient (or implantee), rather than based upon measures derived from a second patient, or both the first and second patient.

The measures which can be sensed in order to modify drug treatment of the mother or compensate for this treatment by dispensing drug to the fetus create the sensed data. This sensed data is evaluated using information in a database 322 to determine if the data indicates that the drug related changes or the amount of drug to be dispensed are within acceptable limits. These limits can be based upon an equation or model whose variables include a history of past drug delivery and include characteristics of the fetus such as at least one of the following, absolute or relative levels of current or past sensed data, or changes in the levels of sensed data, or a combination of the two, said sensed data relating to measures of metabolic rate, metabolites, chemical or biochemical substances, or physiological events, or predicted gestational age, head volume, body volume.

The DDS can deliver therapy to treat fetal cardiac insufficiency due to persistent tachyarrhythmias. The DDS treatment can use medications which are currently given to the mother and therefore made available on a systemic level (e.g., with either digoxin alone or combined with other drugs) but can deliver these directly into the fetal compartment. Accordingly, the DDS can enable pregnancy to continue in preterm patients with risk of fetal cardiac failure and decreases mortality and morbidity.

Uteroplacental insufficiency is a major cause of perinatal mortality and complication in growth restricted fetuses (Di Naro, et. al. 2002). One major source of insufficiency is severely impaired feto-placental flow especially with respects to reversed blood flow in the diastolic component of the umbilical artery. Decreases in blood flow (and blood flow velocity) can be caused by decreases in the volume of the umbilical vessels or by increased viscosity of the material transported within these vessels (Jouppila et al, 1986; Drew et al, 1991) and leads to fetal compromise and complications. Raio et al (2003) found that all umbilical cord components (umbilical cord cross-sectional area, vein area, artery area, and Wharton jelly area) were smaller in intrauterine growth-restricted fetuses. The prevalence of lean umbilical cords (cross-sectional area <10th percentile for gestational age) was significantly higher in intrauterine growth-restricted fetuses compared with appropriate-for-gestational-age fetuses By sensing blood flow in the umbilical artery or vein, one can detect abnormal flow, as compared to the expected flow for age matched normative data. Although monitoring of umbilical venous flow has been shown to have better diagnostic accuracy than umbilical artery flow, either measure, or an index based upon a combination of these measures, can be used to monitor flow and for comparison to normative values. In addition to an implanted sensor which senses flow, flow can be based upon Doppler waveform analysis (e.g., color Doppler velocity integration or velocimetry). The DDS can act to modify, supplement or normalize this flow and thereby compensate for insufficiency. For example, the DDS can act as a pump which assists in moving fluid towards or away from the fetus which exists either within or external to the umbilical cord. Additionally the DDS can deliver blood thinning drugs to increase umbilical flow or can deliver oxygenated fluid or nutrients to compensate for abnormal flow. Since absolute blood flow increases as a function of gestational age (Lees et al, 1999), the normative values can be based upon factors such as estimated gestational age, head volume, body volume (or weight) and other measures well known to those skilled in the art. The "normal" flow values may also be based upon the cross-sectional area of the cord or one of its lumen (Di Naro et al., 2002).

The DDS can assist in compensating for abnormal blood flow to the uterus, placenta, or through the umbilical cord. The DDS can assist and compensate for problems in maternal-fetal transfer and transport which can be due to many sources including morphologic abnormalities which may deteriorate placental oxygen and other nutritional transport. The measures which are used to sense abnormal function will vary depending upon the structures being evaluated, for example, abnormal uterine artery blood flow can be indicated by abnormal velocity waveforms which may be identified by a persistent abnormal index, a persistent diastolic notch or an abnormal difference between the indices in the left and right uterine arteries (Thaler et al. 1992).

The prevention of fetal hypoxic injury and acidemia is another goal of modern obstetric practice (Luttkus et al, 2002). In addition to monitoring of the fetal EKG, heart rate monitoring is possible using reflected red and infrared light which can be converted into saturation values. Variable fetal heart rate decelerations may indicate a problem such as hypoxia. Fetal blood oxygen saturation can be estimated from pulse oximetry carried out by placing sensors on the fetus, such as on the fetuses' cheek or forehead, or other appropriate area. Umbilical artery decreased pH (or increased base deficit, altered lactate concentration) indicates acidemia or other abnormality associated with oxygen transport imbalance and impaired systemic oxygen utilization. Samples of fetal blood, obtained from umbilical vein or artery, can be output with the sample-push mode so that blood can be examined in the laboratory using blood gas analysis techniques such as hemoximetry. Umbilical blood pH should also be monitored because acidosis can be caused of a number of important conditions, aside from hypoxia, such as sepsis. Umbilical cord pH and base excess are related to subsequent adverse outcome for both umbilical artery and vein (Victory et al, 2003). Accordingly, in order to treat hypoxia or other uteroplacental insufficiency related to impaired feto-placental flow, the DDS can deliver medicants to the placenta or into the umbilical cord, such as substances to decrease viscosity of blood (e.g., EPA ethyl ester, PP-188 or "purified poloxamer 188", lipid-lowering drugs, and angiotensin converting enzyme) or anti-coagulants (e.g., Warfarin), and can deliver fluids such as oxygenated fluids, both toward or away from the fetus. The DDS can complement umbilical function by bypassing sections of the umbilical cord, or can replace umbilical cord function by transmitting fluids between the placenta and the fetus, or can assist in umbilical flow by pumping fluids within the umbilical vessels or can deliver or remove fluids to/from distal targets/sources.

The drug delivery methods and systems can be used to deliver appropriate gene therapy, provide nutrients to the fetus, and can be programmed to provide different drugs at specific concentrations and based upon different times during the pregnancy period and at different times in the prenatal period just prior to birth. The DDS can also be used for the promotion of fetal health by introducing vitamins and other types of dietary supplementation. The promotion of fetal health and the augmentation of the immune system of the fetus can be accomplished via administration of substances from the DDS, for example, antioxidants to counter the effects of free radicals, nutrients, vitamins to ensure proper growth, metabolism and immune system development, and antibiotics to deter fetal infection. The immune system of the fetus is modulated by the nutritional composition of the umbilical blood and thereby influences the ability of the fetus to respond to infections. Selenium depletion, which mediates immune response, in part, through glutathione peroxidases and thioredoxin reductase, has been shown to decrease T cell and panB cell proliferation, antibody titers, and natural killer cell activity (Dylewski et al, 2002). When selenium transfer, via the placenta or mammary glands is decreased, then selenium supplementation would act to increase the immune response of the fetus and neonate.

The DDS can also be used for the promotion of fetal health by aiding in gene therapy provided directly to the fetus, for example, via the umbilical cord. Gene therapy can be used in the case where the DNA of the fetus or parents indicates a predisposition for a genetic disorder. When metabolic screening and evaluation indicates gene therapy is warranted the DDS can greatly assist in the normal development of the fetus. Gene therapy can be accomplished by infusing the therapeutic substance into the umbilical vein either continuously, periodically, according to a treatment regimen, medical model, or in response to sensed data, and monitoring the effect through chemical sensors or by sending samples of the umbilical blood out using the sample-push mode. Some gene therapy will use several types of therapies in a sequential manner, for example, the therapy may change with fetal developmental, or, alternatively, the therapy may require the same therapy to be repeatedly administered over many months.

In one method of treating a fetus for a medical or genetic disorder, which is a simple embodiment of the invention, the DDS merely comprises an osmotic pump with a catheter containing a tip that is appropriately configured to enable drugs to be delivered within a uterine structure such as the umbilical cord. For example, the DDS contains an attachment means to secure the DDS near the cord, and to secure the catheter within the cord. Alternatively, the DDS may be comprised of more sophisticated components such as an inlet catheter which can transmit fluid from the umbilical cord into the DDS which can be filtered before redeploying the fluid into the cord, for example, sending the filtered fluid back into the umbilical vein from which it was drawn. In order to avoid build up of the unwanted filtrate, the drug delivery system can periodically operate in a "purging mode" which acts to send said unwanted substance through a waste disposal means, such as a catheter that terminates far from where the filtered fluid was obtained, so that said noxious filtrate does not re-enter an area where it can affect the fetus. Fluids from within the womb may act as diluents or buffer fluids for the DDS, for example, when it operates in a recirculation/replenishment mode or in purging mode.

In one embodiment, a method of using the implantable DDS for treating disorders of a fetus includes:
  a. implanting a drug delivery system into a pregnant female
  b. functionally connecting a drug delivery means, such as a catheter, into an umbilical vein of the umbilical cord, and.
  c. using an attachment means to reversibly secure a portion of the drug delivery means within the cord.

The medical drug delivery device of the current invention can be used in other obstetric applications, for example, in order to prevent or discourage miscarriage and preterm labor, thereby extending the term of pregnancy. Currently, 6-10% of all newborns in the industrialized world are born preterm and so such an application is medically important. In order for the extension of pregnancy to be helpful, it does not require that an infant is carried to full term. Of babies born at 24 weeks gestation, only 20% survive, but by 30 weeks gestation survival increases to 90%, with survival increasing roughly linearly over that period (Ingemarsson and Lamont, 2003). At more than 10,000 per infant, neonatal intensive care annually costs about $5 billion in the United States. Accordingly, increasing the term of pregnancy by a couple of weeks may greatly improve the survival of the neonate and decrease a significant national medical cost.

In one embodiment of the system and method, if the DDS senses the onset of contractions or chemical change which may lead to contractions, miscarriage or preterm labor, a drug is released to attenuate or halt this process. The DDS can also achieve this goal by providing therapeutic agents to prevent or treat infections such as intrauterine or genital tract infection. A strong association between upper genital tract infections and preterm delivery (before 30 gestational weeks) has been shown (Andrews et al, 1995). Estimates are that 20-40% of preterm deliveries may be caused by infection (Gibbs et al., 1992) and bacterial sources (e.g., subclinical chorioamnionitis or bacterial vaginosis). Inhibition of such factors through localized treatment, in addition to or instead of systemic treatment which are currently implemented, will aid in inhibiting preterm delivery and other complications associated with pregnancy. DDS treatment may be initiated when intervention is indicated by various markers and diagnostic tests, or DDS treatment may be utilized prophylactically when a predisposition is known due to a patient's history (e.g., prior preterm deliveries).

The prevention or delaying pre-term labor can occur via delivery of such drugs as tocolytics which act to counter contractions and antibiotics which prevent infection. The incidence of pre-term labor can also be decreased by assisting and promoting good fetal health, which is a general goal of using the DDS in obstetric intervention. For example, the DDS can be used to decrease the effects of hypoxia and uteroplacental insufficiency as has been discussed. Further, the DDS can be used to decrease effects of oxidants created in response to fetal insult, can improve or maintain fetal health by vitamin and nutrient supplementation, can attenuate or combat the effects of toxins that may be present in the maternal blood, and can assist in gene therapy to correct or compensate for genetic factors that can lead to pre-term labor.

The DDS can inhibit labor by delivering therapeutic substances according to a predetermined regimen, or continuously, or in response to sensed data such as an increased EMG signal, pressure signal, or biochemical concentration, sensed by at least one biosensor, which indicates either an increase in contractions or in a biological process that will lead to contractions. For example, the DDS can perform signal analysis to determine if labor is being initiated by analyzing sensed data from EMG or pressure sensors using spectral analysis and pattern matching and comparing the results of these operations to a threshold, past data sensed by the DDS, or normative data, to determine if a positive or negative result has occurred. When several catheters are provided evaluation of the sensed data can indicate which of one or more of the catheters will dispense drugs and in what temporal order. When each of the catheters is capable of delivering more than one drug the DDS will also determine which drug should be sent out of each catheter (this should be put in general section). When electrical stimulation leads are also utilized by the DDS, these can stimulate electrically to work in conjunction with the drug delivery. Prior art (e.g., US2002/0010494 "Uterus muscle controller" and US2003/0055467 "Smooth muscle controller")) has described using electrical stimulation to provide closed-loop control of uterine muscles for the inhibition of labor, but this prior art does not discuss using drug delivery, either alone or in conjunction with electrical stimulation in order to inhibit labor. While labor may be inhibited, this prior art does not address treating the causes behind the premature labor. Additionally, when drugs rather than electrical stimulation are used to inhibit labor the drug delivery protocol should be tailored to optimize drug delivery and this requires sending different drugs to different locations, or only out of a specific catheter that is proximal to the sensor which surpasses a specified criteria by the largest amount.

The DDS can assist in delaying labor and extending the pregnancy period by delivering drugs locally to specific targets, thereby decreasing the amount of drug needed to achieve effects. Tocolytics, which include oxytocin antagonists, cyclo-oxygenase inhibitors, calcium channel blockers, beta2 agonists, currently work well at inhibiting labor, but carry a large range of unwanted and serious side-effects. The DDS may be able to produce increased therapeutic benefit by locally (or in conjunction with maternal systemic delivery) delivering relatively low levels of these myometrial relaxants when sensors indicate a need. For example, the DDS catheters can be surgically implanted to administer tocolytics to the blood supply of the myometrium or other structure of the uterus, for example, via the radial uterine arteries in order to inhibit uterine contractibility. In one method of the present invention, fluids such as competitive antagonists or substances which bind to unused tocolytics drug may be delivered subsequent to the delivery of tocolytics, or in other areas that are relatively separate from the uterine muscles, in order to functionally neutralize, counter or at least diminish the unwanted side-effects of, the tocolytics after they have produced their desired effect.

There are many markers that are associated with increased risk of pre-term labor and may serve to indicate candidates for DDS therapy. For example, elevated C-reactive protein (CRP) levels as measured in the maternal blood taken at the beginning of a pregnancy are associated with roughly a twofold increase in the risk of preterm delivery (Hvilsom et al., 2002). Additionally, increased vaginal fluid CRP concentration has been associated with intra-amniotic infection and funisitis (Di Naro et al, 2003). High ferritin and IL-6 levels in the amniotic fluid may server as markers of inflammation in asymptomatic women destined to have an early pregnancy loss (Ramsey et al, 2002). Further, elevated levels of interleukin-6 in cervical secretions and in amniotic fluid, ostensibly present in response to infection, has been shown to be correlated with preterm delivery and can be detected with a strip test (Lange et al, 2003). Hvilsom et al (2002) have shown that a high C-reactive protein level, as indicated by a serological test of the maternal venous blood at the beginning of a pregnancy was indicative of a nearly twofold increase in risk of preterm delivery. Prostaglandins, which can become elevated in response to infection, serve as a trigger for the initiation of labor. While the role of prostaglandins is clearer for labor than for preterm labor (Guinn et al, 1995), agents that serve as antagonists of prostaglandin production, or which bind to or modify prostaglandins so that they fail to signal appropriately should assist in the inhibition of preterm labor. Andrews et al (2003) showed that fetal fibronectin in cervical/vaginal secretions is correlated with silent upper genital tract microbial infection, and may serve for a predictive marker of disposition for spontaneous preterm delivery. Although a series of studies have shown that antibiotic treatments have not been successful in preventing females, identified by fibronectin or other tests, from avoiding preterm labor and other complications, this type of intervention using an implanted DDS used in conjunction with other localized therapy may be more effective. Elevated C-reactive protein (CRP) levels as measured in the maternal blood taken at the beginning of a pregnancy are associated with roughly a twofold increase in the risk of preterm delivery (Hvilsom et al., 2002). Additionally, increased vaginal fluid CRP concentration has been associated with intra-amniotic infection and funisitis (Di Naro et al, 2003). High ferritin and IL-6 levels in the amniotic fluid may server as markers of inflammation in asymptomatic women destined to have an early pregnancy loss (Ramsey et al, 2002). Hvilsom et al (2002) propose that self norm of C-Reactive Protein from early in pregnancy period could be more sensitive indicator of increased risk of preterm labor than absolute cutoff based upon population norms. Accordingly, past values of sensed data, contained as self-norm values in the database of the DDS, can assist in prevention of pre-term labor. Accordingly, in one method of the current invention the DDS is implanted when biological markers indicate a biological abnormality which leads to an increased risk of preterm labor. These markers are used to provide the DDS with appropriate drugs, to guide catheter implantation to provide delivery of drugs to appropriate sites, to guide sensor implantation to provide sensing of data relevant to the disorder indicated by the marker, to program the DDS with drug delivery protocols appropriate for the disorder, and to guide treatment.

Using the DDS to improve and assist pregnancy and the antenatal environment may offer considerable advantages for a host of current medical problems. By implanting a DDS which utilizes sensors, normative data (either population or self-norm values), simple modeling, and either open or fully-/partially-closed-loop control, appropriate substances can be locally dispensed. Through appropriate catheter placement drugs can be delivered directly into the umbilical cord, amniotic fluid, the components of the uterus and placenta, and the supporting vasculature or even directly into the organs of the fetus. Insufficient or excessive amounts of an environmental factor (e.g., blood pH, oxygen, nutrients) can be supplemented or compensated for in order to provide improved antenatal development. The provision of bolus delivery in response to an acute event, or low level continuous delivery which is relatively independent of maternal factors of metabolism, can be assisted by sensors which measure substances traveling both towards and away from the fetus or supporting anatomical structures in order to measure the effects of drug delivery and construct input/output functions for the modulated target system or organ. In time, surgical techniques will likely allow DDS delivery to bypass the umbilical cord, or other structures involved in carrying fluids to and away from the fetus, and deliver fluids directly into the developing fetus. However, even if fluids are delivered directly to the fetus, the substances moving through the umbilical cord should still be monitored in order to determine the metabolites that are being delivered and removed from the fetus by the natural mechanisms.

The DDS can be used after birth occurs to continue to assist in promoting the health of the newborn infant by modifying the mother's breast milk. The DDS system and methods of the current invention can be implanted so that the catheter tip is inserted into the mammary glands, and can function to add nutrients, enzymes, vitamins, and other substances to breastmilk. In one embodiment, a flow meter or other means can ensure that a specified amount of drug is provided throughout the day, which may be independent from, correlated with, or dependent upon the amount of breastmilk imbibed by the baby. According to an alternative method the breastmilk is measured, either by the DDS or by, for example, laboratory tests in order to determine its composition. The drugs delivery regimen is then adjusted according to the composition of the breastmilk, age of the infant, the nutritional/metabolic needs of the infant, medical tests performed on the infant or a combination of more than one of these factors. While prior art has described medical mixtures which can be given to the infant to improve its health, immune system, and antioxidant status, and which may be mixed with breast milk (e.g., US2003/0104078), the prior art does not describe using these mixtures in an implantable DDS, changing the mixture based upon the needs or age of the infant, or changing the mixture based upon, or to compensate for, specific deficiencies in the mother's breast milk.

The implanted drug delivery system also has applications for personnel in the military, pilots, and astronauts. For example, a soldier who is injured and caught behind enemy lines, or who is engaged in lengthy combat, or a pilot or astronaut who is in charge of flying a craft over many hours or days, may tend to ignore needs met by proper nourishment, and may become tired or drowsy leading to an increased risk of making errors that could have large consequences. The implanted drug delivery system could become useful by sensing such parameters as insulin levels, free radicals, heart rate, EEG, histamines, blood gas levels, etc. and could release vitamins, nutrients, steroids, antibiotics, anti-inflammatory agents, analgesics, aspirin, stimulants, and dietary supplements, in response to users commands or as indicated by sensed data. In these applications, the DDS can be implanted subdermally using a local anesthetic.

The DDS allows for continuous delivery of a variable concentration of drug, for Sequential Bolus dosing, for fluids to be pumped into the DDS where they can be filtered or modified, for multiple drugs to be accurately dispensed through a single catheter or multiple catheters, and for functioning according to the methods described herein to achieve advantages of drug delivery and treatment.

The DDS system and methods for delivering drugs can be advantageous because the concentrations, rates of delivery, and volumes of delivery of the drugs may be rapidly tailored according to drug delivery regimens or according to the implantee's needs, because it efficiently uses space within the DDS, and because relatively inert substances can be replaced rather than requiring the replacement of controlled substances. Further, when several reservoirs exist, each having a separate concentration of a drug, each of which is meant for separate treatment requirements, the DDS is replenished when any one of the multiple reservoirs runs out. If one of the reservoirs is used more than the others; this could lead to an inefficient, and overly taxing, replenishment schedule.

Implanted drug delivery systems have not been previously described which act to mechanically, chemically, or electrically or electrochemically filter (or modify or neutralize) fluids of the implantee in order to remove unwanted filtrate or decrease the harmfulness of a the fluids components. Further, the DDS describes removal of the filtrate using a purging mode so that a large abundance of filtrate does not inhibit the function of the device.

Various components of the medical drug delivery system can be miniaturized considerably compared to the embodiments shown in the FIGS. The scale of components in the FIGs are for illustration purposes and do not necessarily represent the sizes and scales of the components.

Components of the drug delivery system can be external, for example, attached to the arm placement with the catheters passing subcutaneously. The housing of the drug delivery systems can be created with bio-compatible plastic on the outside and titanium on the inside, causing them to be lightweight and have long-term durability.

Although the disclosure herein has been drawn to one or more exemplary systems and methods for drug delivery devices, catheters, and TCFAs, various modifications thereof will be apparent to those skilled in the art without departing from the spirit and scope of the invention as outlined in the claims appended hereto.

I claim:

1. A drug delivery system for delivering a drug into a patient, the apparatus comprising:
   an implantable drug pump having at least one drug reservoir filled with a drug and pumping means, the drug pump further configured to be operated jointly with a catheter assembly in order to provide controlled delivery of said drug to said catheter assembly;
   a catheter assembly configured for operating in conjunction with the implantable drug pump and for providing circular flow of a therapeutic fluid therethrough, the therapeutic fluid comprising a first volume of a fluid and a drug contained therein;
   a flow controller under control of the implantable drug pump for controlling a flow rate of the therapeutic fluid within the catheter assembly; and
   a distal catheter member configured for operating to selectively permit: the therapeutic fluid to do at least one of the following selected from the group of: a) circulate, and b) be dispensed to a predetermined location in the patient.

2. The drug delivery system of claim 1, wherein the catheter assembly comprises:
   a first lumen having a first proximal end for coupling to a drug delivery device and a first distal end for positioning at the target site;
   a second lumen having a second proximal end for coupling to the drug delivery device and a second distal end for positioning at the target site, the first lumen and the second lumen adapted for fluid communication therebetween;
   a flow control system positioned at the first and second distal ends for directing inter-lumen fluid flow between the first and second lumens and for directing output fluid flow from the distal ends to the target site, the flow control system having at least one directional flow controller adapted to receive at least one control signal from the drug delivery device.

3. The assembly of claim 2 further comprising the flow control system having a plurality of the directional flow controllers.

4. The assembly of claim 3, wherein the flow controllers are each responsive to the control signals from the drug delivery device.

5. The assembly of claim 4, wherein the control signals configure the plurality of the flow controllers in an output flow open state and an inter-lumen flow closed state, such that inter-lumen fluid flow is inhibited and output fluid flow is enabled from at least one of the lumens.

6. The assembly of claim 4, wherein the control signals configure the plurality of the flow controllers in an output flow closed state and an inter-lumen flow open state, such that output fluid flow is inhibited and inter-lumen fluid flow is enabled between the lumens.

7. The assembly of claim 3, wherein the plurality of the directional flow controllers further comprises a first directional flow controller and a second directional flow controller.

8. The assembly of claim 7, wherein the open state of the first directional flow controller provides for inter-lumen fluid flow simultaneously with the closed state of the second directional flow controller inhibiting the output fluid flow.

9. The assembly of claim 7, wherein the first directional flow controller is associated with the first lumen and the second directional flow controller is associated with the second lumen, such that the first and second flow controllers cooperate to inhibit respective output fluid flow from each of the lumens while providing for inter-lumen fluid flow.

10. The assembly of claim 2, wherein the first lumen and the second lumen are selected from the group comprising: a dual lumen catheter; and individual segments of a single lumen catheter.

11. The assembly of claim 2, which additionally includes at least one of the following:
   a pump in fluid communication with the lumens and the drug delivery device and configured to accomplish at least one of the following: to pump fluid from the drug delivery device into either of the two lumens, to pump fluid out of either of the two lumens and into the drug delivery device, and to circulate fluids within the lumens; and a sensor for sensing at least one physical property of at least one fluid, said property including at least one of the following, a color, a chemical, a concentration.

12. The assembly of claim 2 wherein the assembly is part of a multi-stage catheter and wherein a second catheter is attached to the distal end of the lumens and receives the fluid from the flow control system causing said fluid to flow through said second catheter prior to delivery to said patient.

13. The assembly of claim 2, wherein said flow control system incorporates at least one of the following: a pump, a second drug delivery device which is realized within a microchip, and sensors.

14. The drug delivery system of claim 1 wherein the fluid is fluid endogenous to the patient.

15. The drug delivery system of claim 1 wherein the fluid is a diluent.

16. The drug delivery system of claim 1 wherein the fluid is a pusher fluid.

17. The drug delivery system of claim 1 wherein the catheter assembly comprises a closed loop of lumen defining at least one sealed channel.

18. The drug delivery system of claim 1 wherein the catheter assembly comprises a closed loop of lumen defining at least one sealed fluid circuit.

19. The drug delivery system of claim 1 wherein the catheter assembly comprises a double-lumen catheter.

20. The drug delivery system of claim 1 wherein concentration of the drug in the therapeutic fluid varies in different portions of the catheter assembly.

* * * * *